US008017596B2

(12) United States Patent
Montero et al.

(10) Patent No.: US 8,017,596 B2
(45) Date of Patent: Sep. 13, 2011

(54) PHOSPHONATES USEFUL AS MODULATORS OF T-γ-9-δ-2 ACTIVITY

(75) Inventors: Jean-Louis Montero, Valflaunes (FR); Ibrahim Zgani, Richmond, VA (US); Chantal Menut, Montferrier sur Lez (FR); Valérie Gallois, Paris (FR)

(73) Assignee: Innate Pharma, S.A., Marseilles (FR)

( * ) Notice: Subject to any disclaimer, the term of this patent is extended or adjusted under 35 U.S.C. 154(b) by 0 days.

(21) Appl. No.: 12/656,049

(22) Filed: Jan. 14, 2010
(Under 37 CFR 1.47)

(65) Prior Publication Data
US 2010/0204184 A1   Aug. 12, 2010

Related U.S. Application Data

(63) Continuation of application No. 10/498,313, filed as application No. PCT/FR02/04190 on Dec. 5, 2002, now abandoned.

(30) Foreign Application Priority Data

Dec. 11, 2001 (FR) ..................................... 01 15971

(51) Int. Cl.
*A61K 31/662* (2006.01)
*A61K 31/663* (2006.01)
(52) U.S. Cl. ........... 514/99; 514/106; 514/124; 514/134
(58) Field of Classification Search .................... 514/99, 514/134, 106, 124; 558/217, 178, 177; 562/8, 562/24; 568/15; 549/222; 435/29
See application file for complete search history.

(56) References Cited

U.S. PATENT DOCUMENTS

| 4,924,024 | A  | 5/1990  | Biller        |
| 5,177,239 | A  | 1/1993  | Singh et al.  |
| 5,827,838 | A  | 10/1998 | Cohen et al.  |
| 2006/0030546 | A1 | 2/2006 | Jomaa et al. |

FOREIGN PATENT DOCUMENTS

| EP | 534 546 | 3/1993 |
| EP | 0534546 A1 | 3/1993 |
| EP | 1 153 928 | 11/2001 |
| FR | 2 034 481 | 12/1970 |
| FR | 2 372 170 | 6/1978 |
| GB | 2 294 462 | 5/1996 |
| WO | 94/19357 | 9/1994 |
| WO | 97/19091 | 5/1997 |
| WO | 00/12516 | 3/2000 |
| WO | 00/12519 | 3/2000 |
| WO | 00/59916 | 10/2000 |
| WO | 02/02057 | 1/2002 |
| WO | WO 02/083720 A2 | 10/2002 |
| WO | WO 03/009855 A2 | 2/2003 |

OTHER PUBLICATIONS

Morikawa et al., Immunosuppressive Activity of Fosfomycin on Human T-Lymphocyte Function in Vitro, Dec. 1993, Antimicrobial Agents and Chemotherapy, vol. 37, No. 12, p. 2684-2687.*

George Popjak, et al., "Inhibition of liver prenyltransferase by citronellyl and geranyl phosphonate and phosphonylphosphate", Journal of Lipid Research, vol. 26, no. 9, pp. 1151-1159, 1985.
Sarah A. Holstein, et al., "Phosphonate and biosphosphonate analogues of farnesyl pyrophosphate as potential inhibitors of farnesyl protein transferase", Bioorganic & Medicinal Chemistry, vol. 6, No. 6, pp. 687-694, 1998.
Stephen S. Kalinowski, et al., "Mechanism of inhibition of yeast squalene synthase by substrate analog inhibitors", Archives of Biochemistry and Biophysics, vol. 368, No. 2, pp. 338-346, Aug. 15, 1999.
Chemical Abstracts, vol. 114, No. 15, Apr. 15, 1991 Columbus Ohio, US; abstract No. 135661, Fedurov, V.V, et al., "Cytotoxic effects of amino and phosphonate analogs natural prenylpyrophosphates", XP002212511 abstract & DOKL, AKAD, NAUK UKR, SSR, SER, B: Geol., Khim, Biol. Nauki (1990), (9), 79-82-1990
Chemical Abstracts, vol. 87, No. 4, Jul. 25, 1977 Columbus, Ohio, US: abstract no. 23847, Shakirov, R.Z. et al: "Polyelectrolyte properties of polymers based on dienephosphonic acids", XP002212559 abstract & Vysokomol. Soedin., Serb (1977), 19(4), 315-18, 1977.
Paul R. Hanson, et al., Ring closing metathesis reactions on a phosphonate template, Tetrahedron Letters, vol. 39, No. 23, pp. 3939-3942, Jun. 4, 1998.
Chemical Abstracts , vol. 108, No. 5, Feb. 1, 1988 Columbus, Ohio, US; abstract No. 38140. Kolodyazhnyi, O. I. et al., "Carbon-phosphorus analogs of natural prenylpyrophosphates" XP002212560 abstract & DOPOV. AKAD. NAUK UKR, RSR, SER. B. Geol., Khim, Biol., Nauki (1987), (7), 51-3, 1987.
Ibrahim Zgani, et al., "Synthesis of vinyl pyrophosphonate analogues of farnesyl pyrophosphate: new potential inhibitors of farnesyl protein transferase", Heteroatom Chemistry, vol. 13, No. 7, pp. 654-661, 2002.
Hanson, et al., Tet. Lett., 39(1998) 3939-3942, see p. 3939.
Popjak, et al., J. Lipid Research, vol. 26, 1985, 1151-1159, especially p. 1151.
Kalinowski et al., Archives of Biochemistry and Biophysics, vol. 368, No. 2, Aug. 15, 1999, pp. 338-346, especially p. 1152.
Patani et al.,Chem Rev, 1996, vol. 96 (8), especially p. 3147.
Kunzmann, V. et al., "Stimulation of gd T cells by aminobisphosphonates and induction of antiplasma cell activity in multiple myeloma", blook, Jul. 15, 2000, pp. 384-392, vol. 96. No. 2.
Haynes,. D. A., "Occurrence of Pharmaceutically Acceptable Anions and Cations in the Cambridge Structural Database", Journal of Pharmaceutical Sciences, vol. 94, No. 10, Oct. 2005.
Poccia F., et al., "Innate T-cell immunity to nonpeptidic antigens", Immunology Today, 1998, vol. 19, No. 6, pp. 253-256.
Ismaili J. et al., "Human gd T Cells Induce Dentrictic Cell Maturation", Clinical Immunology, vol. 103, No. 2, Jun. 2002, pp. 296-302.
Peng, S. et al., "Propagation and Regulation of Systemic Autoimmunity by gd T Cells". The Journal of Immunology, 1996. 157: 5689-5698.
Constant P., et al., "Stimulation of Human gd T Cells by Nonpeptidic Mycobacterial Ligands", Science, Apr. 8, 1994, vol. 264-270.

* cited by examiner

*Primary Examiner* — Golam M M Shameem
*Assistant Examiner* — Kristin Bianchi
(74) *Attorney, Agent, or Firm* — Saliwanchik, Lloyd & Eisenschenk

(57) ABSTRACT

The invention concerns novel phosphonate derivatives, preparation method, use thereof as ligands modulating T γ9δ2 lymphocyte activity and pharmaceutical compositions comprising them.

20 Claims, 6 Drawing Sheets

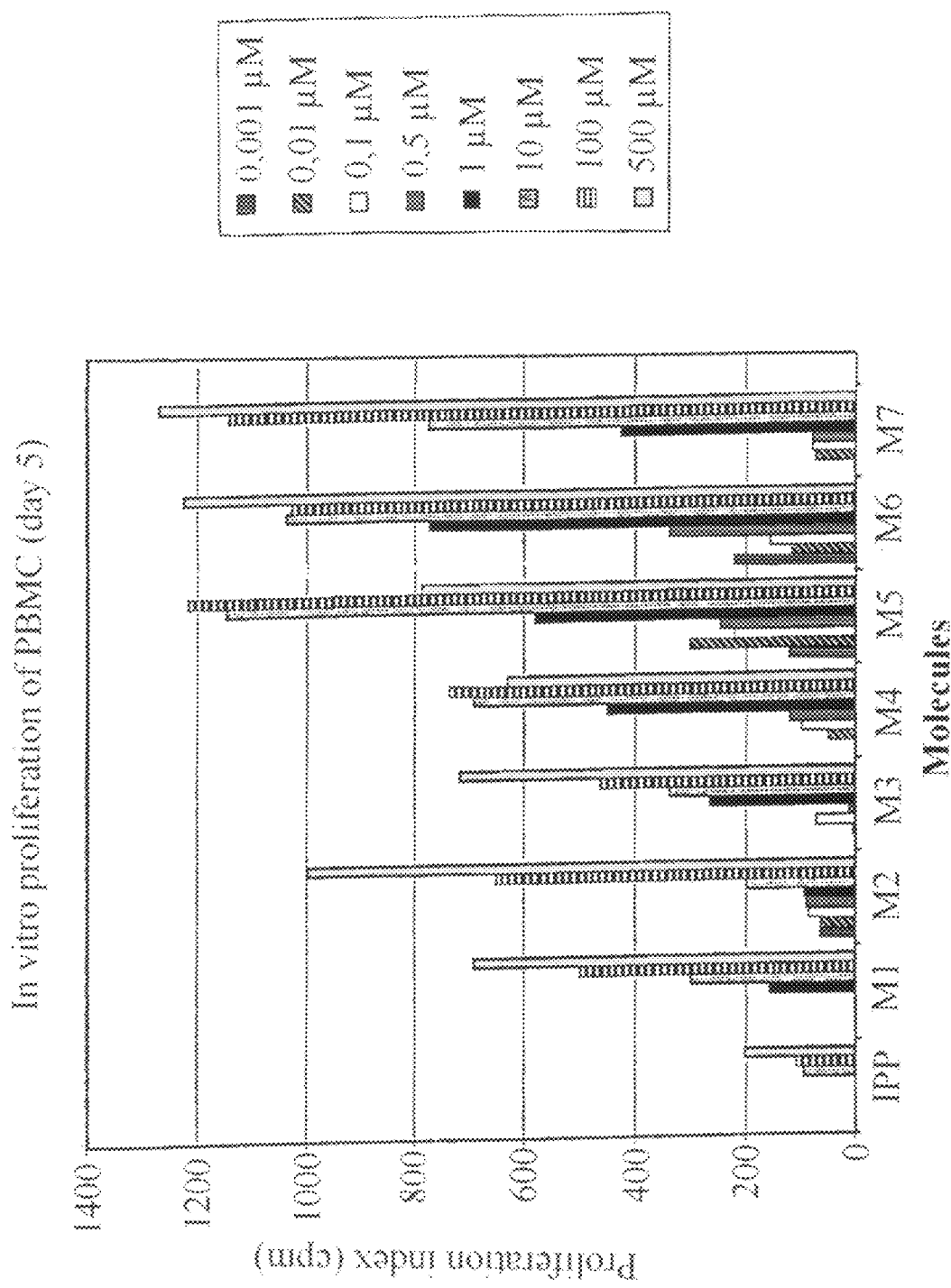

PHOSPHONATES USEFUL AS MODULATORS OF T-γ-9-δ-2 ACTIVITY

The invention relates to new phosphonate derivatives, the preparation method and use thereof as ligands modulating γ9δ2 T lymphocytes and pharmaceutical formulations comprising same.

T lymphocytes are cells which develop in the thymus. They are responsible for cell mediation immunity. T lymphocytes are divided into two subgroups corresponding to the receptors they comprise: αβ T lymphocytes and γδ T lymphocytes.

The γδ T lymphocytes of primates present in the peripheral blood (humans, monkeys) represent, in the healthy individual, generally from 1 to 5% of the lymphocytes in the blood and play a role in the immune system. γ9δ2 T lymphocytes (sometimes also referred to as γ2δ2 T lymphocytes) are γδ T lymphocytes comprising Vγ9 and Vδ2 variable region receptors. They represent the majority of γδ T lymphocytes in human blood.

When they are activated, γ9δ2 T lymphocytes can exert a powerful cytotoxic activity on cells carrying pathogenic agents. A significant increase in the population of Vγ9δ2 cells in the presence of various pathogenic agents has particularly been demonstrated.

They may consist of cells infected with viruses, such as for example human immunodeficiency virus, or HIV ("Selective increase of a subset of T cell receptor gamma delta T lymphocytes in the peripheral blood of patients with human immunodeficiency type 1 infection", De Maria A. et al, J Infect. Dis. 165, 917-919, 1992) or by another virus such as simian immunodeficiency virus or SIV, herpes simplex virus or HSV, human herpes virus-6 or HHV-6, vaccinia.

They may also consist of cells infected by bacterial infectious agents or protozoa such as, for example *Mycobacterium tuberculosis*, the infectious agent responsible for tuberculosis in humans ("The primary response of human γ/δ+ T cells to *Mycobacterium tuberculosis* is restricted to Vδ9-bearing cells", Kabelitz D. et al, J. Exp. Med., 173, 1331-1338, 1991), *Salmonella typhi*, the infectious agent responsible for salmonellosis, *Brucella melitensis*, responsible for brucellosis, *Francisella tularensis*, the pathogenic agent in tularaemia, *Plasmodium virax* and *Plasmodium falciparum* which are responsible for malaria, *Listeria monocytogenes* which is the pathogenic agent in listeriosis in humans. ("Role of γδT lymphocytes in immune response in human and mice", A. Salerno and F. Dieli, Critical Reviews in immunology, 18: 327-357 (1998)).

In addition, some tumoral cell lines are recognised and destroyed by γ9δ2 T lymphocytes, such as for example Daudi cells (P. Fish et al, Science, 250: 1269-1273 (1992)) or the RPMI 8226 line (Seclin, L. K. et al, Scand. J. Immunol. 36: 107-117 (1992)).

γ9δ2 T lymphocytes recognise a wide variety of antigens expressed in human and/or primate conditions. For this reason, molecules are required that make it possible to stimulate the proliferation of γ9δ2 T lymphocytes, so as to favour the immune response against these conditions.

In addition, it is known that there is a correlation between γ9δ2 T lymphocytes and the development of certain chronic inflammatory conditions such as systemic lupus erythematosus, multiple sclerosis, rheumatoid polyarthritis, Behcet's disease, allogenic transplant rejection, chronic autoimmune hepatitis, polymyositosis, inflammatory colon diseases ("Role of γδ T lymphocytes in immune response in human and mice", A. Salerno and F. Dieli, Critical Reviews in immunology, 18: 327-357 (1998)).

In the case of chronic inflammatory conditions, molecules are required that make it possible to limit the proliferation of γ9δ2 T lymphocytes.

In order to be able to regulate the proliferation of γ9δ2 T lymphocytes, it was therefore attempted to develop ligands modulating γ9δ2 T lymphocytes.

It has been demonstrated that human γ9δ2 T lymphocytes react, in the case of mycobacterial infection, with four phosphate structure non-peptide natural molecules, referred to as phosphoantigens, which have a stimulating activity for a concentration of the order of 1 to 5 nM (nanomolar) (WO 95/20673 and "Stimulation of human γδ T cells by nonpeptidic mycobacterial ligands" Patricia CONSTANT et al, Science, 264, p. 267-270). However, these natural antigens are not completely identified and can only be produced in small quantities (WO 95/20673).

It has also been demonstrated that monoalkylphosphates, particularly monoethylphosphate, induce in vitro, the proliferation of γ9δ2 T lymphocytes; isoprenylpyrophosphate is also recognised as stimulating the proliferation of γ9δ2 T lymphocytes "Non peptide ligands for human γδ T-cells", Tanaka Y. et al, Proc. Natl. Acad. Sci. USA 1994, 91: 8175-8179).

While phosphate derivatives have demonstrated a beneficial activity as a stimulant of the proliferation of γ9δ2 T lymphocytes, in vitro, it is known that the presence of a high number of phosphatases in the human body or in the body of primates will not enable these molecules to reach their target if they are used in vivo.

For this reason, the Applicant attempted to develop molecules liable to be ligands modulating γ9δ2 T lymphocytes and showing a sufficient stability to retain activity when applied to the human or animal body, particularly in primates.

In the prior art (V. Kunzmann et al, Blood, 15 Jul. 2000, vol. 96, No. 2, p 384-392), biphosphonate compounds, such as alendronate, ibandronate and pamidronate and their activity as stimulants of γ9δ2 T lymphocyte proliferation are known. However, it is demonstrated in the above-mentioned study that only amino-biphosphonates had an effect on T lymphocyte proliferation, while, according to this study, the other phosphonates tested showed no activity of this type.

The Applicant surprisingly discovered new derivatives belonging to the phosphonate family, said compounds showing an activity of ligands modulating γ9δ2 T lymphocyte proliferation, said compounds being less likely to be broken down by the enzymes present in the human or animal body, particularly by phosphodiesterases, than the compounds according to the prior art. In addition, said compounds being more hydrophobic than the compounds according to the prior art, they have a better bioavailability.

Therefore, the invention relates to new compounds complying with the formula I below, wherein:

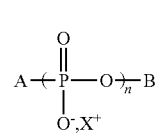

(I)

A represents a linear, branched or cyclic alkyl group, saturated or unsaturated at $C_1$-$C_{50}$, said alkyl group (alkenyl, alkynyl) may comprise one or more aromatic groups, it may comprise one or more ether bridges, one or more functions selected from: a carboxylic acid, an ester, an amide, a nitrile, a hydroxyl, an aldehyde, a ketone, a halogen, an amine, a thiol, a thio-ketone, an episulfide, a selenol, a seleno-ketone, a sulfide, a sulfone, a sulfoxide, it may comprise one or more heterocycles, n is an integer ranging from 1 to 4, X represents a group selected from a hydrogen atom and a pharmaceutical acceptable organic or mineral cationic group, B represents a group selected from:

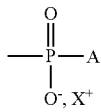

X and wherein X and A have the same significations above, with the exception of (E,E) 1-pyrophosphono-4,8,12-trimethyl-trideca-3,7,11-triene, (E,E)1-pyrophosphono-2,6,10-trimethylundeca-1,5,9-triene, [3-[N-trans-2-[(3E)-4,8-dimethyl-3,7-nonadienyl]-2-methyl-trans-3-[(1E,5E)-2,6,10-trimethyl-1,5,9-undecatrienyl]-1-cyclopropyl]amino]propyl]phosphonophosphate and salts thereof.

The aromatic groups liable to be contained in the alkyl (alkenyl, alkynyl) chain of A particularly include: phenyl, pyridine, benzophenone.

The heterocycles liable to be contained in the alkyl (alkenyl, alkynyl) chain of A particularly include the epoxide and aziridine groups.

When the alkyl (alkenyl, alkynyl) chain of A comprises an ether bridge, said bridge may be located at any position of the chain, including inside a cycle. Preferentially, it is located in the δ position with respect to the phosphorus atom.

The $X^+$ groups that can be used according to the present invention include: $H^+$, $Na^+$, $NH_4^+$, $K^+$, $Li^+$, $(CH_3CH_2)_3NH^+$ or an enzyme-labile ester function.

According to a first alternative embodiment of the invention, A represents a linear, branched or cyclic alkyl (alkenyl, alkynyl) group in $C_1$-$C_{50}$ comprising at least one double bond.

Preferentially, the compounds according to this alternative embodiment of the invention and complying with formula I above are characterised in that A comprises 3 to 25 carbon atoms, more preferentially, A comprises 5 to 10 carbon atoms.

The preferred compounds complying with formula I according to this alternative embodiment of the invention include:

(E)1-pyrophosphonobuta-1,3-diene
(E)1-pyrophosphonopenta-1,3-diene
(E)1-pyrophosphono-4-methylpenta-1,3-diene
(E,E)1-pyrophosphono-4,8-dimethylnona-1,3,7-triene
(E,E,E)1-pyrophosphono-4,8,12-trimethyltrideca-1,3,7,11-tetraene
(E,E)1-phosphono-4,8-dimethylnona-1,3,7-triene
(E,E,E)1-phosphone-4,8-dimethyltrideca-1,3,7,11-tetraene-(E,E)1-triphosphono-4,8-dimethylnona-1,3,7-triene
4-triphosphono-2-methylbutene
α,β-di-[3-methylpent-3-enyl]-pyrophosphonate
1-pyrophosphono-3-methylbut-2ene α,γ-di-[3-methylbut-3-enyl]-triphosphonate
α,β-di-[3-methylbut-3-enyl]-pyrophosphonate
allyl pyrophosphonate
allyl triphosphonate
α,γ-di-allyl-triphosphonate
α,β-di-allyl-pyrophosphonate
4-phosphono-2-methylbutene
(E,E)4-[(5'-pyrophosphono-6'-methyl-penta-2',4'-dienyloxymethyl)-phenyl]-phenyl-methanone
(E,E)4-[(5'-triphosphono-6'-methyl-penta-2',4'-dienyloxymethyl)-phenyl]-phenyl-methanone
(E,E,E)[4-(9'-pyrophosphono-2',6'-dimethyl-nona-2',6',8'-trienyloxymethyl)-phenyl]-phenyl-methanone
(E,E,E)[4-(9'-triphosphono-2',6'-dimethyl-nona-2',6',8'-trienyloxymethyl)-phenyl]-phenyl-methanone
5-pyrophosphono-2-methylpentene
5-triphosphono-2-methylpentene
α,γ-di-[4-methylbut-4-enyl]-triphosphonate
5-pyrophosphono-2-methylpent-2-ene
5-triphosphono-2-methylpent-2-ene
α,γ-di-[4-methylpent-4-enyl]-triphosphonate
9-pyrophosphono-2,6-dimethylnona-2,6-diene
9-triphosphono-2,6-dimethylnona-2,6-diene
α,γ-di-[4,8-dimethylnona-2,6-dienyl]-triphosphonate
5-phosphono-2-methylpentene
5-phosphono-2-methylpent-2-ene
4-pyrophosphono-2-methylbutene
1-phosphono-3-methylbut-2-ene
allyl phosphonate
4-methyl-2-oxa-pent-4-enyloxymethylpyrophosphonate
4-methyl-2-oxa-pent-4-enyloxymethyltriphosphonate
α,β-di-[4-methyl-2-oxa-pent-4-enyloxymethyl]-pyrophosphonate
α,γ-di-[4-methyl-2-oxa-pent-4-enyloxymethyl]-triphosphonate
4-methyl-2-oxa-pent-4-enyloxymethylphosphonate.

According to a second alternative embodiment of the invention, A represents a linear, branched or cyclic alkyl (alkenyl, alkynyl) group in $C_1$-$C_{50}$ comprising at least one α-halohydrine group according to formula II below, wherein Y represents an atom selected from fluorine, chlorine, iodine and bromine:

According to a third alternative embodiment of the invention, A represents a linear, branched or cyclic alkyl (alkenyl, alkynyl) group, saturated or unsaturated in $C_1$-$C_{50}$ comprising at least one epoxide group.

According to a fourth alternative embodiment of the invention, A represents a linear, branched or cyclic alkyl (alkenyl, alkynyl) group, saturated or unsaturated in $C_1$-$C_{50}$ comprising at least one tertiary alcohol group.

According to a fifth alternative embodiment of the invention, A represents a linear, branched or cyclic alkyl (alkenyl, alkynyl) group, saturated or unsaturated in $C_1$-$C_{50}$ comprising at least one α-diol group.

According to a sixth alternative embodiment of the invention, A represents a linear, branched or cyclic alkyl (alkenyl, alkynyl) group in $C_1$-$C_{50}$ comprising at least one aldehyde group or α-hydroxyaldehyde group.

The invention also relates to a method to prepare the compounds complying with formula I.

The compounds, according to the invention, may be prepared according to the reaction models given below, depending on the various A and B groups.

Where n=1 and B=X

Model 1:

When A represents a saturated or unsaturated alkyl, possibly comprising one or more substituents listed above but A comprises no unsaturation at α of the phosphorus atom in the final molecule according to the formula I, the following model is proposed:

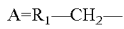

$R_1$ represents a linear, branched or cyclic alkyl group, saturated or unsaturated at $C_1$-$C_{49}$, said alkyl group (alkenyl, alkynyl) may comprise one or more aromatic groups, it may comprise one or more ether bridges, one or more functions selected from: a carboxylic acid, an ester, an amide, a nitrile, a hydroxyl, an aldehyde, a ketone, a halogen, an amine, a thiol, a thio-ketone, an episulfide, a selenol, a seleno-ketone, a sulfide, a sulfone, a sulfoxide, it may comprise one or more heterocycles.

The alcohol $R_1$—OH is treated: (1) with methyl sulfonate chloride in the presence of n-triethylamine in dichloromethane. The methylsulfonate group is then substituted by a bromide by treatment (2) with lithium bromide in dimethylformamide at 50° C.:

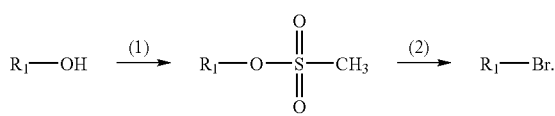

The alkyl bromide $R_1$—Br is treated with diethyl methylphosphonate in the presence of n-butyl lithium in tetrahydrofuran at −70° C.

The diethyl alkyl phosphonate $R_1CH_2PO(OC_2H_5)_2$ is converted into the corresponding phosphonic acid $R_1CH_2PO(OH)_2$ according to Rabinovitz's method (Rabinovitz, R. J. Org. Chem. 1963, 28, 2975-2978) by treating with a trimethylsilyl halide to give a bis(trimethylsilyl) phosphonate which is hydrolysed very easily to produce the corresponding phosphonic acid.

Preferentially, trimethyl silyl bromide is used rather than chloride which requires excessively long reaction times or iodide which generates iodohydric acid which is frequently a problem in multifunctional molecules.

Model 2:

When A comprises unsaturation at α of the phosphorus atom in the final molecule according to the formula I, the following model is proposed:

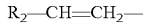

$R_2$ represents a linear, ramified or cyclic alkyl group, saturated or unsaturated at $C_1$-$C_{48}$, said alkyl group (alkenyl, alkynyl) may comprise one or more aromatic groups, it may comprise one or more ether bridges, one or more functions selected from: a carboxylic acid, an ester, an amide, a nitrile, a hydroxyl, an aldehyde, a ketone, a halogen, an amine, a thiol, a thio-ketone, an episulfide, a selenol, a seleno-ketone, a sulfide, a sulfone, a sulfoxide, it may comprise one or more heterocycles.

The alcohol $R_2$—$CH_2$—OH is converted into the aldehyde $R_2$—CHO by one of the conventional treatments performed by those skilled in the art:

Swern's oxidation (Mancuso, A. J. and Swern, D. Synthesis 1981, 165.185) by treatment with allyl chloride in DMSO oxidation with manganese dioxide (Bergman, R. and Magnusson, G. J. Org. Chem. 1986, 51, 212-217)

oxidation with pyridinium bichromate in DMF at −30° C.

Preferentially, the latter oxidation method is used when $R_2$ comprises one or more double bonds conjugated with the aldehyde function.

The aldehyde $R_2$—CHO is then treated with tetraethyl methylene diphosphonate in the presence of sodium hydride in THF at ambient temperature to produce the corresponding diethyl alkyl phosphonate:

according to the Horner-Wadswoth-Emmons method (Wadsworth, W. S. Jr and Emmons, W. D., J. Am. Chem. Soc. 1961, 83, 1733-1738).

According to the nature of the substituents comprised by $R_2$, the isomer E or the isomer Z is preferentially obtained.

However, it would also be possible to envisage obtaining the same product by means of any other method known to those skilled in the art.

Diethyl alkyl phosphonate is then converted into the corresponding phosphonic acid using Rabinowitz's method as explained above.

Preferentially, the Rabinowitz reaction is carried out in the presence of pyridine in dichloromethane. The bis (trimethyl silyl) phosphonate is hydrolysed by treating in a basic aqueous solution, such as for example, by adding an 0.1 N aqueous soda solution.

The final product is isolated by means of purification methods (extractions) well-known to those skilled in the art.

Phosphorylation:

Where n>1 and where n=1 and B represents:

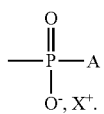

The method preferentially used to perform the phosphorylation of the phosphonic acids obtained in the previous steps is Michelson's method (Michelson, A.M. Biochem. Biophys. Acta. 1964, 91, 1-13). This method consists in activating the phosphonic diacids initially by reacting the n-tributylammonium mono-salt on diphenyl phosphate chloride (generally rapid reaction) to produce an "activated" phosphonic anhydride. Said anhydride reacts without being isolated in pyridine, with n-tributylammonium orthophosphate, to produce the expected pyrophosphonate.

This reaction takes place in two steps with no purification of the intermediate compound: the first step is performed in two hours and displacement of diphenyl phosphate group requires an eight-hour reaction time. Both reactions are complete and the yields are satisfactory.

The final product is isolated by means of purification methods well-known to those skilled in the art (silica gel chromatography for example). This reaction gives rise to the formation of secondary products: triphosphonate, symmetric diphosphonate, symmetric triphosphonate, etc., which are of interest in the present invention and are isolated by means of chromatography.

When A comprises functional groups liable to be affected by the reactions mentioned above such as bromination, oxidation reactions, addition of dialkyl methylene phosphonate, dialkyl phosphonate deprotection, phosphonylation, etc., suitable protective groups of these functional groups are used. Such protective groups are well-known to those skilled in the art and are selected in order to withstand the reaction conditions mentioned above and to be able to be removed under sufficiently safe conditions so as not to affect the integrity of the remainder of the molecule.

To illustrate the methods liable to be used to prepare the molecules according to the invention more clearly, the following synthesis models:

When A comprises an ether bridge, preferentially in a of an allyl function:

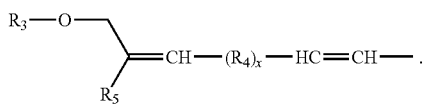

$R_3$, $R_4$, $R_5$, represent independently from each other, a linear, a ramified or cyclic alkyl group, saturated or unsaturated at $C_1$-$C_{40}$, said alkyl group (alkenyl, alkynyl) being liable to comprise one or more aromatic groups, comprise one or more ether bridges, one or more functions selected from: a carboxylic acid, an ester, an amide, a nitrile, a hydroxyl, an aldehyde, a ketone, a halogen, an amine, a thiol, a thio-ketone, an episulfide, a selenol, a seleno-ketone, a sulfide, a sulfone, a sulfoxide, comprise one or more heterocycles, x being an integer equal to 0 or 1.

Model 3:
The alcohol

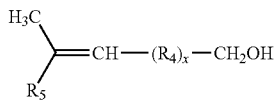

is treated by 3,4-dihydropyrane and pyridinium p-toluene sulfonate to produce the derivative

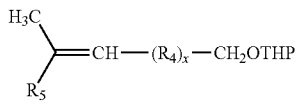

with a quantitative yield, under conditions well-known to those skilled in the art (Miyashita, N.; Yoshikoshi, A.; Grieco, P. A. J. Org. Chem. 1977, 42, 3772-3774).

The resulting ether is oxidised under the effect of a catalytic quantity of selenium dioxide in the presence of t-butyl hydroperoxide to regenerate the oxidising agent in situ from the selenium formed (Umbreit, M. A.; Sharpless, K. B. J. Am. Chem. Soc. 1977, 99, 5526-5528), (Bhalerao, U. T.; Rapaport, H. J. Am. Chem. Soc. 1971, 93, 4835-4840), (Rabjohn, N. Org. React. 1976, 24, 261-426).

Oxidation with selenium dioxide is a very selective means to obtain an alcohol or aldehyde function according to the experimental protocol used. This reagent oxidises preferentially allyl methyls forming an E stereochemistry compound. Depending on the conditions used, this gives either an alcohol

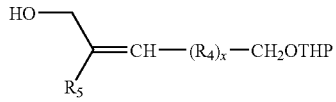

or an aldehyde

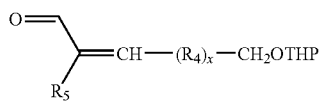

Coupling is carried out by treating the alcohol with sodium hydride in a THF reflux followed by the addition of alkyl bromide $R_3$—Br.

In the specific case where A is a 4-(methyl oxyalkyl)benzophenone type derivative, 4-(bromomethyl)benzophenone is prepared beforehand by treating 4-methylbenzophenone with bromine in a carbon tetrachloride reflux.

Ether deprotection is carried out under the effect of a catalytic quantity of pyridinium p-toluene sulfonate in methanol thus giving, with quantitative yields, the compounds

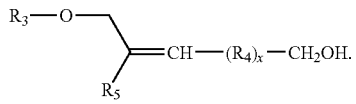

(Miyashita, N.; Yoshikoshi, A.; Grieco, P. A. J. Org. Chem. 1977, 42, 3772-3774).

According to model 2 explained above, alcohol is then oxidised into aldehyde and then converted into alkyl phosphonate.

The Michelson reaction can then be applied to produce the corresponding pyrophosphonate and polyphosphonylate derivatives.

Model 4:
When A comprises and aldehyde function and unsaturation in a of phosphorus:

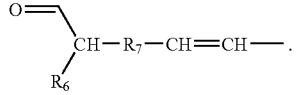

$R_6$, $R_7$, represent independently from each other, a linear, a ramified or cyclic alkyl group, saturated or unsaturated at $C_1$-$C_{40}$, said alkyl group (alkenyl, alkynyl) being liable to comprise one or more aromatic groups, comprise one or more ether bridges, one or more functions selected from: a carboxylic acid, an ester, an amide, a nitrile, a hydroxyl, an aldehyde, a ketone, a halogen, an amine, a thiol, a thio-ketone, an episulfide, a selenol, a seleno-ketone, a sulfide, a sulfone, a sulfoxide, comprise one or more heterocycles, the following synthesis model may be proposed:

The compound

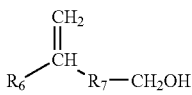

is used as the starting product.

The alcohol function is protected with a benzoyl group by treating with benzoyl chloride to produce the corresponding benzoyl ether with a quantitative yield. An oxidising hydroboration reaction of this compound makes it possible to obtain the corresponding alcohol:

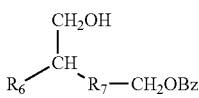

which will subsequently be protected in the form of tetrahydropyrane ether by treating with 1,4-dihydropyrane in dichloromethane in the presence of a catalytic quantity of pyridinium p-toluene sulfonate; tetrahydropyrane ether is obtained in this way with a quantitative yield. This compound is hydrolysed by treating with $K_2CO_3$ in methanol to produce the compound

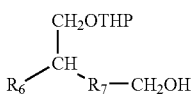

oxidation of this alcohol under Swern's conditions gives the aldehyde

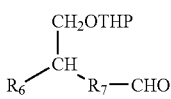

which is converted into its phosphonic derivative via the Horner-Wadsworth-Emmons reaction. Finally, the tetrahydropyrane ether split by treating with a catalytic quantity of pyridinium p-toluene sulfonate in methanol produces the alcohol:

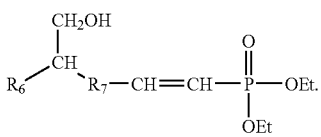

The alcohol obtained above is oxidised under Swern's reaction conditions to produce the corresponding aldehyde. By treating with trimethylsilane bromide in a basic medium, the phosphonic diester function of this compound is converted into phosphonic diacid. The last step (optional) of this synthesis is the phosphorylation of the Michelson phosphonic diacid compound to produce the pyrophosphonic compound:

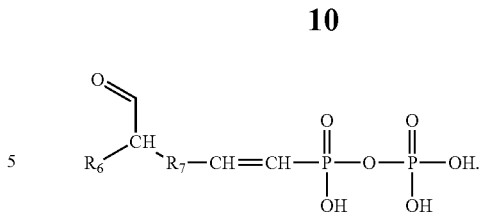

On the basis of the general models given above, and their knowledge of organic synthesis, those skilled in the art will be able to devise specific synthesis processes for derivatives comprising varied substituents.

The invention also relates to pharmaceutical formulations characterised in that they comprise, in addition to a pharmaceutically acceptable excipient, at least one compound according to formula I above. It also relates to the use of a compound complying with formula I above for the preparation of a medicinal product modulating the proliferation of γ9δ2 T lymphocytes. According to the invention, the compounds complying with formula I above show an activity of ligands modulating the proliferation of γ9δ2 T lymphocytes. The term modulating means either stimulating or inhibiting.

Compounds stimulating the proliferation of γ9δ2 T lymphocytes are of particular interest in preventing and/or treating infectious diseases such as those caused by the viruses, bacteria, protozoa agents listed above. They may also be useful for the prevention and/or treatment of certain tumours.

Some chronic inflammatory conditions may, according to the invention, be prevented and/or treated by γ9δ2 T lymphocytes proliferation inhibitors according to the invention.

The invention relates to the use of a compound complying with formula I above for the preparation of a formulation intended for the prevention or treatment of a condition inducing γ9δ2 T lymphocyte activation.

In particular, the invention relates to the use of a compound complying with formula I for the preparation of a formulation intended for the prevention or treatment of an infectious disease, such as those caused by viruses, bacteria, protozoa agents, particularly human immunodeficiency virus, or H.I.V., simian immunodeficiency virus or SIV, herpes simplex virus or HSV, human herpes virus-6 or HHV-6, vaccinia, tuberculosis, salmenollosis, brucellosis, tularaemia, malaria, listeriosis.

The invention also relates to the use of a compound complying with the formula I above for the preparation of a formulation intended for the prevention or treatment of certain tumours.

The invention also relates to the use of a compound complying with formula I above for the preparation of a formulation intended for the prevention or treatment of a chronic inflammatory disease, such as, for example, systemic lupus erythematosus, multiple sclerosis, rheumatoid polyarthritis, Behcet's disease, allogenic transplant rejection, chronic autoimmune hepatitis, polymyositosis, inflammatory colon diseases.

The invention also applies to therapeutic or diagnostic formulations comprising at least one compound according to formula I. More specifically, it relates to a therapeutic formulation comprising a compound according to formula I, capable of being administered to a primate, particularly humans.

As a general rule, the term prevention may be understood to include vaccination. Therefore, the invention also applies to preventive immunostimulant formulations or vaccine formulations including at least one compound according to formula I.

A formulation according to the invention may also advantageously comprise one or more other active ingredient(s), particularly an active ingredient acting in synergy with a compound according to formula I. In particular, a compound according to the invention may act as a vaccine adjuvant. The vaccination formulation according to the invention is then formed by a known vaccination formulation to which a quantity of compound according to the invention is added.

The formulation according to the invention is prepared in a pharmaceutical form enabling the administration thereof either by the systemic route, particularly by the oral route, parenteral route, directly in the peripheral blood of the primate or by the topical route. Depending on the case, one or more suitable excipients are added to the compound according to formula I. The pharmaceutical form of a therapeutic or preventive formulation according to the invention is produced according to the selected route of administration, by means of conventional pharmaceutical formulation techniques. The quantity and concentration of compound(s) according to the invention and the dosage are determined with reference to known chemotherapy treatments of the diseases to be treated or prevented, in view of the bio-activity of the compounds according to the invention with respect to γ9δ2 T lymphocytes, the subject to be treated, the disease in question and the desired biological effects.

Advantageously, the compound according to the invention is administered in a quantity capable of obtaining in the patient's peripheral blood a concentration greater than the $IC_{50}$ concentration of the compound.

The invention also relates to a method to prepare a formulation having the property of modulating γ9δ2 T lymphocyte proliferation, wherein at least one compound according to the invention is used. The invention also relates to a method to prepare a therapeutic or preventive formulation with respect to the conditions mentioned above, wherein at least one compound according to the invention is used. The invention particularly relates to a method to prepare a formulation intended to be administered to humans or animals, by the oral route, by the parenteral route, particularly in contact with the peripheral blood of humans or animals or by the topical route, for the preventive or curative treatment of a condition such as that mentioned above, wherein at least one compound according to the invention is used.

In addition, the invention relates to the use of a compound according to formula I in an in vitro biological test as a γ9δ2 T lymphocyte proliferation stimulant.

In addition, the invention relates to the use of a compound according to formula I in an in vitro biological test as a γ9δ2 T lymphocyte proliferation inhibitor.

It also relates to an in vitro diagnostic kit for a condition inducing γ9δ2 T lymphocyte activation, characterised in that it comprises at least one compound according to the invention. It also relates to an in vitro diagnostic kit for a condition inducing γ9δ2 T lymphocyte inhibition, characterised in that it comprises at least one compound according to the invention. In particular, it relates to an in vitro diagnostic kit for an infectious disease, such as those caused by viruses, bacteria, protozoa agents, a tumour or chronic inflammatory disease, the diagnostic kit functioning according to the usual principles known for such devices and based on stimulation or inhibition by the compounds according to the invention.

BRIEF DESCRIPTION OF THE DRAWINGS

FIG. 1 In all the experiments, isoprenyl pyrophosphonate (IPP) is selected as the reference. The results are shown in FIG. 1, which represents the proliferation index as a function of each molecule for the various concentrations tested. In this figure, it is observed that the molecules $M_1$: (E) 1-pyrophosphono-4-methylpenta-1,3-diene, $M_2$: (E) 1-pyrophosphono-penta-1,3-diene, $M_3$: (E)1-pyrophosphono-buta-1,3-diene, $M_4$: 5-pyrophosphono-2-methylpent-2-ene, $M_5$: α,γ-di-[4-methylpent-4-enyl]-triphosphonate, $M_6$: 5-pyrophosphono-2-methylpentene, $M_7$: 5-triphosphono-2-methylpentene are more effective than IPP in inducing T lymphocyte proliferation.

FIG. 2A gives the profile (size FSC and granularity SSC) of the cells studied. FIG. 2B shows a fresh PBMC before culture. FIG. 2C shows a fresh PBMC after 5 days in culture. FIGS. 2D to 2L show a PBMC after 5 days in culture in the presence of the molecule tested. FIG. 2D: cells stimulated with 1μg/ml phytohaemagglutinin A (PHA). FIG. 2E: cells stimulated with 100μM isoprenylpyrophosphate (IPP). FIG. 2F: cells stimulated with 100μM 1-pyrophosphono-4-methylpenta-1,3-diene. FIG. 2G: cells stimulated with 100μM (E) 1-pyrophosphono-penta-1,3-diene. FIG. 2H: cells stimulated with 100μM (E) 1-pyrophosphono-buta-1,3-diene, FIG. 2I: cells stimulated with 100μM 5-pyrophosphono-2-methylpent-2-ene. FIG. 2J: cells stimulated with 100μM α,γ-di-[4-methylpent-4-enyl]-triphosphonate. FIG. 2K: cells stimulated with 100μM 5-pyrophosphono-2methylpentene. FIG. 2L: cells stimulated with 100μM 5-triphosphono-2-methylpentene.

Figures 2A, 2B, 2C, 2D, 2E:
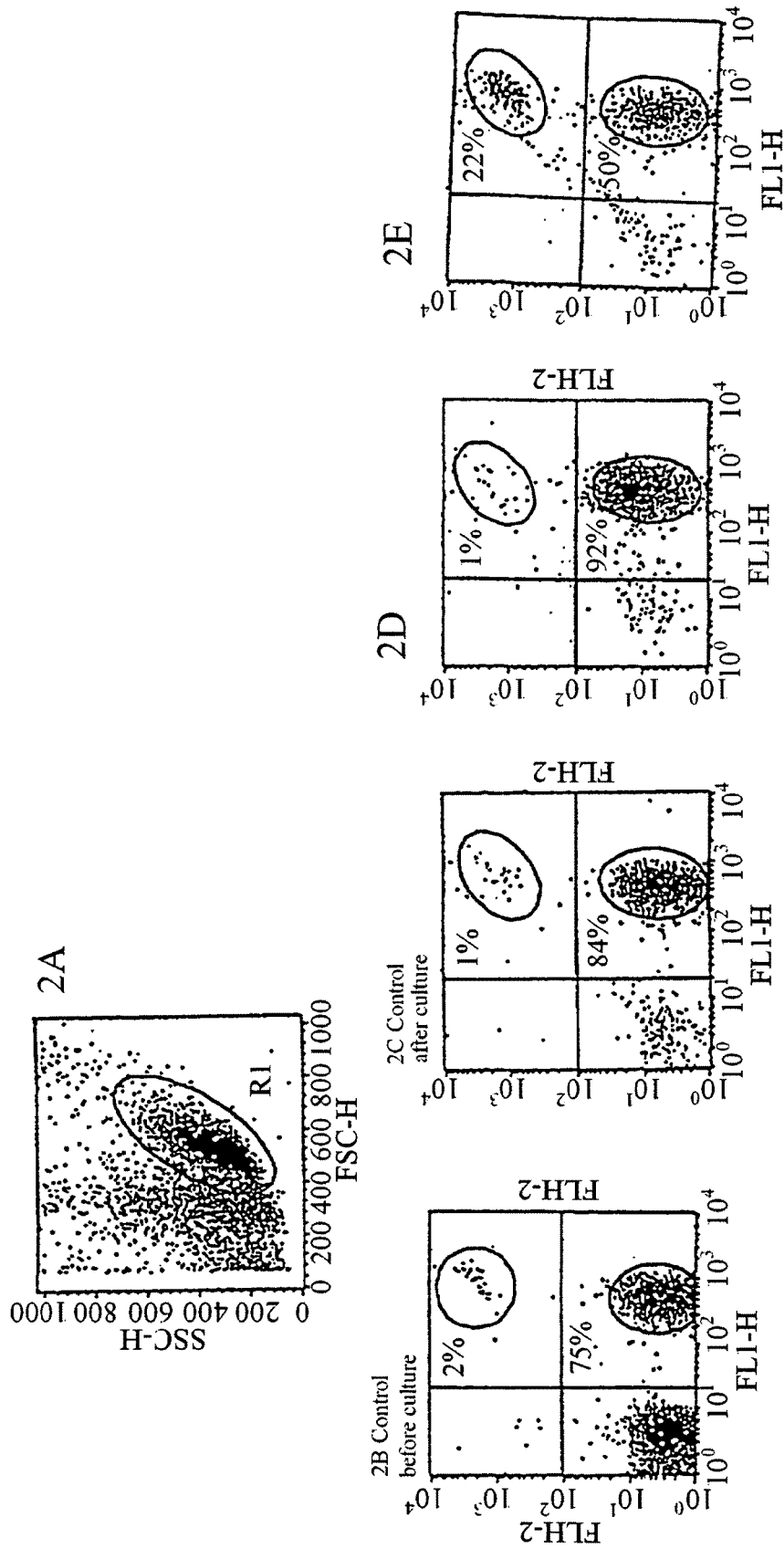
FIGS. 2A-2L. In order to verify selectivity with respect to Vγ9/Vδ2 lymphocytes of molecule activating potential, PBMCs, were cultured and analysed after 5 days of culture in the presence of various molecules by flow cytometry immunofluorescence. For this, the cells are retrieved, washed in PBS and then incubated in the presence of human anti-CD3 monoclonal antibodies conjugated with fluoroscein (FITC, FL1) and human anti-Vγ9 coupled with biotin and then detected with Streptavidine-phycoerythrin conjugate (ST-PE, FL2). The markings are produced by incubating for 30 minutes with 0.5 μg of each antibody per million cells. The analysis is performed after washing on a FACScalibur-SORT cell analyser-sorter cytofluorimeter (Becton Dickinson, Mountain View, CA).

The invention will be understood more clearly on reading the additional description below which refers to examples of embodiments of formulations according to the invention, and demonstrations of their therapeutic properties.

However, it must naturally be understood that these examples are only given as illustrations of the invention and do not represent a limitation in any way.

EXAMPLES

General Conditions

Thin layer chromatography (TLC) was performed on MERCK 60 $F_{254}$ silica plates. The compounds were detected using different methods according to their nature:
  Chromophore compounds: ultraviolet light (254 nm).
  Aldehydes: soaking in a 5% rhodanine solution in ethanol followed by heating.
  Compounds comprising a phosphorus atom: soaking in a molybdenum blue solution followed by rinsing with water.

Silica gel column chromatography was performed with Carlo Erba silica (silica gel 60 A, particle size: 35-70 μm). All the solvents used were distilled and rendered anhydrous before use according to the procedures described by D. D. Perrin and W. L. F. Amarego, "Purification of laboratory chemicals", 3$^{rd}$ Edition, London, 1988. The proton NMRs were recorded at ambient temperature on a Bruker AC 250 unit (at a frequency of 250 MHz), or Bruker DPX 400 unit (at a frequency of 400 MHz). The chemical displacements δ are expressed in ppm with reference to tetramethylsilane taken as the external reference. The unit is calibrated according to the $CHCL_3$ signal set at 7.24 ppm, acetone set at 2.2 ppm or water set at 4.79 ppm. The multiplicity of signals is indicated by one or more lower case letters: s (singleton), d (doublet), t (triplet), q (quadruplet), m (mass or multiplet).

The NMR spectra of carbon 13 (decoupled with reference to the proton) were recorded at ambient temperature with a Bruker DPX 400 unit (at a frequency of 100 MHz). The chemical displacements (δ) are expressed in ppm with reference to tetramethylsilane taken as the internal reference.

The NMR spectra of phosphorus 31 (decoupled with reference to the proton) were recorded at ambient temperature with a Bruker DPX 200 unit (at a frequency of 81.0 MHz). The chemical displacements (δ) are expressed in ppm with reference to 85% phosphoric acid taken as the external reference.

The mass spectra were recorded on a Jeol JMS-DX300 unit using the positive or negative FAB ionisation method. Two substances were used: G/T (1/1 v/v glycerol-thioglycerol) or NOBA (3-nitrobenzyl alcohol).

Example 1

General Allyl Alcohol Oxidation Method with Pyridinium Dichromate

To a pyridinium dichromate solution (25 mmol, 1.25 eq) in 30 ml of N,N-dimethylformamide, alcohol (20 mmol, 1 eq) is added, at −30° C. and in a nitrogen atmosphere. After 4 hours, the temperature of the medium is allowed to rise to 25° C., 100 ml of water is added, the organic phase is extracted three times with ethyl ether. The ethereal phases are collected, washed once with 1 N hydrochloric acid (100 ml), twice with water, dried on $Na_2SO_4$ and concentrated. The residual oil obtained is purified by silica gel chromatography (petroleum ether: ethyl ether) to produce colourless oils.

Example 2

(E,E)-3,7,11-Trimethyldodeco-2,6,10-trienal (1)

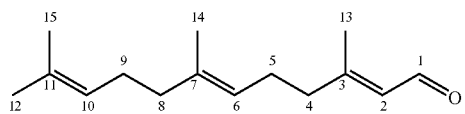

Total formula: $C_{15}H_{24}O$
Yield=71%
$R_f$=0.8 (8:2, petroleum ether:ethyl ether)
NMR $^1$H ($CDCL_3$), (ppm): 1.53 (s, 3H, $CH_3$); 1.54 (s, 3H, $CH_3$); 1.62 (s, 3H, H-14); 1.92 (m, 2H, H-9); 1.97 (m, 2H, H-9); 1.97 (m, 2H, H-5); 2.1 (s, 2H, H-8); 2.15 (m, 5H, H-4 and H-15); 4.99 (m, 1H, H-10); 5.01 (m, 1H, H-6); 5.82 (d, $J_{2-1}$ 9 Hz, 1H, H-2); 9.92 (d, 1H, H-1).
NMR $^{13}$C ($CDCL_3$), (ppm): 16.48 (1C, C-15); 18.04-18.12 (2C, C-13 and C-14); 26.08 (1C, C-12); 26.13-27.02 (2C, C-5 and C-9); 40.05-41.04 (2C, C-4 and C-8); 122.51-124.52 (2C, C-6 and C-10); 127.84 (1C, C-2); 131.93 (1C, C-11); 136.99 (1C, C-7); 164.39 (1C, C-3); 191.29 (1C, C-1).
MS FAB>0 m/z (NOBA): 221 [M+H]$^+$

Example 3

General Aldehyde Phosphonation Method

Horner-Wadsworth-Emmons Reaction:
To sodium hydride (10.06 mmol, 1 eq) in suspension in 20 ml of benzene, tetraethyl methylenediphosphonate (10.06 mmol, 1 eq) is added. Magnetic stirring is maintained for 15 min, at ambient temperature, in a nitrogen atmosphere. The aldehyde (10.06 mmol, 1 eq) is dissolved in 10 ml of benzene and added drop by drop to the reaction mixture.

After a two-hour reaction time, the mixture is taken up with dichloromethane (100 ml), washed once with water, twice with 0.1N soda and then with a saturated sodium chloride solution. After settling, the organic phase is dried on $Na_2SO_4$ and concentrated. The residual oil obtained undergoes silica gel chromatography (ethyl ether).

Example 4

(E,E,E)-4,8,12-Trimethylhexadeca-1,3,7,11-diethyl tetraenylphosphonate (2)

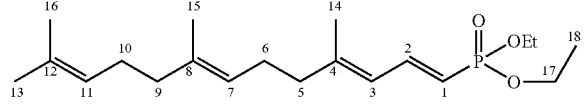

Total formula: $C_{20}H_{35}O_3P$
Yield=60%
$R_f$=0.8 (ethyl ether)
NMR $^1$H ($CDCL_3$), (ppm): 1.2 (t, $J_{18-17}$ 7.1 Hz, 6H, H-18); 1.53 (s, 6H, H-13 and H-16); 1.62 (s, 3H, H-15); 1.82 (m, 3H, H-14); 1.93 (m, 4H, H-9 and H-10); 2.1 (s, 4H, H-5 and H-6); 4.02 (q, 4H, H-17); 4.05 (m, 2H, H-7 and H-11); 5.48 (dd, $J_{1-2}$ 16.6 Hz, J1-p 20.2 Hz, 1H, H-1); 5.9 (d, $J_{3-2}$ 11.2 Hz, 1H, H-3); 7.3 (ddd, $J_{2-p}$ 21.0 Hz, 1H, H-2).
NMR $^{31}$P ($CDCL_3$), (ppm): 21.1
NMR $^{13}$C ($CDCL_2$), (ppm): 14.78-15.10 (2c, C-18); 15.17-16.13-16.45 (3C, C-14, C-15 and C-16); 24.47 (1C, C-13); 24.93-25.44 (1C, C-6 and C-10); 38.44-38.89 (2C, C-5 and C-9); 60.32-60.37 (2C, C-17); 112 (d, $J_{1-p}$ 192.2 Hz, 1C, C-1); 121.98-122.97 (2C, C-7 and C-11); 123.07 (d, $J_{3-p}$ 26.4 Hz, 1C, C-3); 130.15-134.62 (2C, C-8 and C-12); 144.21 (d, $J_{2-p}$ 6.8 Hz, 1C, C-2); 147.73 (1C, C-4).
MS FAB>0 m/z (NOBA): 377 [M+Na]$^+$; 355 [M+H]$^+$.

Example 5

General Diethyl Phosphonic Ester Deprotection Method

To diethyl phosphonic ester (2.72 mmol, 1 eq) dissolved in 30 ml of dichloromethane, pyridine (27.27 mmol, 10 eq) is added, followed by trimethylsilane bromide (13.64 mmol, 5 eq) drop by drop, at ambient temperature and in a nitrogen atmosphere. After six hours of reaction, the mixture is concentrated and 30 ml of 0.1 N soda is added.

Magnetic stirring is maintained for 30 min, the traces of pyridine are eliminated with three ether extractions and the aqueous phase is acidified to pH=2 with a 1N hydrochloric acid solution before extraction three times with ethyl ether. The ethereal phases are collected, dried on $Na_2SO_4$ and concentrated to produce a colourless oil.

Example 6

(E,E,E)-4,8,12-trimethylhexadeca-1,3,7,11-tetraenylphosphonic (3) acid

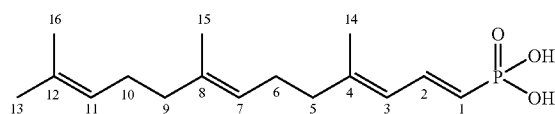

Total formula: $C_{16}H_{31}O_3P$
Yield=84%
$R_f$=0.59 (4:6, 27% ammonia:isopropanol).

NMR $^1$H (CDCl$_3$) (ppm): 1.61 (s, 3H, CH$_3$); 1.70 (s, 3H, CH$_3$); 1.83 (s, 3H, CH$_3$); 1.94-2.17 (m, 8H); 5.02-5.21 (m, 2H); 5.58-5.76 (m, 1H); 5.91 (m, 1H); 7.12-7.5 (m, 1H); 10.6 (s, 2H).

NMR $^{31}$P (CDCl$_3$) (ppm): 21.7.

NMR $^{13}$C (CDCl$_3$) (ppm): 15.66-16.43-17.70-18.11 (4C, C-13, C-14, C-15 and C-16); 26.12-27.12 (2C, C-5 and C-9); 40.10-40.54 (2C, C-6 and C-10); 119.53 (d, $J_{1-p}$ 184.5 Hz, 1C, C-1); 123.71-124.67 (2C, C-7 and C-11); 124.79 (d, $J_{3-p}$ 24.6 Hz, 1C, C-3); 131.79-136.23 (2C, C-8 and C-12); 144.33 (d, $J_{2-p}$ 5.9 Hz, 1C, C-2); 149.04 (1C, C-4).

MS FAB>0 m/z (GT): 321 [M+Na]$^+$; 293 [M+H]$^+$.

Example 7

General Phosphonic Acid Phosphorylation Conditions According to Michelson's Method Phosphonic acid (2 mmol, 1 eq) is dissolved in 20 ml of methanol, n-tributylamine (2 mmol, 1 eq) is added and the mixture is left under magnetic stirring for 30 minutes at ambient temperature. The solvent is evaporated. The resulting unprocessed product is co-evaporated with anhydrous pyridine (3×10 ml) to eliminate water traces. The phosphonic n-tributylammonium mono-salt obtained is dissolved in 18 ml of anhydrous THF. Diphenyl chlorophosphate (2 mmol, 1 eq) and n-tributylamine (6 mmol, 3 eq) are successively added. The mixture is kept under magnetic stirring at ambient temperature and in a nitrogen atmosphere for 2 hours.

In the same way, the orthophosphate n-tributylammonium mono-salt is prepared: orthophosphoric acid (6 mmol, 3 eq) is dissolved in 20 ml of methanol, n-tributylamine (6 mmol, 3 eq) is added. The solvent is evaporated after 20 minutes of magnetic stirring at ambient temperature and the traces of water are then co-evaporated with anhydrous pyridine (3×10 ml).

To the orthophosphate tributylammonium mono-salt (6 mmol, 3 eq) dissolved in 20 ml of anhydrous pyridine, activated phosphonic anhydride is slowly added (1.41 ml/hour). The mixture is kept under magnetic stirring at ambient temperature and in a nitrogen atmosphere for 15 hours, the solvents are then evaporated and the residual oil obtained undergoes silica gel chromatography (4:6, 27% aqueous ammonia:isopropanol).

Example 8

Triammonium (E,E,E)-4,8,12-Trimethylhexadeca-1,3,7,11-tetraenylpyrophosphonate (4)

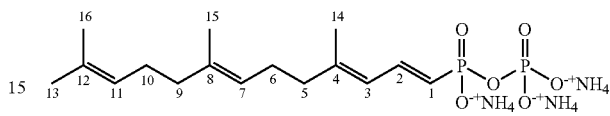

Total formula: $C_{16}H_{37}N_3O_6P_2$
Yield=49%
$R_f$=0.35 (4:6, 27% ammonia:isopropanol)

NMR $^1$H (D$_2$O), δ(ppm): 1.49 (s, 6H, 2CH$_3$); 1.56 (s, 3H, CH$_3$); 1.73 (s, 3H, CH$_3$); 1.73-2.10 (m, 8H, H-5, H-6, H-9 and H-10); 4.93-5.12 (m, 2H, H-7 and H-9); 5.5-578 (m, 1H, H-1); 5.98 (d, $J_{3-2}$ 11.0 Hz, 1H, H-3); 6.88-7.13 (m, 1H, H-2).

NMR $^{31}$P (D$_2$O$_3$), δ(ppm): −9.9 (d, $J_{β-α}$ 22.2 Hz, P-β); 8.4 (d, P-α).

NMR $^{13}$C (D$_2$O$_3$) δ(ppm): 15.87-16.75-16.89-17.48 (4C, C-13, C-14, C-15 and C-16): 25.52-26.58 (2C, C-5 and C-9); 39.59-40.03 (2C, C-6 and C-10); 120.91 (d, $J_{1-p}$ 188.9 Hz, 1C, C-1); 124.36-124.80 (2C, C-7 and C-11); 125.04 (d, $J_{3-p}$ 21.2 Hz, 1C, C-3): 132.56-136.38 (2C, C-8 and C-12); 140.52 (1C, C-2); 146.90 (1C, C-4).

MS FAB<0 m/z (GT): 377 [M-3NH$_4$+2H]$^-$.

Example 9

Tetraammonium (E,E,E)-4,8,12-trimethylhexadeca-1,3,7,11-tetraenyltriphosphonate (5)

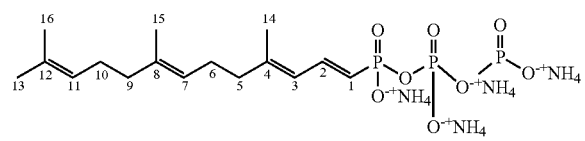

Total formula: $C_{16}H_{41}N_4O_9P_3$
Yield=18%
$R_f$=0.25 (4:6, 27% ammonia:isopropanol)

NMR $^1$H (D$_2$O), δ(ppm): 1.47 (s, 6H, 2CH$_3$); 1.54 (s, 3H, CH$_3$); 1.71 (s, 3H, CH$_3$); 1.73-2.08 (m, 8H, H-5, H-6, H-9 and H-1O); 4.9 1-5.10 (m, 2H, H-7 and H-9); 5.48-5.76 (m, 1H, H-1); 5.97 (d, $J_{3-2}$ 11.0 Hz, 1H, H-3); 6.86-7.12 (m, 1H, H-2).

NMR $^{31}$P (D$_2$O$_3$) δ(ppm): −21.3 (dd, $J_{β-α}$ 23.1 Hz, $J_{β-γ}$ 20.0 Hz, P-β); −6.3 (d, P-γ); 8.6 (d, P-α).

NMR $^{13}$C (D$_2$O$_3$) δ(ppm): 15.83-16.72-16.91-17.52 (4C, C-13, C-14, C-15 and C-16); 25.53-26.62 (2C, C-5 and C-9); 39.59-40.09 (2C, C-6 and C-10); 120.99 (d, $J_{1-p}$ 189.2 Hz, 1C, C-1); 124.34-124.81 (2C, C-7 and C-11); 125.14 (d, $J_{3-p}$ 22.3 Hz, 1C, C-3); 132.40-136.43 (2C, C-8 and C-12); 140.58 (1C, C-2); 146.92 (1C, C-4).

MS FAB<0 m/z (GT): 457 [M-4NH$_4$+3H]$^-$.

Example 10

General Protection Method of Alcohols in THP Ether Form

To pyridinium p-toluenesulphonate (9.84 mmol, 0.1 eq) dissolved in 20 ml of dichloromethane, alcohol (98.45 mmol, 1 eq) and 1,2-dihydropyrane (147.68 mmol, 1.5 eq) are added. The reaction mixture is kept under magnetic stirring, at ambient temperature and in a nitrogen atmosphere for four hours. The mixture is taken up with ethyl ether (50 ml), washed three times with water, dried on concentrated $Na_2SO_4$ and undergoes silica gel chromatography (3:7, ethyl ether: petroleum ether) to produce an oil.

Example 11

3-Methyl-1-tetrahydropyranyl-2'-oxy-but-2-ene (6)

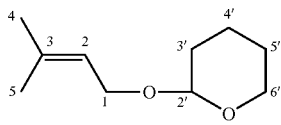

Total formula $C_{10}H_{18}O_2$
Yield=100%
$R_f$=0.75 (3:7, ethyl ether:petroleum ether)
NMR $^1$H (CDCl$_3$), δ(ppm): 1.40-1.90 (m, 6H, H-3', H-4' and H-5'); 1.50 (s, 3H, CH$_3$); 1.65 (s, 3H, CH$_3$); 3.40-3.50 (m, 1H, H-6'); 3.72-3.82 (m, 1H, H-6'); 3.86-3.97 (dd, $J_{1a-1b}$ 11.7 Hz, $J_{1a-2}$ 7.7 Hz, 1H, H-1a); 4.08-4.21 (dd, $J_{1b-2}$ 6.6 Hz, 1H, H-1b); 4.50 (m, 1H, H-2'); 5.30 (m, 1H, H-2).
MS FAB>0 m/z (NOBA): 171 [M+H]$^+$.

Example 12

(E)-3,7-Dimethyl-1-tetrahydropyranyl-2'-oxy-octa-2,6-diene (7)

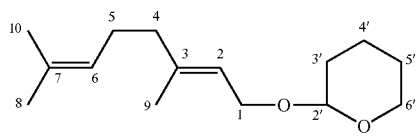

Total formula $C_{15}H_{26}O_2$
Yield=99%
$R_f$=0.75 (3:7, ethyl ether:petroleum ether)
NMR $^1$H (CDCl$_3$), δ(ppm): 1.40-1.90 (m, 6H, 2H-3', 2H-4' and 2H-5'); 1.55 (s, 3H, CH$_3$); 1.64 (s, 6H, 2CH$_3$); 1.90-2.10 (m, 4H, 2H-4 and 2H-5); 4.45 (m, 1H, H-2'); 3.85 (m, 1H, H-2'); 4.0 (dd, $J_{1a-1b}$ 11.8 Hz, $J_{1a-2}$ 7.3 Hz, 1H, H-1a); 4.25 (dd, $J_{1b-2}$ 6.4 Hz, 1H, H-1b); 4.57 (m, 1H, H-25); 5.04 (t, $J_{6-5}$ 6.9 Hz, 1H, H-6); 5.30 (dd 1H, H-2).
MS FAB>0 m/z (NOBA): 239 [M+H]$^+$.

Example 13

General Oxidation Method in Allyl Position

A 70% aqueous tert-butyl hydroperoxide solution (17.13 ml, 177 mmol, 3 eq) is added to selenium dioxide (5.31 mmol, 0.09 eq) in suspension in 20 ml of dichloromethane, at ambient temperature. After 30 min, the compound 6 or 7 (59 mmol, 1 eq) is added drop by drop and magnetic stirring is maintained at 25° C. for 48 hours. The mixture is then taken up with 20 ml of toluene, concentrated and dissolved in 50 ml of ether. The organic phase is washed four times with 10% soda, once with a saturated sodium chloride solution, dried on $Na_2SO_4$ and concentrated. The residue obtained undergoes silica gel chromatography (4:6, ethyl ether: petroleum ether) to produce:

Example 14

(E)-2-Methyl-4-tetrahydropyranyl-2'-oxy-but-2-enol (8)

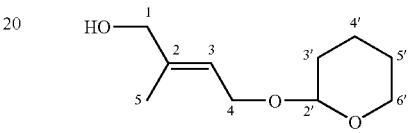

Total formula: $C_{10}H_{18}O_3$
Yield=38%
$R_f$=0.26 (4:6, ethyl ether:petroleum ether)
NMR $^1$H (CDCl$_3$), δ(ppm): 1.40-1.86 (m, 6H, H-3', H-4 and H-5'); 1.75 (s, 3H, CH$_3$); 3.50-3.60 (m, 1H, H-6'); 3.85 (m, 1H, H-6'); 4.08 (s, 2H, H-1); 4.10 (dd, $J_{4a-4b}$ 12.1 Hz, $J_{4a-3}$ 7.9 Hz, 1H, H-4a); 4.33 (dd, $J_{4b-3}$ 6.4 Hz, 1H, H-4-b); 4.67 (m, 1H, H-2'); 5.68 (m, 1H, H-3).
MS FAB>0 m/z (NOBA): 187 [M+H]$^+$.

Example 15

(E,E)-2,6-Dimethyl-8-tetrahydropyranyloxy-octa-2,6-dienol (9)

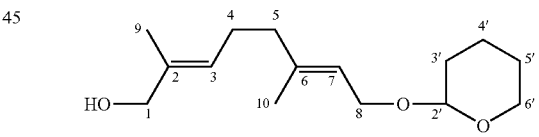

Total formula: $C_{15}H_{26}O_3$
Yield=47%
$R_f$=0.35 (1:1, ethyl ether:petroleum ether)
NMR $^1$H (CDCl$_3$), δ(ppm): 1.45-1.90 (m, 6H, H-4H-5' and H-6'); 1.70 (s, 6H, 2CH$_3$); 1.74 (s, 3H, CH$_3$); 2.02-2.36 (m, 4H, H-4 and H-5); 3.45-3.60 (m, 1H, H-3'); 3.85-4.0 (m, 1H, H-3'); 4 (s, 2H, H-1); 4.0-4.12 (dd, $J_{8a-7}$ 7.3 Hz $J_{8a-8b}$ 11.4 Hz, 1H, H-8a); 4.15-4.28 (dd, $J_{8b-7}$ 6.4 Hz, 1H, H-8b); 4.55-4.62 (m, 1H, H-2'); 5.30-5.46 (m, 2H, H-7 and H-3).
NMR $^{13}$C (CDCl$_3$), (ppm): 13.6-16.3 (2C, C-9 and C-10); 19.5 (1C, C-4'); 25.4-25.7 (2C, C-4 and C-5'); 30.6 (1C, C3'); 39.1 (1C, C-5): 62.2 (1C, C-8); 63.6 (1C, C-6); 68.5 (1C, C-1); 97.7 (10, C-2'); 1 (2C, C-3 and C-7); 135.1-139.8 (2C, C-2 and C-6).
MS FAB>0 m/z (NOBA): 255 [M+H]$^+$.

Example 16

(E)-2-Methyl-4-tetrahydropyranyl-2'-oxy-but-2-enal (10)

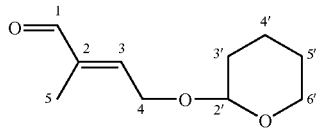

Total formula: $C_{10}H_{16}O_3$
Yield=12%
$R_f$=0.66 (1:1, ethyl ether:petroleum ether).

NMR $^1$H (CDCl$_3$), δ(ppm): 1.40-1.85 (m, 6H, H-3', H-4' and H-5); 1.78 (s, 3H, CH$_3$); 3.50-3.63 (m, 1H, H-6'); 3.80-4.0 (m, 1H, H-6'); 4.37 (dd, $J_{4a-4b}$ 15.3 Hz, $J_{4a-3}$ 5.9 Hz, 1H, R-4a); 4.61 (dd, $J_{4b-3}$ 5.4 Hz, 1H, H-4b); 4.71 (m, 1H, H-2'); 6.63 (m, 1H, H-3); 9.47 (s, 1H, H-1).

Example 17

(E,E)-2,6-Dimethyl-8-tetrahydropyranyl-2'-oxy-octa-2,6-dienal (11)

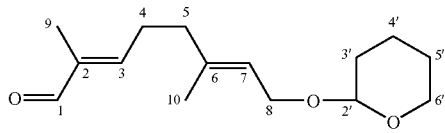

Total formula: $C_{15}H_{24}O_2$
Yield=11.3%
$R_f$=0.62 (1:1, ethyl ether:petroleum ether).

NMR $^1$H (CDCl$_3$), δ(ppm): 1.40-1.70 (m, 6H, H-4', H-5' and H-6'); 1.72 (s, 3H, CH$_3$); 1.75 (s, 3H, CH$_3$); 2.20 (t, $J_{5-4}$ 7.5 Hz, 2H, H-5); 2.40-2.60 (td, $J_{4-3}$ 7.2 Hz, 2H, H-4); 3.40-3.60 (m, 1H H-3'); 3.82-3.98 (m, 1H, H-3'); 4.05 (dd, $J_{8a-8b}$ 12.0 Hz, $J_{8a-7}$ 7.4 Hz, 1H, H-8a); 4.30 (dd, $J_{8b-7}$ 6.3 Hz, 1H, H-8b); 4.62 (m, 1H, H-2'); 5.42 (in, 1H, H-7); 6.50 (t, 1H, H-3); 9.40 (s, 1H, H-1).

Example 18

General Coupling Method of Alcohols 8 and 9 with 4-Bromomethyl Benzophenone

To sodium hydride (8.87 mmol, 1.1 eq) in suspension in 30 ml of anhydrous THF, alcohol 8 or 9 (8.07 mmol, 1 eq) is added, at ambient temperature, in a nitrogen atmosphere. The reaction mixture is then reflux-heated and kept under magnetic stirring for 30 min. 4-bromomethyl benzophenone (8.87 mmol, 1.1 eq) in solution in 15 ml of anhydrous THF is added. After 3 hours of reaction in a THF reflux, the temperature of the medium is returned to 25° C., 100 ml of water is added and the organic phase extracted three times with ethyl ether. The ethereal phases are collected, washed once with a saturated sodium chloride solution, dried on Na$_2$SO$_4$, concentrated and undergo silica gel chromatography (4:6, ethyl ether: petroleum ether) to produce colourless oils.

Example 19

(E)-[4-(2'-Methyl-4'-tetrahydropyranyl-2"-oxy-but-2'-enyloxy-methyl)-phenyl]-phenyl-methanone (12)

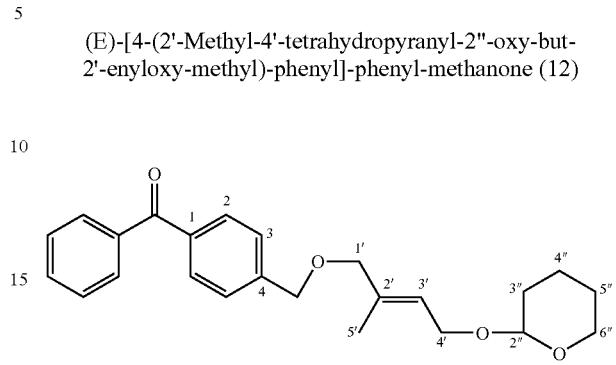

Total formula: $C_{24}H_{28}O_4$
Yield=36%
$R_f$=0.4 (4:6, ethyl ether:petroleum ether).

NMR $^1$H (CDCl$_3$), δ(ppm): 1.50-1.78 (m, 6H, H-3", H-4" and H-5"); 1.77 (s, 3H, CH$_3$); 3.48-3.60 (m, 1H, H-6"); 3.88-4.0 (m, 1H, H-6"); 4.02 (s, 2H, H-1'); 4.11 (dd, $J_{4a-4b}$ 12.3 Hz, $J_{4a-3}$ 7.1 Hz, 1H, H-4a); 4.87 (dd, $J_{4b-3'}$ 6.3 Hz, 1H, H-4b); 4.59 (s, 2H, OCH$_2$-benzyl); 4.67 (m, 1H, H-2"); 5.72 (m, 1H, H-3').

NMR $^{13}$C (CDCl$_3$), δ(ppm): 14.50 (1C, C-5'); 19.52 (1C, C-4"); 25.32 (C, C-5"); 30.60 (1C, C3"); 62.12 (1C, C-4'); 63.52 (1C, C-6"); 71.77 (1C, OCH$_2$-benzyl); 76.19 (1C, C-1'); 97.81 (1C, C-2"); 126.90 (1C, C-3'); 127.57-127.67 (2C, C-ar); 130.45-130.52 (2C, C-ar); 130.72-130.77 (2C, C-ar); 132.85 (1C, C-ar); 135.73-137.23 (C, C-1 and C-ar); 138.09-143.63 (2C, C-4 and C-2'); 196.93 (1C, C-ketone).
MS FAB>0 m/z (NOBA): 381 [M+H]$^+$.

Example 20

(E,E)-[4-(2',6'-Dimethyl-8'-tetrahydropyranyl-2"-oxy-octa-2',6'-dienyloxy)-methylphenyl]-phenyl-methanone (13)

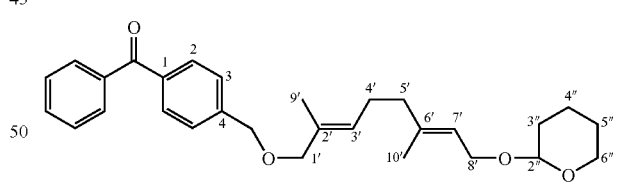

Total formula: $C_{29}H_{36}O_4$
Yield=49%
$R_f$=0.66 (4:6, ethyl ether:petroleum ether).

NMR $^1$H (CDCl$_3$), δ(ppm): 1.50-1.90 (m, 6H, H-3", H and H-5"); 1.70 (s, 6H, H-9' and H-10'); 2.10-2.30 (m, 4H, H-4 and H-5'); 3.50-3.62 (m, 1H, H-6"); 3.85-3.95 (m, 1H, H-6"); 3.95 (s, 2H, H-1); 4.06 (dd, $J_{8'a-8'b}$ 11.9 Hz, $J_{8'a-7}$ 7.4 Hz, 1H, H-8' a); 4.27 (dd, $J_{8'b-7}$ 6.5 Hz, 1H, H-8' b); 4.55 (s, 2H, OCH$_2$-benzyl); 4.64 (m, 1H, H-2"); 5.35-5.50 (m, 2H, H-3 and H-7'); 7.40-7.60 (m, 4H, H-ar); 7.55-7.65 (m, 1H, H-ar); 7.80-7.90 (m, 4H, H-ar).

NMR $^{13}$C (CDCl$_3$), δ(ppm): 13.8-16.2 (2C, C-9' and C-10'); 19.5 (1C, C-4"); 25.3-25.8 (2C, C-4' and C-5"); 30.6 (1C, C3"); 39.0 (1C, C-5'); 62.0 (1C, C-8'); 63.5 (1C, C-6");

70.6-76.3 (2C, C-1' and OCH$_2$-benzyl); 97.7 (1C, C-2'''); 120.9-127.1 (2C, C-3' and C-7'); 128.3-128.9-129.8-131.4-132.2 (9C, C-ar); 132.2 (1C, C-6'); 137.5 (1C, C-ar); 137.9 (1C, C-1); 138.9 (1C, C-2'); 139.4 (1C, C-4); 196.3 (1C, C-ketone).

MS FAB>0 m/z (NOBA): 449 [M+H]$^+$.

Example 21

General THP Group Deprotection Method

A solution of compound 12 or 13 (5.26 mmol, 1 eq) and pyridinium p-toluenesulphonate (0.48 mmol, 0.09 eq) in 40 ml of methanol is kept under magnetic stirring, in a reflux for three hours. The reaction mixture is then concentrated and undergoes silica gel chromatography (1:1, ethyl ether: petroleum ether) to produce colourless oils.

Example 22

(E)-[4-(2'-Methyl-4'-hydroxy-but-2'-rnyloxymethyl)-phenyl]-phenyl-methanone (14)

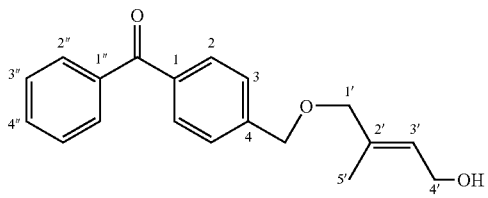

Total formula: C$_{19}$H$_{20}$O$_3$
Yield=100%
R$_f$=0.6 (1:1, ethyl ether:petroleum ether).

NMR $^1$H (CDCl$_3$), δ(ppm): 1.62 (s, 3H, CH$_3$); 3.87 (s, 2H, H-1'); 4.18 (d, J$_{3'-4'}$ 6.6 Hz, 1H, H-3'); 4.46 (s, 2H, OCH$_2$-benzyl); 5.61 (t, 1H, H-4'); 7.26-7.40 (m, 4H, H-ar); 7.42-7.35 (m, 1H, H-ar); 7.57-7.72 (m, 4H, H-ar).

NMR $^{13}$C (CDCl$_3$), δ(ppm): 14.49 (1C, C-5'); 59.50 (1C, C-4'); 71.74 (1C, OCH2-benzyl); 76.18 (1C, C-1'); 126.89 (1C, C-3'); 127.58-127.66 (2C, C-ar); 128.71-128.82 (2C, C-ar); 130.45 (2C, C-ar); 130.71-130.76 (2C, C-ar); 132.84 (1C, C-ar); 135.73-137.22 (C, C-1 and C-ar); 138.07-143.60 (2C, C-4 and C-2'); 196.92 (1C, C-ketone).

MS FAB>0 m/z (NOBA): 297 [M+H]$^+$.

Example 23

(E,E)-[4-(8-Hydroxy-2',6'-dimethyl-octa-2',6-dienyloxymethyl)-phenyl]-methanone (15)

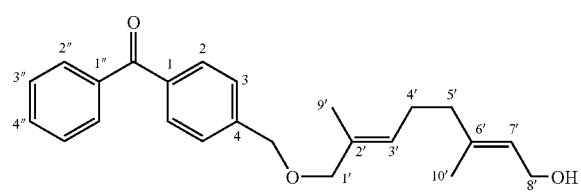

Total formula: C$_{24}$H$_{28}$O$_3$
Yield=100%
R$_f$=0.3 (1:1, ethyl ether:petroleum ether).

NMR $^1$H (CDCl$_3$), δ(ppm): 1.62 (s, 6H, H-9' and H-10'); 2.10-2.30 (m, H-4' and H-5'); 3.95 (s, 2H, H-1'); 4.20 (d, J$_{8'-7'}$ 6.9 Hz, 2H, H-8'); 4.55 (s, 2H, OCH$_2$-benzyl); 5.45 (t, J$_{3'-4'}$ 60.9 Hz, 1H, H-3'); 5.46 (t, 1H, H-7'); 7.40-7.54 (m, 4H, H-ar); 7.55-7.66 (m, 1H, H-ar); 7.75-7.90 (m, 4H, H-ar).

NMR $^{13}$C (CDCl$_3$), δ(ppm): 13.8 (1C, C-9'); 16.0 (1C, C-10'); 25.8 (C-4'); 38.9 (1C, C-5'); 59.1 (1C, C-8'); 70.7-76.2 (2C, C-1' and OCH$_2$-benzyl); 123.7 (1C, C-3'); 127.9-128.1 (2C, C-ar); 128.6 (1C, C-7'); 128.9-129.1 (2C, C-ar); 129.9 (2C, C-ar); 131.5 (2C, C-ar); 132.0 (1C, C-6'); 132.3 (1C, C-ar); 137-4-137.5 (2C, C-1 and C1''); 138.7-138.9 (2C, C-2'' and C-4); 196.5 (1C, C-ketone).

MS FAB>0 m/z (NOBA): 365 [M+H]$^+$.

Example 24

ϵ-3-Methyl-4-(4'-benzoylbenzyloxy)-but-2-enal (16)

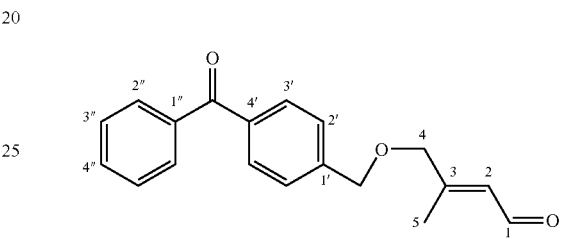

Total formula: C$_{19}$H$_{18}$O$_3$
Yield=70%
R$_f$=0.5 (1:1, ethyl ether:petroleum ether).

NMR $^1$H (CDCl$_3$), δ(ppm): 2.15 (d, J$_{5-2}$ 1.4 Hz, 3H, H-5); 4.1 (s, 2H, H-4); 4.62 (s, 2H, OCH$_2$-benzyl); 6.21 (dq, J$_{2-1}$ 8.0 Hz, 1H, H-2); 7.42-7.55 (m, 4H, H-ar); 7.55-7.66 (m, 1H, H-ar); 7.78-7.86 (m, 4H, H-ar); 10.08 (d, 1H, H-1).

NMR $^{13}$C (CDCl$_3$), δ(ppm): 14.88 (1C, C-5); 72.56 (1C, C-4); 74.23 (1C, OCH$_2$-benzyl); 126.15 (1C, C-2); 127.52 (2C, C-ar); 128.69 (2C, C-ar); 130.4 (2C, C ar); 130.72 (2C, C-ar); 132.75 (1C, C-ar); 137.47 (1C, C-1''); 137.92 (1C, C-4'); 142.67 (1C, C-1'); 152.42 (1C, C-3); 191.3 (1C, C-1); 196.69 (1C, C-ketone).

MS FAB>0 m/z (NOBA): 295 [M+H]$^+$.

Example 25

(E,E)-3,7-Dimethyl-8-(4'-benzoylbenzyloxy)-octa-2,6-dienal (17)

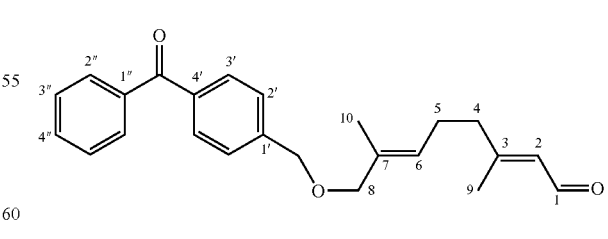

Total formula: C$_{24}$H$_{26}$O$_3$
Yield=70%
R$_f$=0.55 (7:3, ethyl ether:petroleum ether).

NMR $^1$H (CDCl$_3$), δ(ppm): 1.60 (s, 3H, CH$_3$); 1.73 (s, 3H, CH$_3$); 2.98-2.38 (m, 4H, H-4 and H-5); 3.97 (s, 2H, H-8); 4.56 (s, 2H, OCH2-benzyl); 5.45 (m, 1H, H-6); 5.92 (d, J$_{2-1}$ 7.9 Hz, 1H, H-2); 7.45-7.56 (m, 4H, H-ar); 7.57-7.68 (m, 1H, H-ar); 7.78-7.88 (m, 4H, H-ar); 10.02 (d, 1H, H-1).

NMR $^{13}$C (CDCl$_3$), δ(ppm): 14.41 (1C, C-9); 18.10 (1C, C-10); 25.73 (1C, C5); 40.54 (1C, C-4); 71.45 (1C, C-8); 76.71 (1C, OCH$_2$-benzyl); 126.78 (1C, C-2); 127.20 (2C, C-ar); 127.55 (1C, C-6); 128.69 (2C, C-ar); 130.71 (2C, C-ar); 130.84 (2C, C-ar); 132.83 (1C, C-4"); 133.82 (1C, C-7); 137.16 (1C, C-1"); 138.08 (1C, C-4'); 143.85 (1C, C-1'); 163.78 (1C, C-3); 191.62 (1C, C-1); 196.96 (1C, C-ketone).

MS FAB>0 m/z (NOBA): 363 [M+H]$^+$.

Example 26

(E,E)-[4-(5'-Diethylphosphono-2''-methyl-penta-2,4-dienyloxymethyl)]-phenyl-methanone (18)

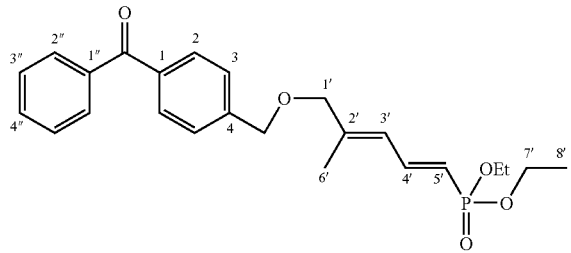

Total formula: C$_{24}$H$_{29}$O$_5$P
Yield=95%
R$_f$=0.5 (ethyl acetate).

NMR $^1$H (CDCl$_3$), δ(ppm): 1.34 (t, J$_{8'-7'}$ 6.9 Hz, 6H, H-8'); 1.92 (s, 3H, CH$_3$); 4.06 (s, 2H, H-1'); 4.08-4.28 (q, 4H, H-7'); 4.60 (s, 2H, OCH$_2$-benzyl); 5.70 (dd, J$_{5'-P}$ 19.5 Hz, J$_{5'-4'}$ 16.9 Hz, 1H, H-5'); 6.26 (d, J$_{3'-4'}$ 11.6 Hz, 1H, H-3'); 7.30-7.65 (m, 6H, H4' and 5H-ar); 7.60-7.88 (m, 4H, H-ar)

NMR $^{31}$P (CDCl$_3$), δ(ppm): 209.

NMR $^{13}$C (CDCl$_3$), δ(ppm): 16.70 (1C, C-6') 16.81 (2C, C-8'); 63.15 (2C, C-7'); 72.15 (1C, C-1'); 75.32 (1C, OCH$_2$-benzyl); 117.18 (d, J$_{5'-P}$ 191.4 Hz, 1C, C-5'); 175.13 (d, J$_{3'-P}$ 26.9 Hz, 1C, C-3'); 127.54 (2C, C-ar); 128.72 (2C, C-ar); 130.50 (2C, C-ar); 130.74 (2C, C-ar); 132.88 (1C, C-4"); 137.37 (1C, C-1"); 138.02 (1C, C-1); 143.20 (1C, C-4); 143.99 (1C, C-25); 144.53 (d, J$_{4'-P}$ 6.7 Hz, 1C, C-4'); 196.82 (1C, C-carbonyl).

MS FAB>0 m/z (NOBA): 451 [M+Na]$^+$; 429 [M+H]$^+$.

Example 27

(E,E,E)-[4-9'Diethylphosphono-2',6-dimethyl-octa-2',6',8'-trienyloxymethyl)-phenyl]-phenyl-methanone (19)

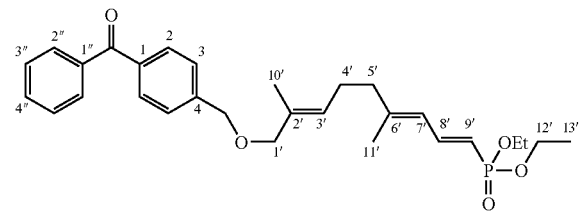

Total formula: C$_{29}$H$_{34}$O$_5$P
Yield=75%
R$_f$=0.6 (ethyl acetate).

NMR $^1$H (CDCl$_3$), δ(ppm): 1.24 (t, J$_{13'-12'}$ 7.0 Hz, 6H, H-13'); 1.73 (s, 3H, CH$_3$); 1.91 (s, 3H, CH$_3$); 2.20-2.30 (m, 4H, 2H-4' and 2H-5'); 3.97 (s, 2H, H-1'); 4.09 (q, 4H, H-12'); 4.55 (s, 2H, OCH$_2$-benzyl); 5.45 (m, 1H, H-3'); 5.59 (dd, J$_{9'-P}$ 20.2 Hz, J$_{9'-8'}$ 16.2 Hz, 1H, H-9'); 5.99 (d, J$_{7'-8'}$ 12.1 Hz, 1H, H-7'); 7.32-7.65 (Cm, 1H, H-8'); 7.46-7.65 (m, 5H, H-ar); 7.76-7.90 (m, 4H, H-ar).

NMR $^{31}$P (CDCl$_3$), δ(ppm): 21.7.

NMR $^{13}$C (CDCl$_3$), δ(ppm): 14.41 (1C, C-10'); 16.78 (2C, C-13'); 17.75 (C-11'); 26.32 (1C, C-4'); 40.11 (1C, C-5'); 62 (2C, C-12'); 71.31 (1C, C-1'); 76.91 (1C, OCH$_2$-benzyl); 114.94 (d, J$_{9'-P}$ 192.2 Hz, 1C, C-9'); 124.94 (d, J$_{7'-P}$ 26.6 Hz, 1C, C-7'); 127.61 (2C, C-ar) 127.83 (1C, C-3'); 128.69 (2C, C-ar); 130.44 (2C, C-ar) 130.69 (2C, C-ar); 132.80 (1C, C-4"); 133.12 (1C, C-2); 137.16 (1C, C-1"); 138.11 (1C, C-1); 143.84 (10, C-4); 145.52 (d, J$_{8'-P}$ 6.6 Hz, 1C, C-8'); 148.66 (1C C-6'); 196.89 (1C, C-carbonyl).

MS FAB>0 m/z (NOBA): 519 [M+Na]$^+$; 497 [M+H]$^+$.

Example 28

(E,E)-4-[(5'-Phosphono-6' methyl-penta-2',4'-dienyloxymethyl)-phenyl-phenyl]-methanone (20)

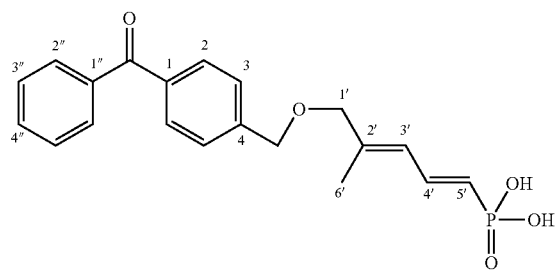

Total formula: C$_{20}$H$_{21}$O$_5$P
Yield=70%
R$_f$=0.56 (4:6, 27% ammonia:isopropanol).

NMR $^1$H (CDCl$_3$), δ(ppm): 1.91 (s, 3H, CH$_3$); 4.06 (s, 2H, H-1'); 4.60 (s, 2H, OCH$_2$-benzyl); 5.80 (dd, J$_{5'-P}$ 21.1 Hz, J$_{5'-4'}$ 16.6 Hz, 1H, H-5'); 6.25 (d, J$_{3'-4'}$ 11.4 HZ, 1H, H-3'); 7.35-7.60 (m, 6H, H4' and 5H-ar); 7.72-7.88 (m, 4H, H-ar); 10.25 (s, 2H, POH).

NMR $^{31}$P (CDCl$_3$), δ(ppm): 23.6.

NMR $^{13}$C (CDCl$_3$), δ(ppm): 15.23 (1C, C-6'); 72.06 (1C, C-1'); 75.35 (1C, OCH2-benzyl); 118.59 (d, J$_{5'-P}$ 188.5 Hz, 1C, C-5'); 126.65 (d, J$_{3'-P}$ 26.6 Hz, 1C, C-3'); 127.55 (2C, C-ar); 128.71 (2C, C-ar); 130.44 (2C, C-ar); 130.74 (2C, C-ar); 132.84 (1C, C-4"); 134.50 (1C, C-1"); 135.0 (1C, C-1); 137.36 (d, J$_{4'-P}$ 6.1 Hz, 1C, C-4') 143.19 (1C, C-4) 144.0 (1C, C-2'); 198.0 (1C, C-carbonyl).

MS FAB>0 m/z (NOBA): 395 [M+Na]$^+$; 373 [M+H]$^+$.

Example 29

(E,E,E)-[4-(9'-Phosphono-2'6'-dimethyl-nona-2',6', 8'-trienyloxymethyl)-phenyl]-phenyl-methanone (21)

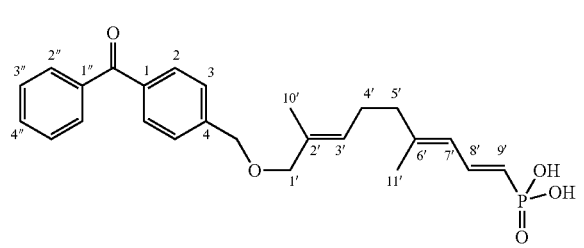

Total formula: $C_{25}H_{28}O_5P$

Yield=85%

$R_f$=0.5 (4:6, 27% ammonia:isopropanol).

NMR $^1$H (CDCl$_3$), δ(ppm): 1.72 (s, 3H, CH$_3$); 1.86 (s, 3H, CH$_3$); 2.12-2.30 (m, 4H, H-4' and H-5'); 3.96 (s, 2H, H-1'); 4.54 (s, 2H, OCH$_2$-benzyl); 5.45 (m, 1H, H-3'); 5.66 (dd, J$_{9'-P}$ 20.6 Hz, J$_{9'-8'}$ 16.8 Hz, 1H, H-9'); 5.95 (d, J$_{7'-8'}$ 10.9 Hz, 1H, H-7'); 7.35-7.60 (m, 1H, H-8'); 7.40-7.68 (m, 5H, H-ar); 7.75-7.88 (m, 4H, H-ar).

NMR $^{31}$P (CDCl$_3$), δ(ppm): 24.4.

NMR $^{13}$C (CDCl$_3$), δ(ppm): 14.39 (1C, C-10'); 16.80 (1C, C-11'); 26.21 (1C, C-4'); 40.10 (1C, C-5'); 71.20 (10, C-9'); 76.88 (1C, OCH$_2$-benzyl); 114.89 (d, J$_{9'-P}$ 190 Hz, 1C, C-9); 124.93 (d, J$_{7'-P}$ 26.3 Hz, 1C, C-7'); 127.58 (2C, C-ar); 127.80 (1C, C-3'); 128.67 (7C, C-ar); 130.47 (2C, C-ar); 130.71 (2C, C-ar); 132.81 (1C, C-4"); 133.06 (1C, C-2'); 137.04 (1C, C-1"); 138.0 (1C, C-1'); 143.80 (1C, C-4); 145.46 (d, J$_{8'-P}$ 6.6 Hz, 1C, C-8'); 148.69 (1C, C-6'); 196.77 (1C, C-carbonyl).

MS FAB>0 m/z (NOBA): 463 [M+Na]$^+$; 441 [M+H]$^+$.

Example 30

(E,E)-4-[(5'-Pyrophosphono-6'-methyl-penta-2',4'-dienyloxymethyl)-phenyl]-methanone (22)

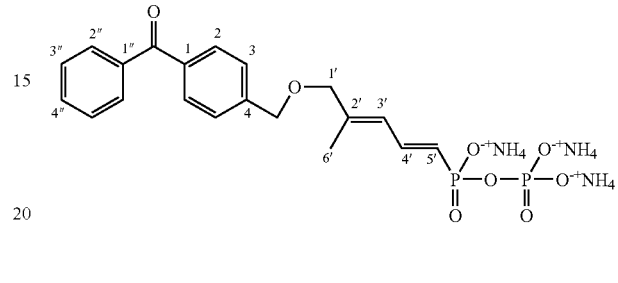

Total formula: $C_{20}H_{31}N_3O_8P_2$

Yield=48%

$R_f$=0.35 (4:6, 27% ammonia:isopropanol).

NMR $^1$H (D$_2$O), δ(ppm): 1.64 (s, 3H, CH$_3$); 4.0 (s, 2H, H-1'); 4.51 (s, 2H, OCH$_2$-benzyl); 5.90 (dd, J$_{5'-P}$ 19.2 Hz, J$_{5'-4'}$ 16.81 Hz, 1H, H-5'); 6.13 (d, J$_{3'-4'}$ 10.9 Hz, 1H, H-3'); 7.10 (ddd, J$_{4'-P}$ 20.4 Hz, 1H, H-4'); 7.35-7.50 (m, 4H, H-ar); 7.54-7.62 (m, 1H, H-ar); 7.62-7.74 (m, 4H, H-ar).

NMR $^{31}$P (D$_2$O), δ(ppm): −7.16 (d, J$_{β-α}$ 23.0 Hz, P-β); 6.54 (d, P-α).

NMR $^{13}$C (D$_2$O), δ(Ppm): 14.33 (1C, C-6'); 71.22 (1C, C'); 75.62 (1C, OCH$_2$-benzyl); 124.53 (d, J$_{5'-P}$ 185.0 Hz, 1C, C-5"); 127.48 (d, J$_{3'-P}$ 26.2 Hz, 1C, C-3'); 128.19 (2C, C-ar); 128.84 (2C, C-ar); 130.74 (2C, C-ar); 130.88 (2C, C-ar); 133.82 (1C, C-4"); 136.40 (1C, C-1"); 136.88 (1C, C-1); 138.83 (d, J$_{4'-P}$ 5.7 Hz, 1C, C-4'); 140.9 (1C, C-4); 143.40 (1C, C-2'); 200.37 (1C, C-carbonyl).

MS FAB>0 m/z (GT): 463 [M+2NH$_4$+3H]$^+$; 441 [M+3NH$_4$+4H]$^+$.

Example 31

(E,E,E)-[4-(9'-Pyrophosphono-2',6'-Dimethyl-nona-2',6',8'-trienyloxymethyl)-phenyl]-phenyl-methanone (23)

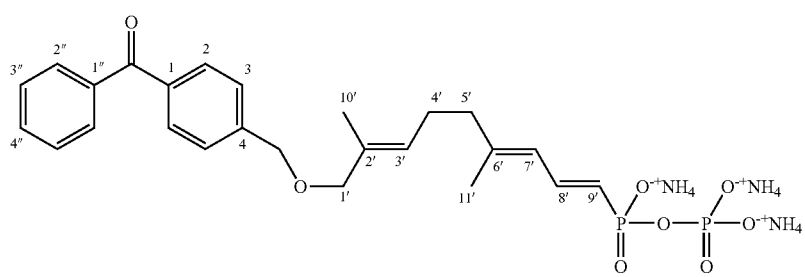

Total formula: $C_{25}H_{39}N_3O_8P_2$
Yield=57%
$R_f$=0.35 (4:6, 27% ammonia:isopropanol).
NMR $^1$H (D$_2$O), δ(ppm): 1.51 (s, 3H, CH$_3$); 1.72 (s, 3H, CH$_3$); 1.95-2.15 (m, 4H, H-4', H-5'); 3.80 (s, 2H, H-1'); 4.40 (s, 2H, OCH$_2$-benzyl); 5.23-5.35 (m, 1H, H-3'); 5.78 (dd, $J_{9'-P}$ 19.7 Hz, $J_{9'-8'}$ 16.8 Hz, 1H, H-9'); 5.90 (d, $J_{7'-8'}$ 11.1 Hz, 1H, H-7'); 7.04 (ddd, $J_{8'-P}$ 20.5 Hz, 1H, H-8'); 7.28-7.46 (m, 4H, Har); 7.51-7.63 (m, 5H, H-ar).

NMR $^{31}$P (D$_2$O), δ(ppm): −6.45 (d, $J_{β-α}$ 23.22 Hz, P-β); 7.14 (d, P-α).

NMR $^{13}$C (D$_2$O), δ(ppm): 13.67 (1C, C-10'); 16.75 (1C, C-11'); 25.97 (1C, C-4'); 39.27 (1C, C-5'); 70.46 (1C, C-1'); 76.47 (1C, OCH$_2$-benzyl); 121.43 (d, $J_{9'-P}$ 187.1 Hz, 1C, C-9'); 124.91 (d, $J_{7'-P}$ 26.1 Hz, 1C, C-7'); 128 (2C, C-ar); 128.84 (2C, C-ar); 130.34 (2C, C-ar); 130.73 (2C, C-ar); 129.53 (1C, C-3'); 132.20 (1C, C-4'); 133.65 (1C, C-2'); 136.35 (1C, C-1"); 137.04 (1C, C-1"); 140.13 (1C, C-4); 143.85 (d, $J_{8'-P}$ 5.6 Hz, 1C, C-8'); 146.41 (1C, C-6'); 199.35 (1C, C-carbonyl).

MS FAB>0 m/z (GT): 538 [M+2NH$_4$+3H]$^+$; 521 [M+3NH$_4$+4H]$^+$.

Example 32

(E,E)-4-[(5')-Triphosphono-6'-methyl-penta-2',4'-dienyloxymethyl)-phenyl]-methanone (24)

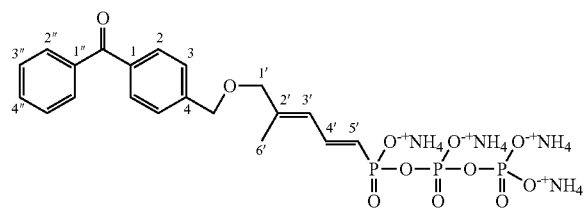

Total formula: $C_{20}H_{35}N_4O_{11}P_3$
Yield=6%
$R_f$=0.15 (4:6, 27% ammonia:isopropanol).
NMR $^1$H (D$_2$O), δ(ppm): 1.79 (s, 3H, CH$_3$); 4.03 (s, 2H, H-1'); 4.54 (s, H, OCH$_2$-benzyl); 5.92 (dd, $J_{5'-P}$ 19.9 Hz, $J_{5'-4'}$ 16.6 Hz, 1H, H-5'); 6.14 (d, $J_{3'-4'}$ 11.1 Hz, 1H, H-3'); 7.17 (ddd, $J_{4'-P}$ 20.0 Hz, 1H, H-4'); 7.30-7.50 (m, 4H, H-ar); 7.52-7.68 (m, 5H, H-ar).

NMR $^{31}$P (D$_2$O), δ(ppm): −22.0 (dd, $J_{β-α}$ 23.1 Hz, $J_{β-γ}$ 19.9 Hz, P-β); −7.6 (d, P-γ); 9.5 (d, P-α).

NMR $^{13}$C (D$_2$O), δ(ppm): 14.34 (1C, C-6'); 71.28 (1C, C-1'); 75.65 (1C, OCH$_2$-benzyl); 123.58 (d, $J_{5'-P}$ 186.0 Hz, 1C, C-5'); 127.44 (d, $J_{3'-P}$ 26.8 Hz, 1C, C-3'); 128.41 (2C, C-ar); 128.87 (2C, C-ar); 130.62 (2C, C-ar); 131.01 (2C, C-ar); 133.84 (1C, C-4"); 136.69 (1C, C-1"); 137.14 (1C, C-1); 139.69 (d, $J_{4'-P}$ 5.8 Hz, 1C, C-4'); 140.82 (1C, C-4); 143.43 (1C, C-2'); 201.04 (1C, C-carbonyl).

MS FAB>0 m/z (GT): 599 [M−H]$^-$; 553 [M−4NH$_4$+Na+2H]; 531 [M+4NH$_4$+3H]$^-$.

Example 33

(E,E,E)-[4-9'-Triphosphono-2',6'-dimethyl-nona-2',6',8'-trienyloxymethyl)-phenyl]-phenyl-methanone (25)

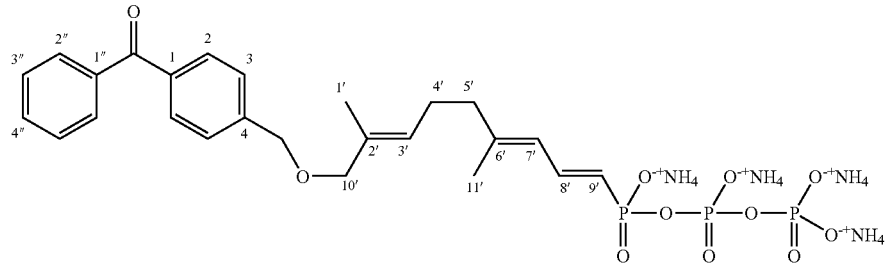

Total formula: $C_{25}H_{43}N_4O_{11}P_3$
Yield=17%
$R_f$=0.22 (4:6, 27% ammonia:isopropanol).
NMR $^1$H (D$_2$O), δ(ppm): 1.54 (s, 3H, CH$_3$); 1.73 (s, 3H, CH$_3$); 2.0-2.20 (m, 4H, H-4' and H-5'); 3.69 (s, 2H, H-1'); 4.44 (s, 2H, OCH$_2$-benzyl); 5.36 (m, 1H, H-3'); 5.74 (dd, $J_{9'-P}$ 19.6 Hz, $J_{9'-8'}$ 16.9 Hz, 1H, H-9'); 5.92 (d, $J_{7'-8'}$ 11.3 Hz, 1H, H-7'); 7.06 (ddd, $J_{8'-P}$ 20.7 Hz, 1H, H-8'); 7.30-751 (m, 4H, H-ar); 7.51-7.71 (m, 5H, H-ar).

NMR $^{31}$P (D$_2$O), δ(ppm): −21.0 (dd, $J_{β-α}$ 23.1 Hz, $J_{β-γ}$ 19.4 Hz, P-β); −7.5 (d, P-γ); 9.0 (d, P-α).

NMR $^{13}$C (D$_2$O), δ(ppm): 13.62 (1C, C-10'); 16.76 (1C, C-11"); 25.91 (1C, C-4'); 39.24 (1C, C-5'); 70.41 (1C, C-1'); 76.46 (1C OCH$_2$-benzyl); 120.53 (d, $J_{9'-P}$ 192.5 Hz, 1C, C-9'); 124.74 (d, $J_{7'-P}$ 26.3 Hz, 1C, C-7'); 128.08 (2C, C-ar); 128.82 (27C, C-ar); 130.34 (2C, C-ar); 130.74 (2C, C-ar); 129.61 (1C, C-3'); 132.14 (1C, C-4"); 133.66 (1C, C-2'); 136.32 (1C, C-1"); 136.99 (1C, C-5'); 140.88 (d, $J_{8'-P}$ 5.8 Hz, 1C, C-8'); 143.79 (1C, C-4); 147.03 (1C, C-6'); 199.56 (1C, C-carbonyl).

MS FAB>0 m/z (GT): 599 [M+4NH$_4$+3H]$^-$.

The aldehydes 26 and 27 were prepared according to the oxidation method with pyridinium bichromate described above.

Example 34

3-Methylbut-2-enal (26)

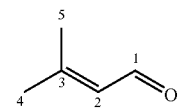

Total formula: $C_5H_8O$ Yield=95%
$R_f$=0.8 (95:5, petroleum ether:ethyl ether).

NMR ¹H (CDCL₃), δ(ppm): 1.96 (d, J₅₋₂ 1.3 Hz, 3H, H-5); 2.15 (d, J₄₋₂ 1.3 Hz, 3H, H-4); 5.86 (d, J₂₋₁ 8.2 Hz, 1H, H-2); 9.93 (d, 1H, H-1).

Example 35

3,7-Dimethylocta-2,6-dienal (27)

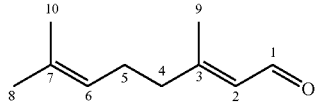

Total formula: C₁₀H₁₆O

Yield=99%

R_f=0.46 (8:2, petroleum ether:ethyl ether).

NMR ¹H (CDCL₃), δ(ppm): 1.6 (s, 3H, CH₃); 1.68 (s, 3H, CH₃); 2.16 (s, 3H, CH₃); 2.0-2.28 (m, 4H, H-4 and H-5); 4.93-5.15 (m, 1H, H-6); 5.88 (d, J₂₋₁ 8.0 Hz, 1H, H-2); 9.99 (d, 1H, H-1).

NMR ¹³C (CDCL₃), δ(ppm): 17.50 (1C, C-10), 22.10-22.19 (2C, C-8 and C-9), 22.98 (1C, C-5), 40.78 (1C, C-4), 122.96 (1C, C-6), 128.69 (1C, C-2), 132.01 (1C, C-7), 165.89 (1C, C-3), 192.45 (1C, C-1).

The phosphonic esters below were prepared according to the Horner-Wadsworth-Emmons method described above.

Example 36

Diethyl (E)-4-Methyl-1,3-pentadienylphosphonate (28)

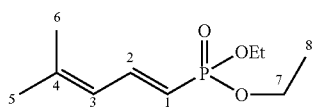

Total formula: C₁₀H₁₉O₃P

Yield=85%

R_f=0.46 (ethyl ether).

NMR ¹H (CDCL₃), δ(ppm): 1.31 (t, J₈₋₇ 7.1 Hz, 6H, H-8); 1.85 (6H, H-5 and H6); 3.95-4.15 (q, 4H, H-7) 5.51 (dd, J₁₋₂ 16.6 Hz, J₁₋P 20.2 Hz, 1H, H-1); 5.94 (d, J₃₋₂ 10.9 Hz, 1H, H-3); 7.35 (ddd, J₂₋P 21.0 Hz, 1H, H-2).

NMR ³¹P (CDCL₃), δ(ppm): 19.4

NMR ¹³C (CDCL₃), δ(ppm): 16.71-16.77 (2C, C-8), 16.24 (1C, C-6), 26.74 (d, J₅₋P 1.2 Hz, 1C, C-5), 61.86-61.92 (2C, C-7), 111.97 (d, J₁₋P 192.0 Hz, 1C, C-1), 125.17 (d, J₃₋P 26.34 Hz, 1C, C-3), 145.66 (d, J₂₋P 6.6 Hz, 1C, C-2), 145.67 (1C, C-4).

MS FAB>0 m/z (NOBA): 219 [M+H]⁺; 241 [M+Na]⁺.

Example 37

(E,E)-4,8-Dimethyl-1,3,7-diethyl nonatrienylphosphonate (29)

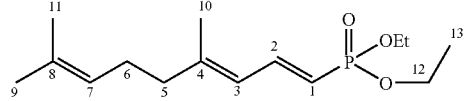

Total formula: C₁₅H₂₇O₃P

Yield=80%

R_f=0.6 (ethyl ether).

NMR ¹H (CDCL₃), δ(ppm): 1.32 (t, J₁₃₋₁₂ 6.7 Hz, 6H, H-13); 1.60 (s, 3H, CH₃); 1.67 (s, 3H, CH₃); 1.85 (s, 3H, CH₃); 2.05-2.15 (m, 2H, H-6); 2.18-2.32 (m, 2H, H-5); 3.95-4.20 (q, 4H, H-12); 4.95-5.11 (m, 1H, H-7); 5.53 (dd, J₁₋₂ 16.6 Hz, J₁₋P 20.3 Hz, 1H, H-1); 5.96 (d, J₃₋₂ 11.3 Hz, 1H, H-3); 7.32 (ddd, J₂₋P 20.9 Hz, 1H, H-3).

NMR ³¹P (CDCL₃), δ(ppm): 21.0.

NMR ¹³C (CDCL₃), δ(ppm): 16.74-16.80 (2C, C-13); 17.72-18.08 (2C, C-10 and C-11); 26.07 (1C, C-9); 26.64 (1C, C-6); 40.50 (1C, C-5); 61.90-61.96 (2C, C-17); 114.27 (d, J₁₋P 192.0 Hz, 1C, C-1); 123.72 (1C, C-7); 124.69 (d, J₃₋P 26.7 Hz, 1C, C-3); 132.58 (1C, C-8); 144.69 (d, J₂₋P 6.7 Hz, 1C, C-2); 149.22 (1C, C-4).

MS FAB>0 m/z (NOBA): 287 [M+H]⁺; 309 [M+Na]⁺; 259 [M−CH₂CH₃+H]⁺.

Example 38

Diethyl (E)-1,3-butadienylphosphonate (30)

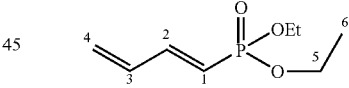

Total formula: C₈H₁₅O₃P

Yield=71.34%

R_f=0.39 (ethyl ether).

NMR ¹H (CDCL₃), δ(ppm): 1.31 (t, J₆₋₅ 7.1 Hz, 6H, H-6); 3.98-4.16 (q, 4H, H-5); 5.45 (d, J₄₋₃ 9.6 Hz, 1H, H-4); 5.55 (d, J₄'₋₃ 16.8 Hz, 1H, H-4'); 5.71 (dd, J₁₋P 19.1 Hz, J₁₋₂ 16.9 Hz, 1H, H-1), 6.40 (ddd, J₃₋₂ 10.6 Hz, 1H, H-3); 7.08 (ddd, J₂₋P 20.8 Hz, 1H, H-2).

NMR ³¹P (CDCL₃), δ(ppm): 19.9.

NMR ¹³C (CDCL₃), δ(ppm): 16.75 (2C, C-6); 62.17 (2C, C-5); 118.44 (d, J₁₋P 190.4 Hz, 1C, C-1); 128.32 (1C, C-4); 136.11 (d, J₃₋P 27.1 Hz, 1C, C-3); 149.25 (d, J₂₋P 5.7 Hz, 1C, C-2).

MS FAB>0 m/z (NOBA): 191 [M+H]⁺; 213 [M+Na]⁺.

Example 39

Diethyl (E)-1,3-pentadienylphosphonate (31)

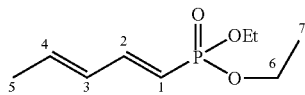

Total formula: $C_9H_{17}O_3P$
Yield=79%
$R_f=0.35$ (ethyl ether).
NMR $^1$H (CDCL$_3$), δ(ppm): 1.33 (t, $J_{7-6}$ 4.7 Hz, 6H, H-7); 5.24 (d, $J_{5-4}$ 5.2 Hz, 3H, H-5); 3.95-4.20 (qt, 4H, H-6); 5.56 (dd, $J_{1-P}$ 19.5 Hz, $J_{1-2}$ 16.9 Hz, 1H, H-1); 6.0-6.25 (m, 2H, H-3 and H-4); 7.07 (ddd, $J_{2-P}$ 20.9 Hz, $J_{2-3}$ 9.4 Hz, 1H, H-2).
NMR $^{31}$P (CDCL$_3$), δ(ppm): 21.2.
NMR $^{13}$C (CDCL$_3$), δ(ppm): 16.76 (2C, C-7); 18.83 (1C, C-5); 62 (2C, C-6); 114.66 (d, $J_{1-P}$ 191.6 Hz, 1C, C-1); 131.22 (d, $J_{3-P}$ 26.3 Hz, 1C, C-3); 138.96 (1C, C-4); 149.59 (d, $J_{2-P}$ 6.1 Hz, 1C, C-2).
MS FAB>0 m/z (NOBA): 205 [M+H]$^+$; 227 [M+Na]$^+$.

The phosphonic acids below were prepared by means of the action of trimethylsilane bromide on their phosphonic esters as described above.

Example 40

(E)-4-methylpenta-1,3-dienylphosphonic acid (32)

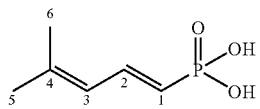

Total formula: $C_6H_{11}O_3P$
Yield=99%
$R_f=0.28$ (4:6, 27% ammonia: isopropanol).
NMR $^1$H (CDCL$_3$), δ(ppm): 1.79 (s, 6H, H5 and H-6); 5.79 (dd, $J_{1-2}$ 16.8 Hz, $J_{1-P}$ 17.3 Hz, 1H, H-1); 5.85 (d, $J_{3-2}$ 11.0 Hz, 1H, H-3); 7.08 (ddd, $J_{2-P}$ 19.4 Hz, 1H, H-2).
NMR $^{31}$P (CDCL$_3$), δ(ppm): 23.2.
NMR $^{13}$C (CDCL$_3$), δ(ppm): 17.45 (1C, C-6), 27.84 (1C, C-5), 115.97 (d, $J_{1-P}$ 192.5 Hz, 1C, C-1), 125.39 (d, $J_{3-P}$ 26.7 Hz, 1C, C-3), 142.50 (d, $J_{2-P}$ 6.4 Hz, 1C, C-2), 145.67 (1C, C-4).
MS FAB>0 m/z (NOBA): 163 [M+H]$^+$; 185 [M+Na]$^+$.

Example 41

(E,E)-4,8-dimethylnona-1,3,7-trienylphosphonic acid (33)

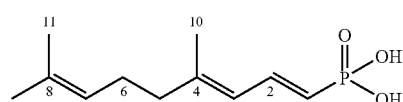

Total formula: $C_{11}H_{19}O_3P$
Yield=85%
$R_f=0.45$ (4:6, 27% ammonia: isopropanol).
NMR $^1$H (CDCL$_3$), δ(ppm): 1.63 (s, 3H, CH$_3$); 1.71 (s, 3H, CH$_3$); 1.86 (s, 3H, CH$_3$); 1.92-2.16 (m, 4H, H-5 and H-6); 5.0-5.15 (m, 1H, H-7); 5.66 (dd, $J_{1-2}$ 17.9 Hz, $J_{1-P}$ 18.5 Hz, 1H, H-1); 5.8-5.95 (m, 1H, H-3); 7.10-7.40 (m, 1H, H-2); 9.87 (s, 2H, POH).
NMR $^{31}$P (CDCL$_3$), δ(ppm): 23.4.
NMR $^{13}$C (CDCL$_3$), δ(ppm): 17.87-18.24 (2C, C-10 and C-11); 26.18 (1C, C-9); 26.72 (1C, C-6); 40.63 (1C, C-5); 118.37 (d, $J_{1-P}$ 192.6 Hz, 1C, C-1); 123.85 (1C, C-7); 124.79 (d, $J_{3-P}$ 26.9 Hz, 1C, C-3); 132.61 (1C, C-8); 141.59 (d, $J_{2-P}$ 6.3 Hz, 1C, C-2); 148.37 (1C, C-4).
MS FAB>0 m/z (NOBA): 231 [M+H]$^+$; 253 [M+Na]$^+$.

Example 42

(E)-buta-1,3-dienylphosphonic acid (34)

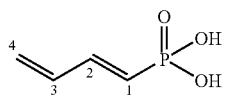

Total formula: $C_4H_8O_3P$
Yield=85%
$R_f=0.4$ (4:6, 27% ammonia: isopropanol).
NMR $^1$H (CDCL$_3$), δ(ppm): 5.44 (d, $J_{4-3}$ 10.0 Hz, 1H, H-4); 5.96 (dd, $J_{1-P}$ 18.7 Hz, $J_{1-2}$ 17.0 Hz, 1H, H-1); 6.52 (ddd, $J_{3-2}$ 10.5 Hz, J3-4 10.0 Hz, $J_{3-4'}$ 16.9 Hz, 1H, H-3); 6.98 (ddd, $J_{2-P}$ 20.8 Hz, H-2); 10.31 (s, 2H, POH).
NMR $^{31}$P (CDCL$_3$), δ(ppm): 19.2.
NMR $^{13}$C (CDCL$_3$), δ(ppm): 122.14 (d, $J_{1-P}$ 190.9 Hz, 1C, C-1); 123.77 (1C, C-4); 136.74 (d, $J_{3-P}$ 27.0 Hz, 1C, C-3); 146.01 (d, $J_{2-P}$ 5.4 Hz, 1C, C-2).
MS FAB>0 m/z (NOBA): 135 [M+H]$^+$.

Example 43

(E,E)-penta-1,3-dienylphosphonic acid (35)

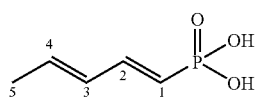

Total formula: $C_5H_9O_3P$
Yield=90%
$R_f=0.38$ (4:6, 27% ammonia: isopropanol).
NMR $^1$H (Acetone d$_6$), δ(ppm): 1.83 (d, $J_{5-4}$ 6.0 Hz, 3H, H-5); 5.75 (dd, $J_{1-P}$ 18.9 Hz, J1-2 16.9 Hz, 1H, H-1); 6.08-6.25 (m, 2H, H-3 and H-4); 6.96 (ddd, $J_{2-P}$ 21.1 Hz, $J_{2-1}$ 16.86 Hz, $J_{2-3}$ 9.7 Hz, 1H, H-2); 10.15 (s, 2H, POH).
NMR $^{31}$P (Acetone d$_6$), δ(ppm): 20.4.
NMR $^{13}$C (Acetone d$_6$), δ(ppm): 17.94 (1C, C-5); 118.41 (d, $J_{1-P}$ 192.9 Hz, 1C, C-1); 131.49 (d, $J_{3-P}$ 26.8 Hz, 1C, C-3); 137.41 (1C, C-4); 146.20 (d, $J_{2-P}$ 5.7 Hz, 1C, C-2).
MS FAB>0 m/z (NOBA): 149 [M+H]$^+$; 171 [M+Na]$^+$.

Example 44

Triammonium (E)-4-methylpenta-1,3-dienylpyrophosphonate (36)

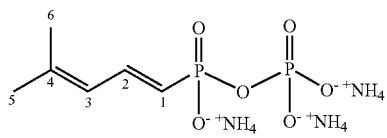

Total formula: $C_6H_{21}O_6P_2$

Yield=70%

$R_f$=0.25 (4:6, 27% ammonia:isopropanol).

NMR $^1$H (D$_2$O), δ(Ppm): 1.71 (s, 3H, CH$_3$); 1.73 (s, 3H, CH$_3$); 5.72 (dd, J$_{1-2}$ 16.8 Hz, J$_{1-P}$ 19.5 Hz, 1H, H-1); 5.88 (d, J$_{3-2}$ 10.9 Hz, 1H, H-3); 7.01 (ddd, J$_{2-P}$ 20.6 Hz, 1H, H-2).

NMR $^{31}$P (D$_2$O), δ(ppm): −6.61 (d, J$_{P2-P1}$ 23.1 Hz, 1P, P2); 7.43 (d, J$_{P1-P2}$ 23.1 Hz, 1P, P-1).

NMR $^{13}$C (D$_2$O), δ(ppm): 18.22-25.64 (2C, C-5 and C-6); 121.50 (d, J$_{1-P}$ 184.2 Hz, 1C, C-1), 124.90 (d, J$_{3-P}$ 25.8 Hz, 1C, C-3), 140.11 (d, J$_{2-P}$ 5.7 Hz, 1C, C-2), 143.82 (1C, C-4).

MS FAB>0 m/z (GT): 241 [M−3NH$_4$+2H]$^-$.

Example 45

Triammonium (E,E)-4,8-Dimethylnona-1,3,7-trienylpyrophosphonate (37)

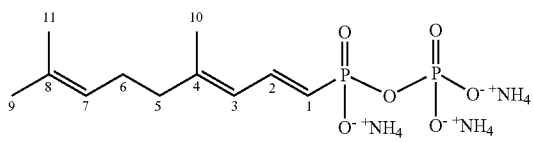

Total formula: $C_{11}H_{29}N_3O_6P_2$

Yield=58%

$R_f$=0.28 (4:6, 27% ammonia: isopropanol).

NMR $^1$H (D$_2$O), δ(ppm): 1.48 (s, 3H, CH$_3$); 1.53 (s, 3H, CH$_3$); 1.70 (s, 3H, CH$_3$); 1.95-2.15 (m, 4H, H-5 and H-6); 4.95-5.12 (m, 1H, H-7); 5.74 (dd, J$_{1-2}$ 16.9 Hz, J$_{1-P}$ 19.4 Hz, 1H, H-1); 5.88 (d, J$_{3-2}$ 11.1 Hz, 1H, H-3); 6.98 (ddd, J$_{2-P}$ 20.5 Hz 1H, H-2).

NMR $^{31}$P(D$_2$O), δ(ppm): -5.70 (d, J$_{β-α}$21.3 Hz, P-β); 7.11 (d, P-α).

NMR $^{13}$C (D$_2$O), δ(ppm): 16.65-17.28 (2C, C-10 and C-11; 25.16 (1C, C-9); 25.93 (1C, C-6); 39.55 (1C, C-5); 120.91 (d, J$_{1-P}$ 183.9 Hz, 1C, C-1); 124.24 (1C, C-7); 124.70 (d, J$_{3-P}$ 26.3 Hz, 1C, C-3); 134.21 (1C, C-8); 143.95 (d, J$_{2-P}$ 6.2 Hz, 1C, C-2); 147.58 (1C, C-4).

MS FAB>0 m/z (GT): 309 [M−3NH$_4$+2H]$^-$.

Example 46

Triammonium (E)-buta-1,3-dienylpyrophosphonate (38)

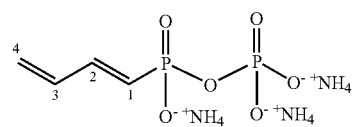

Total formula: $C_4H_{17}N_3O_6P_2$

Yield=61%

$R_f$=0.16 (4:6, 27% ammonia:isopropanol).

NMR $^1$H (D$_2$O), δ(ppm): 5.23 (d, J$_{4-3}$ 9.8 Hz, 1H, H-4); 5.38 (d, J$_{4'-3}$ 16.8 Hz, 1H, H-4'); 5.90 (dd, J$_{1-P}$ 18.3 Hz, J$_{1-2}$ 17.04 Hz, 1H, H-1); 6.36 (ddd, J$_{3-2}$ 10.4 Hz, 1H, H-3); 6.72 (ddd, J$_{2-P}$ 20.0 Hz, 1H, H-2).

NMR $^{31}$P (D$_2$O), δ(Ppm): −5.70 (d, J$_{β-α}$ 23.5 Hz, P-β); 6.6 (d, P-α).

NMR $^{13}$C (D$_2$O), δ(ppm): 122.48 (1C, C-4); 125.24 (d, J$_{1-P}$ 183.4 Hz, 1C, C-1); 137.26 (d, J$_{3-P}$ 26.1 Hz, 1C, C-3); 143.59 (d, J$_{2-P}$ 4.9 Hz, 1C, C-2).

MS FAB>0 m/z (GT): 232 [M−2NH4+2H]$^+$; 215 [M−3NH4+4H]$^+$.

Example 47

Triammonium (E,E)-Penta-1,3-dienylpyrophosphonate (39)

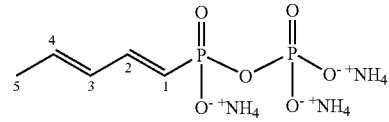

Total formula: $C_5H_{19}N_3O_6P_2$

Yield=63%

$R_f$=0.18 (4:6, 27% ammonia:isopropanol).

NMR $^1$H (D$_2$O), δ(ppm): 1.67 (d, J$_{5-4}$ 6.4 Hz, 3H, H-5); 5.74 (dd, J$_{1-P}$ 18.6 Hz, J$_{1-2}$ 17.0 Hz, 1H, H-1); 5.85-6.20 (m, 22H, H-3 and H-4); 6.68 (ddd, J$_{2-P}$ 20.3 Hz, J$_{2-3}$ 9.7 Hz, 1H, H-2).

NMR $^{31}$P (D$_2$O), δ(ppm): −6.4 (d, J$_{β-α}$ 23.1 Hz, P-β); 6.8 (d, P-α).

NMR $^{13}$C (D$_2$O), δ(ppm): 17.88 (1C, C-5); 121.62 (d, J$_{1-P}$ 185.1 Hz, 1C, C-1); 129.32 (d, J$_{3-P}$ 25.5 Hz, 1C, C-3); 136.52 (1C, C-4); 143.66 (d, J$_{2-P}$ 5.0 Hz, 1C, C-2).

MS FAB>0 m/z (GT): 246 [M−2NH4+2H]⁺; 229 [M−3NH4+4H]⁺.

Example 48

Tetraammonium (E)-4-methylpenta-1,3-dienyltriphosphonate (40)

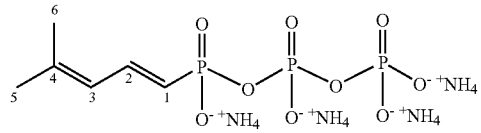

Total formula: $C_6H_{25}N_3O_9P_3$

Yield=7%

$R_f$=0.15 (4:6, 27% ammonia:isopropanol).

NMR $^1$H (D$_2$O), δ(ppm): 1.72 (s, 3H, CH$_3$); 1.74 (s, 3H, CH$_3$); 5.72 (dd, J$_{1-2}$ 16.8 Hz, J$_{1-P}$ 20.3 Hz, 1H, H-1); 5.90 (d, J$_{3-2}$ 11.1 Hz, 1H, H-3); 7.10 (ddd, J$_{2-P}$ 21.1 Hz, 1H, H-2).

NMR $^{31}$P (D$_2$O), δ(Ppm): −21.4 (dd, J$_{β-α}$ 21.2 Hz, J$_{β-γ}$ Hz, P-β); −5.5 (d, P-γ); 9.10 (d, P-α).

NMR $^{13}$C (D$_2$O), δ(ppm): 18.24-25.66 (2C, C-5 and C-6); 121.53 (d, J$_{1-P}$ 183.5 Hz, 1C, C-1); 124.91 (d, J$_{3-P}$ 25.4 Hz, 1C, C-3); 140.13 (d, J$_{2-P}$ 5.7 Hz, 1C, C-2), 143.82 (1C, C-4).

MS FAB>0 m/z (GT): 323 [M−4NH$_4$+5H]⁺.

Example 49

Tetraammonium (E,E)-4,8-dimethylnona-1,3,7-trienyltriphosphate (41)

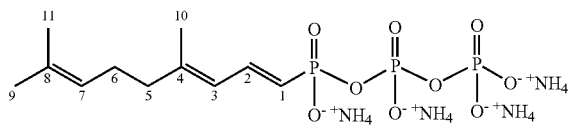

Total formula: $C_{11}H_{33}N_4O_9P_3$

Yield=12%

$R_f$=0.15 (4:6, 27% ammonia:isopropanol).

NMR $^1$H (D$_2$O), δ(ppm): 1.62 (s, 3H, CH$_3$); 1.68 (s, 3H, CH$_3$); 1.85 (s, 3H, CH$_3$); 2.13-2.22 (m, 4H, H-5 and H-6); 5.86 (dd, J$_{1-2}$ 16.8 Hz, J$_{1-P}$ 20.2 Hz, 1H, H-1); 6.03 (d, J$_{3-2}$ 11.0 Hz, 1H, H-3); 7.19 (ddd, J$_{2-P}$ 21.0 Hz, 1H, H2).

NMR $^{31}$P(D$_2$O), δ(ppm): -21.2 (dd, J$_{β-α}$22.1 Hz, J$_{β-γ}$20.0 Hz, P-β); -6.3 (d, P-γ); 8.5 (d, P -α).

NMR $^{13}$C (D$_2$O), δ(ppm): 16.66-17.28 (2C, C-10 and C-11); 25.17 (1C, C-9); 25.93 (1C, C-6); 39.56 (1C, C-5); 121.93 (d, J$_{1-P}$ 184.0 Hz, 1C, C-1); 124.25 (1C, C-7); 124.73 (d, J$_{3-P}$ 26.4 Hz, 1C, C-3); 134.26 (1C, C-8); 143.69 (d, J$_{2-P}$ 6.2 Hz, 1C, C-2); 147.84 (1C, C-4).

MS FAB>0 m/z (GT): 406 [M−3NH$_4$+4H]⁺; 389 [M−4NH$_4$+4H]⁺.

Example 50

Tetraammonium (E)-buta-1,3-dienyltriphosphonate (42)

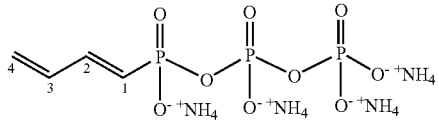

Total formula: $C_4H_{21}N_4O_9P_3$

Yield=7%

$R_f$=0.08 (4:6, 27% ammonia:isopropanol).

NMR $^1$H (D$_2$O), δ(Ppm): 5.20 (d, J$_{4-3}$ 10.1 Hz, 1H, H-4); 5.33 (d, J$_{4'-3}$ 16.9 Hz, 1H, H-4'); 5.79 (dd, J$_{1-P}$ 19.5 Hz, J$_{1-2}$ 16.98 Hz, 1H, H-1); 6.28 (ddd, J$_{3-2}$ 10.3 Hz, 1H, H-3); 6.68 (ddd, J$_{2-P}$ 20.7 Hz, 1H, H-2).

NMR $^{31}$P (D$_2$O), δ(Ppm): −21.5 (m, P-β); −8.5 (d, P-γ); 7.6 (d, J$_{α-β}$ 22.5 Hz, P-α).

NMR $^{13}$C (D$_2$O), δ(ppm): 123.49 (d, J$_{1-P}$ 186.4 Hz, 1C, C-1); 123.90 (1C, C-4); 136.71 (d, J$_{3-P}$ 26.7 Hz, 1C, C-3); 144.92 (d, J$_{2-P}$ 5.7 Hz, 1C, C-2).

MS FAB>0 m/z (GT): 395 [M−4NH$_4$+5H]⁺.

Example 51

Tetraammonium (E)-penta-1,3-dienyltriphosphonate (43)

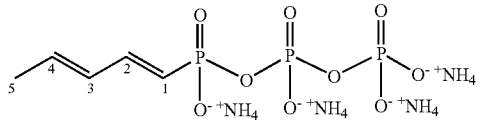

Total formula: $C_5H_{23}N_4O_9P_3$

Yield=7%

$R_f$=0.10 (4:6, 27% ammonia:isopropanol).

NMR $^1$H (D$_2$O) δ(ppm): 1.68 (d, J$_{5-4}$ 6.4 Hz, 3H, H-5); 5.76 (dd, J$_{1-P}$ 18.7 Hz, J$_{1-2}$ 17.0 Hz, 1H, H-1); 5.87-6.22 (m, 2H, H-3 and H-4); 6.69 (ddd, J$_{2-P}$ 20.5 Hz, J$_{2-3}$ 9.7 Hz, 1H, H-2).

NMR $^{31}$P (D$_2$O), δ(ppm): −21.3 (m, P-β); −6.5 (d, P-γ); 7.4 (d, J$_{α-β}$ 22.3 Hz, P-α).

NMR $^{13}$C (D$_2$O), δ(ppm): 17.87 (1C, C-5); 121.63 (d, 185.1 Hz, 1C, C-1); 129.32 (d, J$_{3-P}$ 25.5 Hz, 1C, C3); 143.67 (d, J$_{2-P}$ 5.0 Hz, 1C, C-2).

MS FAB>0 m/z (GT): 309 [M−4NH$_4$+5H]⁺.

Example 52

Triammonium α,γ-(4-methylpenta-1,3-dienyl)triphosphonate (44)

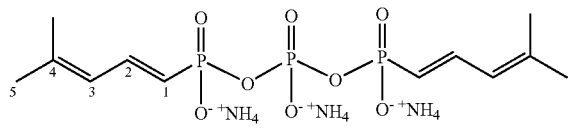

Total formula: $C_{12}H_{30}N_3O_8P_3$
Yield=4%
$R_f$=0.40 (4:6, 27% ammonia:isopropanol).
NMR $^1H$ (D$_2$O), δ(ppm): 1.70 (s, 6H, 2CH$_3$); 1.3 (s, 6H, 2CH$_3$); 5.70 (dd, $J_{1-2}$ 16.8 Hz, $J_{1-P}$ 19.5 Hz, 2H, H-1); 5.90 (d, $J_{3-2}$ 10.9 Hz, 2H, H-3); 6.69 (ddd, $J_{2-P}$ 20.6 Hz, 2H, H-2).
NMR $^{31}P$(D$_2$O), δ(ppm): -20.3 (t, $J_{β-α}$=J β-γ=22.2 Hz, 1P, P-β); 7.2 (d, 2P, 2P-α, P-γ).
NMR $^{13}C$ (D$_2$O), δ(ppm): 18.21-25.61 (4C, C-5 and C-6); 121.52 (d, $J_{1-P}$ 184.2 Hz, 2C, C-1), 124.91 (d, $J_{3-P}$ 25.8 Hz, 2C, C-3), 140.05 (d, $J_{2-P}$ 5.8 Hz, 2C, C-2), 143.84 (2C, C-4).
MS FAB>0 m/z (GT): 387 [M–3NH$_4$+4H]$^+$.

Example 53

Triammonium α,γ-(buta-1,3-dienyl)triphosphonate (45)

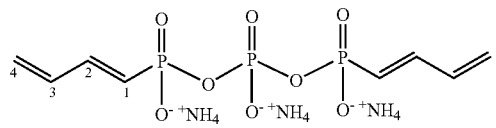

Total formula: $C_8H_{22}N_3O_8P_3$
Yield=5%
$R_f$=0.25 (4:6, 27% ammonia:isopropanol).
NMR $^1H$ (D$_2$O), δ(ppm): 5.22 (d, $J_{4-3}$ 9.7 Hz, 2H, H-4); 5.35 (d, $J_{4'-3}$ 16.7 Hz, 2H, H-4'); 5.90 (dd, $J_{1-P}$ 18.3 Hz, J1-2 17.0 Hz, 2H, H-1); 6.40 (ddd, $J_{3-2}$ 10.4 Hz, 2H, H-3); 6.72 (ddd, $J_{2-P}$ 20.1 Hz, 2H, H-2).
NMR $^{31}P$(D$_2$O), δ(ppm): -20.1 (t, $J_{β-α}$=$J_{β-α}$22.4 Hz, 1P, P-β); 7.5 (d, 2P, P-α, P-γ).
NMR $^{13}C$ (D$_2$O), δ(ppm): 123.49 (d, $J_{1-P}$ 186.5 Hz, 2C, C-1); 123.91 (2C, C-4); 136.72 (d, $J_{3-P}$ 26.7 Hz, 2C, C-3); 144.94 (d, $J_{2-P}$ 5.8 Hz, 2C, C-2).
MS FAB>0 m/z (GT): 331 [M–3NH$_4$+4H]$^+$.

Example 54

Triammonium α,γ-(penta-1,3-dienyl)triphosphonate (46)

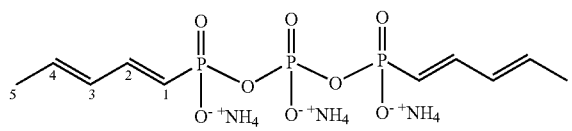

Total formula: $C_{10}H_{26}N_3O_8P_3$
Yield=2%
$R_f$=0.5 (4:6, 27% ammonia:isopropanol).
NMR $^1H$ (D$_2$O), δ(ppm): 1.68 (d, $J_{5-4}$ 6.4 Hz, 6H, H-5); 5.75 (dd, $J_{1-P}$ 18.6 Hz, $J_{1-2}$ 17.1 Hz, 2H, H-1); 5.86-6.22 (m, 4H, H-3 and H-4); 6.68 (ddd, $J_{2-P}$ 20.4 Hz, $J_{2-3}$ 9.74 Hz, 2H, H-2).
NMR $^{31}P$ (D$_2$O), δ(ppm): -20.1 (t, $J_{β-α}$=$J_{β-γ}$ 22.5 Hz, 1P, P-β); 7.5 (d, 2P, P-α, P-γ).
NMR $^{13}C$ (D$_2$O), δ(ppm): 17.89 (2C, C-5); 121.63 (d, $J_{1-P}$ 185.1 Hz, 2C, C-1); 129.33 (d, $J_{3-P}$ 25.3 Hz, 2C, C-3); 136.51 (2C, C-4); 143.66 (d, $J_{2-P}$ 5.4 Hz, 2C, C-2).
MS FAB>0 m/z (GT): 359 [M–3NH$_4$+4H]$^+$.

Example 55

3-methylbut-3-enyl benzoate (47)

In a 250 ml flask, in a nitrogen atmosphere, 3-methylbut-3-enole (10 g, 116 mmol, 1 eq) dissolved in 100 ml of dichloromethane is introduced, followed by triethylamine (23.5 g, 236 mmol, 2 eq) at –0° C. Benzoyl chloride (24.4 g, 174 mmol, 1.5 eq) in solution in 20 ml of dichloromethane is then added over a 10 min period.

After 30 min of reaction, the temperature is increased to 25° C. and the organic phase washed with iced water (100 ml), 10% hydrochloric acid (100 ml) and with a saturated NaHCO$_3$ solution. After drying on sodium sulphates and evaporation of the dichloromethane, the residual oil obtained undergoes silica gel chromatography (4:6 ethyl ether:petroleum ether) to produce a colourless oil.

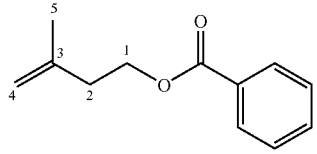

Total formula: $C_{12}H_{14}O_2$
Yield=100%
$R_f$=0.70 (4:6, ethyl ether: petroleum ether).
NMR $^1H$ (CDCL$_3$), δ(ppm): 1.84 (S, 3H, H-5), 2.51 (t, $J_{2-1}$ 6.7 Hz, 2H, H-2), 4.47 (t, $J_{1-2}$ 6.7 Hz, 2H, H-1), 4.82-4.92 (m, 2H, H-4), 7.40-7.50 (m, 2H, H-ar), 7.52-7.65 (m, 1H, H-ar), 8.02-8.12 (m, 2H, H-ar).
NMR $^{13}C$ (CDCL$_3$), δ(ppm): 22.96 (1C, C-5), 37.24 (1C, C-2), 63.59 (1C, C-1), 112.85 (1C, C-4), 128.76-129.80 (4C, C-ar), 130.82 (1C, C—C=O), 133.28 (1C, C-ar), 142.15 (1C, C-3), 166.99 (1C, C-carbonyl).
MS FAB>0 m/z (NOBA): 191 [M+H]$^+$; 212 [M+Na]$^+$.

Example 56

4-hydroxy-3-methylbutyl benzoate (48)

In a 100 ml flask in a nitrogen atmosphere, 3-methylbut-3-enyl benzoate (2 g, 10.52 mmol, 1 eq) is solubilised in 2 ml of anhydrous THF and BH$_3$.Me$_2$S (1.8 ml, 3.5 mmol, 2 M solution in THF, 1/3 eq) is then added at 0° C. over a 5 min period; the whole is allowed to return to ambient temperature. After 2 hours of reaction, H$_2$O$_2$ (4 ml, 30% aqueous solution, 3 eq) is added drop by drop at 0° C. and magnetic stirring is continued for 30 min.

The organic phase is extracted with 3×100 ml ethyl ether, the ethereal phases are collected and washed with water (3×100 ml) and dried on sodium sulphate. After evaporation of the solvent, the residual oil obtained then undergoes silica gel chromatography to produce a colourless oil (ethyl ether: petroleum ether, 4:6).

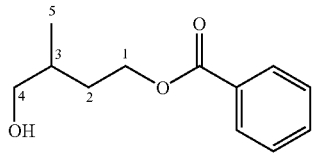

Total formula: $C_{12}H_{16}O_3$
Yield=70%
$R_f$=0.38 (4:6, ethyl ether: petroleum ether).
NMR $^1$H (CDCL$_3$), δ(ppm): 1.04 (m, 3H, H-5), 1.65-2.00 (m, 3H, H-2 and H-3), 3.58 (d, $J_{4-3}$ 4.7 Hz, 2H, H-4), 4.43 (td, $J_{1-2}$ 6.7 Hz, $J_{1-3}$ 2.8 Hz, 2H, H-1), 7.45 (m, 3H, H-ar), 8.08 (m, 2H, H-ar).
NMR $^{13}$C (CDCL$_3$), δ(ppm): 16.97 (1C, C-5), 32.56-33.43 (2C, C-2 and C-3), 63.70 (1C, C-1), 68.34 (1C, C-4), 128.75-129.96 (4C, C-ar), 130.77 (1C, C—C=O), 133.34 (1C, C-ar), 167.12 (1C, C-carbonyl).
MS FAB>0 m/z (NOBA): 209 [M+H]$^+$; 231 [M+Na]$^+$.

Example 57

3-methyl-4-(pyranyl-2'-oxy)butyl benzoate (49)

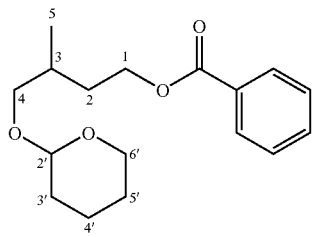

Total formula: $C_{17}H_{24}O_4$
Yield=100%
$R_f$=0.68 (4:6, ethyl ether: petroleum ether).
NMR $^1$H (CDCL$_3$), δ(ppm): 1.05 (m, 3H, H-5), 1.50-1.75 (m, 6H, H-4', H-5' and H-6'), 1.75-2.12 (m, 3H, H-2 and H-3), 3.20-3.32 (m, 1H, H-3'), 3.42-3.56 (m, 1H, H-4), 3.58-3.61 (m, 1H, H-3'), 3.72-3.93 (m, 1H, H-4), 4.35-4.53 (m, 2H, H-1), 4.56-4.61 (m, 1H and H-2'), 7.35-7.60 (m, 3H, H-ar), 8.05-8.12 (m, 2H, H-ar).
NMR $^{13}$C (CDCL$_3$), δ(ppm): 17.51 (1C, C-5), 19.94 (C-4'), 25.88 (C-5'), 31.09-31.12-31.19-31.22 (2C, C-2 and C-3), 33.12-33.18 (1C, C-3'), 62.65 (C-6'), 63.81 (C-1), 63.88 (C-1), 73.05 (C-4), 73.12 (C-4), 99.38 (C-2'), 99.42 (C-2'), 128.74-129.97 (4C, C-ar), 130.90 (1C, C—C=O), 133.24 (1C, C-ar), 146.08 (1C, C-carbonyl).
MS FAB>0 m/z (NOBA): 293 [M+H]$^+$; 315 [M+Na]$^+$.

Example 58

3-Methyl-4-(pyranyl-2'-oxy)butanol (50)

To a potassium carbonate suspension (2.07 g, 15.06 mmol, 4 eq) in 25 ml of methanol, in a 100 ml flask equipped with a chloride retainer, 3-methyl-4-(pyranyl-2'-oxy)butyl benzoate (1.1 g, 3.76 mmol, 1 eq) is added and the mixture is kept under magnetic stirring, at ambient temperature for 6 hours. After evaporation of the solvent, the residual oil obtained then undergoes silica gel chromatography to produce a colourless oil (ethyl ether:petroleum ether, 4:6).

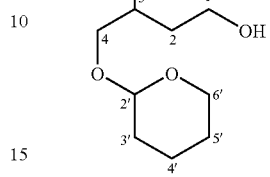

Total formula: $C_{10}H_{20}O_3$
Yield=95%
$R_f$=0.33 (4:6, ethyl ether: petroleum ether).
NMR $^1$H (CDCL$_3$), δ(ppm): 0.95 (m, 3H, H$_5$), 1.50-1.75 (m, 6H, H-4', H-5' and H-6), 1.75-2.00 (m, 3H, H-2 and H-3), 2.55 (s, 1H, OH), 3.15-3.32 (m, 1H, H-4), 3.45-3.95 (m, 5H, H-1, H-4 and H-3'), 4.65 (m, 1H, H-2').
NMR $^{13}$C (CDCL$_3$), δ(ppm): 17.66-17.73 (1C, C-5), 19.87-19.96 (1C, C-4') 25.75-25.92 (1C, C-5'), 31.01-31.12-31.15-31.20 (2C, C-2 and C-3), 33.97-34.0 (1C, C-3'), 61.43-61.51 (C-6'), 62.45-62.75 (C-1), 73.54-73.71 (C-4), 99.50-99.54 (C-2').
MS FAB>0 m/z (NOBA): 189 [M+H]$^+$; 211 [M+Na]$^+$.

Example 59

3-Methyl-4-(pyranyl-2'-oxy)butanal (51)

In a 100 ml flask equipped with a magnetic stirrer and in a nitrogen atmosphere, oxallyl chloride (0.9 g, 7.1 mmol, 1.1 eq) is placed in solution in 30 ml of dichloromethane. DMSO (1 g, 14.19 mmol, 2.2 eq) in 4 ml of dichloromethane is then added at −60° C. and the mixture stirred for 15 min. 3-methyl-4-(pyranyl-2'-oxy)butanol (1.25 g, 6.45 mmol, 1 eq) dissolved in 4 ml of dichloromethane is added to the reaction medium followed by n-triethylamine (3.26 g, 32.26 mmol, 5 eq) 15 min later. Magnetic stirring is maintained at −60° C. for 15 min and the reaction medium is then allowed to return to ambient temperature. After 30 min, the reaction is stopped by adding 50 ml of water, the organic phase is extracted with dichloromethane (3×100 ml), the organic phases are collected, washed once with water, with a 1 N hydrochloric acid solution (3×100 ml), dried on sodium sulphate, concentrated, and the residual oil obtained undergoes silica gel chromatography (4:6, ethyl ether: petroleum ether).

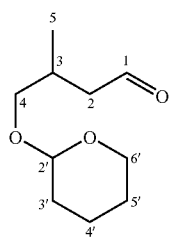

Total formula: $C_{10}H_{18}O_3$
Yield=99%
$R_f$=0.55 (4:6, ethyl ether: petroleum ether).

NMR $^1$H (CDCL$_3$), δ(ppm): 0.98 (d, J$_{5-4}$ 6.7 Hz, 3H, H-5), 1.40-1.80 (m, 6H, H-4', H-5' and H-6'), 2.18-2.60 (m, 3H, H-2 and H-3), 3.05-3.17 (m, 1/2H, H-4), 3.27-3.35 (m, 1/2H, H-4), 3.42-3.53 (m, 1H, H-3'), 3.45-3.54 (m, 1/2H, H-4), 3.65-3.74 (m, 1/2H, H-4), 3.70-3.83 (m, 1H, H-3'), 4.47-4.65 (m, 1H, H-2'), 9.72-9.78 (m, 1H, H-1).

NMR $^{13}$C (CDCL$_3$), δ(ppm): 17.50-17.52 (1C, C-5), 19.60-19.83 (1C, C-4'), 25.82 (1C, C-5'), 29.52-29.66 (1C, C-3), 30.83-30.89 (1C, C-3'), 48.99-49.16 (1C, C-2), 62.37-62.66 (1C, C-6'), 72.32-72.78 (1C, C-4), 98.96-99.58 (1C, C-2'), 202.89-202.94 (1C, C-1).

MS FAB>0 m/z (NOBA): 187 [M+H]$^+$; 209 [M+Na]$^+$.

Example 60

Diethyl 4-methyl-5-(pyranyl-2'-oxy)-pentenylphosphonate (52)

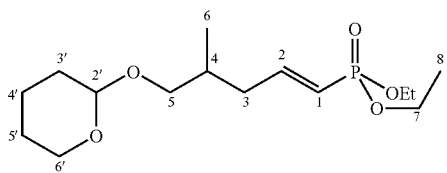

Total formula: C$_{15}$H$_{29}$O$_5$P
Yield=99%
R$_f$=0.75 (ethyl acetate).

NMR $^1$H (CDCL$_3$), δ(ppm): 0.84-0.98 (m, 3H, H-6), 1.28-1.36 (m, 6H, H-8), 1.4-2.1 (m, 8H, H-3, H-4', H-5' and H-6'), 2.28-2.55 (m, 1H, H-4), 3.10-3.24 (m, 1H, H 5), 3.38-3.52 (m, 1H, H-3'), 3.50-3.63 (m, 1H, H-5), 3.73-3.87 (m, 1H, H-3'), 3.95-4.13 (m, 4H, H-7), 4.49-4.55 (m, 1H, H-2'), 5.52-5.73 (m, 1H, H-1), 6.59-6.85 (m, 1H, H-2).

NMR $^{31}$P (CDCL$_3$), δ(ppm): 19.6.

NMR $^{13}$C (CDCL$_3$), δ(ppm): 16.70-16.74 (2C, C-8), 17.14-17.18 (1C, C-6), 19.87-19.90 (1C, C-4'), 25.66-25.84 (1C, C-5'), 31.0-31.02 (1C, C-3'), 33.26-33.29 (1C, C-4), 38.40-38.62-38.83-39.09 (1C, C-3), 62.01-62.06 (2C, C-7), 62.59-62.63 (1C, C-6'), 72.35-72.51 (1C, C-5), 99.26-99.44 (1C, C-2'), 117.68-117.73-119.54-119.60 (1C, C-1), 152.67-152.72 (1C, C-2).

MS FAB>0 m/z (NOBA): 321 [M+H]$^+$; 343 [M+Na]$^+$.

Example 61

Diethyl 5-hydroxy-4-methylpentenylphosphonate (53)

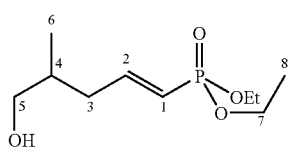

Total formula: C$_{10}$H$_{21}$O$_4$P
Yield=99%
R$_f$=0.42 (ethyl acetate).

NMR $^1$H (CDCL$_3$), δ(ppm): 0.92 (t, J$_{6-2}$ 6.7 Hz, 3H, H-6), 1.33 (m, 6H, H-8), 1.95-2.13 (m, 1H, H-4), 2.30-2.50 (m, 2H, H-3), 2.50 (s, 1H, OH), 3.46 (d, J$_{5-4}$ 5.5 Hz, 2H, H-5), 4.48-4.53 (m, 4H, H-7), 5.67 (tdd, J$_{1-3}$ 1.4 Hz, J$_{1-2}$ 17.1 Hz, J$_{1-P}$ 21.4 Hz, 1H, H-1), 6.75 (tdd, J$_{2-3}$ 7.1 Hz, J$_{2-1}$ 17.04 Hz, J$_{2-P}$ 21.8 Hz, 1H, H-2).

NMR $^{31}$P (CDCL$_3$), δ(ppm): 19.7.

NMR $^{13}$C (CDCL$_3$), δ(ppm): 16.68 (2C, C-8), 16.75 (1C, C-6), 35.50 (1C, C-4), 62.10 (d, J$_{3-P}$ 5.6 Hz, 1C, C-3), 62.08-62.13 (2C, C-7), 67.51 (1C, C-5), 118.52 (d, J$_{1-P}$ 187.4 Hz, 1C, C-1), 152.84 (d, J$_{2-P}$ 4.2 Hz 1C, C-2).

MS FAB>0 m/z (NOBA): 237 [M+H]$^+$; 259 [M+Na]$^+$.

Example 62

Diethyl 4-formylpentenylphosphonate (54)

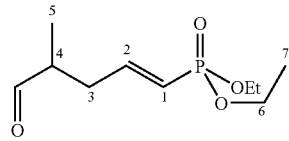

Total formula: C$_{10}$H$_{19}$O$_4$P
Yield=100%
R$_f$=0.55 (ethyl acetate).

NMR $^1$H (CDCL$_3$), δ(ppm): 1.11 (d, J$_{5-4}$ 7.1 Hz, 3H, H-5), 1.16-1.29 (m, 6H, H-7), 2.11-2.29 (m, 1H, H-4), 2.41-2.72 (m, 2H, H-3), 3.88-4.15 (m, 4H, H-6), 5.55-5.85 (m, 1H, H-1), 6.50-6.90 (m, 1H, H-2), 9.61 (d, J$_{formyl-4}$ 1.1 Hz, 1H, H-formyl).

NMR $^{31}$P (CDCL$_3$), δ(ppm): 18.7.

NMR $^{13}$C (CDCL$_3$), δ(ppm): 13.65 (1C, C-5), 16.72-16.78 (2C, C-7), 35.15 (d, J$_{3-p}$ 22.5 Hz, 1C, C-3), 45.42 (1C, C-4), 62.10-62.16 (2C, C-6), 120.30 (d J$_{1-P}$ 187.4 Hz, 1C, C-1), 149.94 (d, J$_{2-P}$ 4.8 Hz, 1C, C-2); 203.38 (1C, C-formyl).

MS FAB>0 m/z (NOBA): 235 [M+H]$^+$; 257 [M+Na]$^+$.

Example 63

4-Formylpentenylphosphonic acid (55)

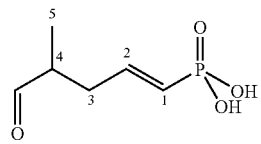

Total formula: C$_6$H$_{11}$O$_4$P
Yield=66%
R$_f$=0.41 (5:5, 27% ammonia:isopropanol).

NMR $^1$H (Acetone d$_6$), δ(ppm): 1.12 (d, J$_{6-2}$ 7.1 Hz, 3H, H-5), 2.18-2.38 (m, 1H, H-4), 2.50-2.74 (m, 2H, H-3), 5.85-6.03 (m, 1H, H-1), 6.48-6.80 (m, 1H, H-2), 9.69 (d, J$_{formyl-4}$ 0.8 Hz, 1H, H-formyl).

NMR $^{31}$P (Acetone d$_6$), δ(ppm): 18.9.

NMR $^{13}$C (Acetone d$_6$), δ(ppm): 12.74 (1C, C5), 34.62 (d, J$_{3-P}$ 22.8 Hz, 1C, C-3), 36.88 (1C, C-4), 122.79 (d, J$_{1-P}$ 188.3 Hz, 1C, C-1), 147.11 (d, J$_{2-P}$ 4.2 Hz, 1C, C-2); 203.76 (1C, C-formyl).

MS FAB>0 m/z (NOBA): 179 [M+H]$^+$; 201 [M+Na]$^+$.

Example 64

Preparation of triammonium 4-formylpentenylpyrophosphonate (56)

Preparation of Activated Phosphonic Anhydride:

To 2-methyl-5-phosphonopent-4-enal (0.3 g, 1.27 mmol, 1 eq) dissolved in 20 ml of methanol, n-trioctylamine (0.45 g, 1.27 mmol, 1 eq) is added. The reaction mixture is stirred magnetically at ambient temperature for 30 min, the solvent is then evaporated and the water traces co-evaporated three times with 10 ml of anhydrous pyridine. To the phosphonic tributylammonium salt obtained in this way dissolved in 18 ml of anhydrous THF, diphenylphosphate chloride (0.34 g, 1.27 mmol, 1 eq) and n-trioctylamine (1.34 g, 3.81 mmol, 3 eq) are then added respectively. The mixture is kept under magnetic stirring, at ambient temperature and in a nitrogen atmosphere for two hours.

Preparation of Orthophosphate N-Trioctylammonium Mono-Salt:

To orthophosphoric acid (0.37 g, 3.81 mmol, 3 eq) dissolved in 20 ml of methanol, n-trioctylamine (1.34 g, 3.81 mmol, 3 eq) is added. The mixture is stirred magnetically at ambient temperature for two hours. The methanol is then evaporated and water traces co-evaporated three times with 10 ml of anhydrous pyridine.

Coupling Reaction:

To the orthophosphate n-trioctylammonium mono-salt (1.71 g, 3.81 mmol, 3 eq) dissolved in 40 ml of anhydrous pyridine, activated phosphonic anhydride is added slowly (1.41 ml/hour). The mixture is kept under magnetic stirring and in a nitrogen atmosphere for 15 hours, the solvents are then evaporated and the residual oil undergoes silica gel chromatography (4:6, 27% ammonia:isopropanol).

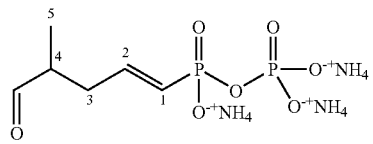

Total formula: $C_6H_{21}N_3O_7P_2$
Yield=60%
$R_f$=0.35 (7:5, 27% ammonia:isopropanol).

NMR $^1$H (D$_2$O), δ(ppm): 0.82 (d, $J_{5-4}$ 6.8 Hz, 3H, H-5), 1.80-2.35 (m, 3H, H-3 and H-4), 5.53-5.83 (m, 1H, H-1), 6.25-6.65 (m, 1H, H-2), 9.38-9.52 (m, 1H, H-formyl).

NMR $^{31}$P(D$_2$O), δ(ppm): -5.7 (d, Jβ-α23.5 Hz, 1P, P-β), 5.7 (d, $J_{β-α}$23.5 Hz, 1P, P-α).

NMR $^{13}$C (D$_2$O), δ(ppm): 13.33 (1C, C-5), 36.46 (d, $J_{3-P}$ 22.2 Hz, 1C, C-3), 93.59 (1C, C-4), 120.83 (d, $J_{1-P}$ 180.6 Hz, 1C, C-1), 149.81 (1C, C-2), 209.97 (1C, C-formyl).

MS FAB>0 m/z (GT): 259 [M−3NH$_4$+4H]$^+$.

Example 65

General Allyl Alcohol Bromination Conditions with Phosphorus Tribromide

To the alcohol (57.63 mmol, 1 eq) dissolved in 50 ml of dichloromethane, phosphorus tribromide (28.81 mmol, 0.5 eq) diluted in 10 ml of the same solvent at −20° C. is added. The reaction mixture is kept under magnetic stirring and in a nitrogen atmosphere for 3 hours.

After hydrolysis with 50 ml of distilled water at −40° C., the organic phase is extracted with ethyl ether (3×50 ml), washed with a saturated sodium chloride solution (3×50 ml), dried on sodium sulphate and concentrated.

Example 66

1-Bromo-3-methylbut-2-ene (57)

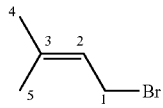

Total formula: $C_6BrH_9$
Yield=82%
$R_f$=0.8 (petroleum ether).

NMR $^1$H (CDCL$_3$), δ(ppm): 1.75 (s, 3H, CH$_3$); 1.8 (s, 3H, CH$_3$); 4.05 (d, $J_{1-2}$ 8.5 Hz, 2H, H-1); 5.55 (t, 1H, H-2).

Example 67

1-Bromo-3,7-dimethyldeca-2,6-diene (58)

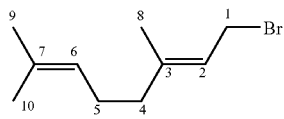

Total formula: $C_{10}BrH_{17}$
Yield=96%
$R_f$=0.8 (1:9 ethyl ether:petroleum ether).

NMR $^1$H (CDCL$_3$), δ(ppm): 1.64 (s, 3H, CH$_3$); 1.71 (s, 3H, CH$_3$); 1.75 (s, 3H, CH$_3$); 2.05-2.2 (m, 4H, H-4 and H-5); 4.05 (d, $J_{1-2}$ 8.4 Hz, 2H, H-1); 5.02-5.15 (m, 1H, H-6); 5.58 (t, 1H, H-2).

Example 68

4-Mesyl-2-methylbutene (59)

In a 250 ml flask, equipped with a magnetic stirrer and in a nitrogen atmosphere, 3-methylbut-3-enole (11.79 g, 137 mmol, 1 eq) dissolved in 100 ml of dichloromethane is added followed by triethylamine (20.81 g, 205.36 mmol, 1.5 eq) at −5° C. Mesyl chloride (17.25 g, 180.67 mmol, 1.1 eq) in solution in 20 ml of dichloromethane is then added over a 5 min period.

After 30 min of reaction, the temperature is increased to 25° C. and the organic phase washed with iced water (100 ml), 10% hydrochloric acid (100 ml) and with a saturated NaHCO$_3$ solution. After drying on sodium sulphate and evaporation of the dichloromethane, a colourless oil is obtained.

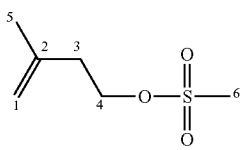

Total formula: $C_6H_{12}O_3S$

Yield=99%

$R_f$=0.5 (4:6 ethyl ether:petroleum ether).

NMR $^1$H (CDCL$_3$), δ(ppm): 1.8 (s, 3H, H-5); 2.48 (t, $J_{3-4}$ 6.7 Hz, 2H, H-3); 3.03 (s, 3H, H-6); 4.35 (t, 2H, H-4); 4.8 (s, 1H, H-1); 4.9 (s, 1H, H-1).

Example 69

4-Bromo-2-methylbutene (600)

To a lithium bromide solution (15 g, 182 mmol, 2 eq) in 150 ml of reflux-heated N,N-dimethylformamide, under magnetic stirring and in a nitrogen atmosphere, 4-mesyl-2-methylbutene (13.47 g, 91 mmol, 1 eq) is added.

After 2 hours of reaction, 150 ml of water is added. The organic phase is extracted with ethyl ether. The ethereal phases are collected and washed with a saturated sodium chloride solution (2×100 ml). After settling, the organic phase is dried on sodium sulphate, and concentrated to obtain a yellowish oil.

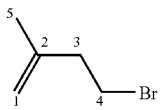

Total formula: $C_6BrH_9$

Yield=100%

$R_f$=0.8 (petroleum ether).

NMR $^1$H (CDCL$_3$), δ(ppm): 1.7 (s, 3H, H-5); 2.52 (t, $J_{3-4}$ 7.35 Hz, 2H, H-3); 3.44 (t, 2H, H-4); 4.7 (s, 1H, H-1); 4.8 (s, 1H, H-1).

Example 70

General Prenyl Bromide Phosphonation Conditions with Diethyl Methylphosphonate To diethyl methylphosphonate (14.75 mmol, 1.1 eq) in solution in 50 ml of tetrahydrofuran, 1.6 M n-butyllithium in hexane (16.09 mmol, 1.2 eq) is added drop by drop at −78° C. The mixture is stirred magnetically in a nitrogen atmosphere for one hour and the brominated compound (13.41 mmol, 1 eq) is then added.

After four hours of reaction, the reaction mixture is diluted in 50 ml of ethyl ether, washed three times with a hydrochloric acid solution (1N) and with a saturated sodium chloride solution (2×50 ml), dried on sodium sulphate, concentrated and undergoes silica gel chromatography (eluent=ethyl acetate).

Example 71

Diethyl 4-methylpent-3-enylphosphonate (61)

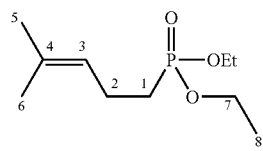

Total formula: $C_{10}H_{21}O_3P$

Yield=59%

$R_f$=0.4 (ethyl acetate).

NMR $^1$H (CDCL$_3$), δ(ppm): 1.33 (t, $J_{8-7}$ 6.7 Hz, 6H, H-8); 1.62 (s, 3H, CH$_3$); 1.65-1.88 (m, 2H, H-2); 1.69 (s, 3H, CH$_3$); 2.13-2.35 (m, 2H, H-1); 3.97-4.2 (qd, 4H, H-7); 5.0-5.18 (m, 1H, H-3).

NMR $^{31}$P (CDCL$_3$), δ(ppm): 33.2.

NMR $^{13}$C (CDCL$_3$), δ(ppm): 16.61-16.70 (2C, C-8); 18.44 (1C, C-5); 21.99 (d, $J_{2-P}$ 4.1 Hz, 1C, C-2); 25.11 (1C, C-6); 26.61 (d, $J_{1-P}$ 138.3 Hz, 1C, C-1); 61.80-61.89 (2C, C-7); 122.63 (d, $J_{3-P}$ 18.3 Hz, 1C, C-3); 133.69 (1C, C-4).

MS FAB>0 m/z (NOBA): 221 [M+H]$^+$.

Example 72

Diethyl (E)-4,8-dimethylnona-3,7-dienylphosphonate (62)

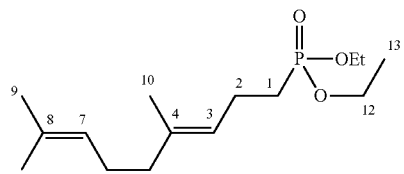

Total formula: $C_{15}H_{29}O_3P$

Yield=70%

$R_f$=0.5 (ethyl acetate).

NMR $^1$H (CDCL$_3$), δ(ppm): 1.31 (t, J13-12 7.1 Hz, 6H, H-13); 1.58 (s, 3H, H-11); 1.6 (s, 3H, CH$_3$); 1.65 (s, 3H, CH$_3$); 1.66-1.88 (m, 2H, H-2); 1.9-2.12 (m, 4H, H-5 and H-6); 2.18-2.38 (m, 2H, H-1); 3.97-4.18 (q, 4H, H-12); 5.06 (m, 1H, H-7); 5.1 (m, 1H, H-3).

NMR $^{31}$P (CDCL$_3$), δ(ppm): 33.2.

NMR $^{13}$C (CDCL$_3$), δ(ppm): 16.22-16.38 (2C, C-13); 16.91-18.08 (2C, C-10 and C-11); 21.39 (d, $J_{2-P}$ 4.6 Hz, 1C, C-2); 26.08 (1C, C-9); 26.35 (d, $J_{1-P}$ 138.8 Hz, 1C, C-1); 22.97 (1C, C-6); 39.97 (1C, C-5); 61.78-61.85 (2C, C-12); 123.41 (d, $J_{3-P}$ 17.3 Hz, 1C, C-3); 123.82 (1C, C-7); 131.88 (1C, C-8); 136.76 (1C, C-4).

MS FAB>0 m/z (NOBA): 289 [M+H]$^+$.

Example 73

Diethyl 4-methylpent-4-enylphosphonate (63)

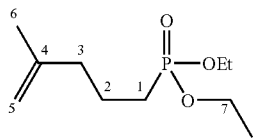

Total formula: $C_{10}H_{21}O_3P$

Yield=64%

$R_f$=0.35 (ethyl acetate).

NMR $^1$H (CDCL$_3$), δ(ppm): 1.31 (t, $J_{8-7}$ 3.5 Hz, 6H, H-8); 1.72 (s, 3H, H-6); 1.6-1.82 (m, 4H, H-2 and H-3); 2.1 (m, 2H, H-1); 4.0-4.20 (q, 4H, H-7); 4.7 (s, 1H, H-5); 4.76 (s, 1H, H-5).

NMR $^{31}$P (CDCL$_3$), δ(ppm): 33.7.

NMR $^{13}$C (CDCL$_3$), δ(ppm): 16.63-16.72 (2C, C-8); 21.64 (d, $J_{2-P}$ 4.4 Hz, 1C, C-2); 21.98 (1C, C-6); 27.41 (d, $J_{1-P}$ 131.7 Hz, 1C, C-1); 34.78 (d, $J_{3-P}$ 16.5 Hz, 1C, C-3); 61.82-61.93 (2C, C-7); 110.78 (1C, C-5); 148.13 (1C, C-4).

MS FAB>0 m/z (NOBA): 221 [M+H]$^+$.

Example 74

4-Methylpent-3-enylphosphonic acid (64)

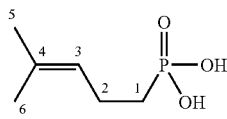

Total formula: $C_6H_{13}O_3P$

Yield=69%

$R_f$=0.29 (4:6, 27% ammonia: isopropanol).

NMR $^1$H (CDCL$_3$), δ(ppm): 1.61 (s, 3H, H-5); 1.65-1.88 (m, 2H, H-2); 1.68 (s, 3H, H-6); 2.15-2.32 (m, 2H, H-1); 5.04-5.2 (m, 1H, H-3); 8.0 (s, 2H, POH).

NMR $^{31}$P (CDCL$_3$), δ(ppm): 34.5.

NMR $^{13}$C (CDCL$_3$), δ(ppm): 18.05 (1C, C-5); 21.81 (d, $J_{2-P}$ 4.1 Hz, 1C, C-2); 24.76 (1C, C-6); 26.87 (d, $J_{1-P}$ 142.3 Hz, 1C, C-1); 122.51 (d, $J_{3-P}$ 19.5 Hz, 1C, C-3); 133.75 (1C, C-4).

MS FAB>0 m/z (NOBA): 165 [M+H]$^+$; 187 [M+Na]$^+$.

Example 75

(E)-4,8-dimethylnona-3,7-dienylphosphonic acid (65)

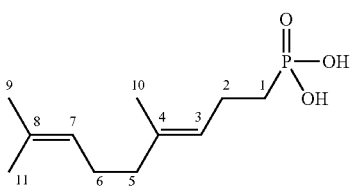

Total formula: $C_{11}H_{21}O_3P$

Yield=98%

$R_f$=0.4 (4:6, 27% ammonia: isopropanol).

NMR $^1$H (CDCL$_3$), δ(ppm): 1.55-1.88 (m, 2H, H-2); 1.62 (s, 6H, 2CH$_3$); 1.7 (s, 3H, CH$_3$); 1.9-2.1 (m, 4H, H-5 and H-6); 2.17-2.41 (m, 2H, H-1); 5.0-5.22 (m, 2H, H-3 and H-7); 9.45 (s, 2H, POH).

NMR $^{31}$P (CDCL$_3$), δ(ppm): 36.8.

NMR $^{13}$C (CDCL$_3$), δ(ppm): 15.68-18.1 (2C, C-10 and C-11); 21.25 (d, $J_{2-P}$ 4.5 Hz, 1C, C-2); 26.10 (1C, C-9); 26.6 (d, $J_{1-P}$ 142.9 Hz, 1C, C-1); 26.84 (1C, C-6); 39.99 (1C, C-5); 123.33 (d, $J_{3-P}$ 18.6 Hz, 1C, C-3); 124.58 (1C, C-7); 131.87 (1C, C-8); 136.8 (1C, C-4).

MS FAB>0 m/z (NOBA): 233 [M+H]$^+$; 255 [M+Na]$^+$.

Example 76

4-Methylpent-4-enylphosphonic acid (66)

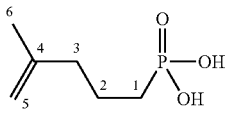

Total formula: $C_6H_{13}O_3P$

Yield=76%

$R_f$=0.4 (4:6, 27% ammonia: isopropanol).

NMR $^1$H (CDCL$_3$), δ(ppm): 1.73 (s, 3H, H-6); 1.6-1.85 (m, 4H, H-2 and H-3); 2.11 (m, 2H, H-1); 4.71 (s, 1H, H-5); 4.77 (s, 1H, H-5); 8.39 (s, H, POH).

NMR $^{31}$P (CDCL$_3$), δ(ppm): 37.78.

NMR $^{13}$C (CDCL$_3$), δ(ppm): 21.51 (d, $J_{2-P}$ 4.2 Hz, 1C, C-2); 21.73 (1C, C-6); 27.77 (d, $J_{1-P}$ 133.2 Hz, 1C, C-1); 38.61 (d, $J_{3-P}$ 17.5 Hz, 1C, C-3); 110.13 (1C, C-5); 147.63 (1C, C-4).

MS FAB>0 m/z (NOBA): 165 [M+H]$^+$; 187 [M+Na]$^+$.

Example 77

Triammonium 4-methylpent-3-enylpyrophosphonate (67)

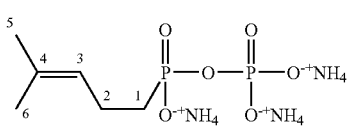

Total formula: $C_6H_{23}N_3O_6P_2$

Yield=50%

$R_f$=0.35 (4:6, 27% ammonia: isopropanol).

NMR $^1$H (D$_2$O), δ(ppm): 1.52 (s, 3H, H-5); 1.55-1.6 (m, 2H, H-2); 1.57 (s, 3H, H-6); 2.0-2.22 (m, 2H, H-1); 5.14 (m, 1H, H-3).

NMR $^{31}$P (D$_2$O), δ(ppm): −7.0 (d, $J_{β-α}$ 25.2 Hz, P-β); 19.5 (d, P-α).

NMR $^{13}$C (D$_2$O), δ(ppm): 17.24 (1C, C-5); 21.93 (d, $J_{2-P}$ 3.9 Hz, 1C, C-2); 24.02 (1C, C-6); 28.29 (d, $J_{1-P}$ 135.1 Hz, 1C, C-1); 124.87 (d, $J_{3-P}$ 18.8 Hz, 1C, C-3); 133.82 (d, $J_{4-P}$ 1.5 Hz, 1C, C-4).

MS FAB>0 m/z (GT): 279 [M−NH$_4$+2H]$^+$; 262 [M−2NH$_4$+3H]$^+$; 245 [M+3NH$_4$+4H]$^+$.

Example 78

Triammonium (E)-4,8-dimethylnona-3,7-dienylpyrophosphonate (68)

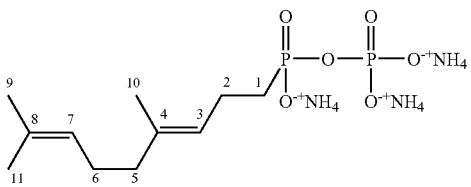

Total formula: $C_{11}H_{31}N_3O_6P_2$

Yield=46%

Rf=0.47 (4:6, 27% ammonia: isopropanol).

NMR $^1$H (D$_2$O), δ(ppm): 1.42 (s, 3H, H-11); 1.46 (s, 3H, CH$_3$); 1.49 s, 3H, CH$_3$); 1.5-1.65 (m, 2H, H-2); 1.73-1.95 (m, 4H, H-5 and H-6); 1.95-2.15 (m, 2H, H-1); 4.99 (m, 1H, H-7); 5.09 (m, 1H, H-3).

NMR $^{31}$P (D$_2$O), δ(ppm): −6.4 (d, $J_{β-α}$ 25.1 Hz, P-β); 19.3 (d, P-α).

NMR $^{13}$C (D$_2$O), δ(ppm): 15.56 (1C, C-10); 17.3 (1C, C-11); 21.99 (d, J2-P 4.4 Hz, 1C, C-2); 25.18 (1C, C-9); 26.15 (1C, C-6); 28.39 (d, $J_{1-P}$ 134.4 Hz, 1C, C-1); 39.15 (1C, C-5); 124.74 (1C, C-7); 125.08 (d, $J_{3-P}$ 18.8 Hz, 1C, C-3); 133.87 (1C, C-8); 136.8 (1C, C-4).

MS FAB>0 m/z (GT): 330 [M−2NH$_4$+5H]$^+$; 313 [M−3NH$_4$+4H]$^+$.

Example 79

Triammonium 4-Methylpent-4-enylpyrophosphonate (69)

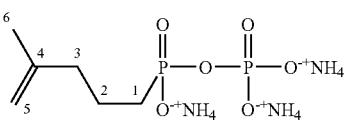

Total formula: $C_6H_{23}N_3O_6P_2$

Yield=52.15%

$R_f$=0.5 (4:6, 27% ammonia: isopropanol).

NMR $^1$H (D$_2$O), δ(ppm): 1.52-1.71 (m, 4H, H-2 and H-3); 1.62 (s, 3H, H-6); 2.0 (m, 2H, H-1); 4.66 (s, 1H, H-5); 4.7 (s, 1H, H-5).

NMR $^{31}$P (D$_2$O), δ(ppm): −7.0 (d, $J_{β-α}$ 25.1 Hz, P-β); 20.3 (d, P-α).

NMR $^{13}$C (D$_2$O), δ(ppm): 21.2 (d, $J_{2-P}$ 4.0 Hz, 1C, C-2); 21.86 (1C, C6); 27.67 (d, $J_{1-P}$ 136.7 Hz, 1C, C-1); 38.65 (d, $J_{3-P}$ 18.4 Hz, 1C, C-3); 110.03 (1C, C-5); 147.92 (1C, C-4).

MS FAB>0 m/z (GT): 262 [M−2NH$_4$+3H]$^+$; 245 [M−3NH$_4$+4H]$^+$.

Example 80

Tetraammonium 4-methylpent-3-enyltriphosphonate (70)

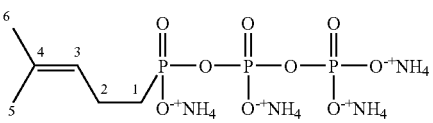

Total formula: $C_6H_{27}N_4O_9P_3$

Yield=15%

$R_f$=0.21 (4:6, 27% ammonia: isopropanol).

NMR $^1$H (D$_2$O), δ(ppm): 1.54 (s, 3H, H-5); 1.56-1.62 (m, 2H, H-2); 1.58 (s, 3H, H-6); 2.10-2.28 (m, 2H, H-1); 5.15 (m, 1H, H-3).

NMR $^{31}$P (D$_2$O), δ(ppm): −21.1 (dd, $J_{β-α}$ 24.0 Hz and $J_{β-γ}$ 19.6 Hz, P-β; −5.7 (d, P-γ); 21.9 (d, P-α).

NMR $^{13}$C (D$_2$O), δ(ppm): 17.20 (1C, C-5); 22.12 (d, $J_{2-P}$ 4.0 Hz, 1C, C-2); 24.10 (1C, C-6); 28.79 (d, $J_{1-P}$ 135.7 Hz, 1C, C-1); 124.96 (d, $J_{3-P}$ 18.9 Hz, 1C, C-3); 133.96 (1C, C-4).

MS FAB>0 m/z (GT): 325 [M−4NH$_4$+5]$^+$.

Example 81

Tetraammonium (E)-4,8-dimethylnona-3,7-dienyltriphosphonate (71)

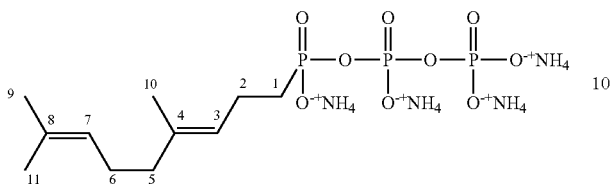

Total formula: $C_{11}H_{35}N_4O_9P_3$
Yield=9.61%
$R_f$=0.29 (4:6, 27% ammonia: isopropanol).
NMR $^1$H (D$_2$O), δ(ppm): 1.45 (s, 3H, CH$_3$); 1.48 (s, 3H, CH$_3$); 1.52 (s, 3H, CH$_3$); 1.54-1.69 (m, 2H, H-2); 1.77-1.99 (m, 4H, H-5 and H-6); 2.0-2.19 (m, 2H, H-1); 5.03 (m, 1H, H-7); 5.12 (s, 1H, H-3).
NMR $^{31}$P (D$_2$O), δ(ppm): −20.7 (dd, J$_{β-α}$ 23.9 Hz and J$_{β-γ}$ 20.6 Hz, P-β); −5.4 (d, P-γ); 21.4 (d, P-α).
NMR $^{13}$C (D$_2$O), δ(ppm): 15.51 (1C, C-10); 17.27 (1C, C-11); 21.78 (d, J$_{2-P}$ 3.8 Hz, 1C, C-2); 25.13 (1C, C-9); 26.10 (1C, C-6); 28.37 (d, J$_{1-P}$ 135.2 Hz, 1C, C-1); 39.09 (1C, C-5); 124.68 (d, J$_{3-P}$ 15.5 Hz, 1C, C-3); 124.73 (1C, C-7); 133.82 (1C, C-8); 137.06 (1C, C-4).
MS FAB>0 m/z (GT): 393 [M−4NH$_4$+5H]$^+$.

Example 82

Tetraammonium 4-methylpent-4-enyltriphosphonate (72)

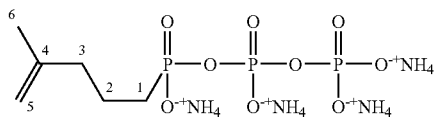

Total formula: $C_6H_{27}N_4O_9P_3$
Yield=14%
$R_f$=0.26 (4:6, 27% ammonia: isopropanol).
NMR $^1$H (D$_2$O), δ(ppm): 1.48-1.52 (m, 4H, H-2 and H-3); 1.58 (s, 3H, H-6); 1.98 (m, 2H, H-1); 4.62 (s, 1H, H-5); 4.7 (s, 1H, H-5).
NMR $^{31}$P (D$_2$O), δ(ppm): −21.0 (dd, J$_{β-α}$ 24.4 Hz and J$_{β-γ}$ 20.3 Hz, P-β); −5.9 (d, P-γ); 22.1 (d, P-α).
NMR $^{13}$C (D$_2$O), δ(ppm): 21.08 (d, J$_{2-P}$ 4.3 Hz, 1C, C-2); 21.83 (1C, C-6); 27.64 (d, J$_{1-P}$ 137.1 Hz, 1C, C-1); 38.45 (d, J$_{3-P}$ 18.3 Hz, 1C, C-3); 110.16 (1C, C-5); 147.59 (1C, C-4).
MS FAB>0 m/z (GT): 325 [M−4NH$_4$+5H]$^+$.

Example 83

Triammonium α,γ-(4-methylpent-3-enyl)triphosphonate (73)

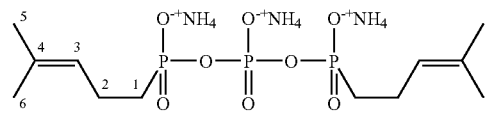

Total formula: $C_{12}H_{34}N_4O_8P_3$
Yield=4.2%
$R_f$=0.26 (4:6, 27% ammonia: isopropanol).
NMR $^1$H (D$_2$O), δ(ppm): 1.47 (s, 6H, H-6); 1.53 (s, 6H, H-5); 1.54-1.68 (m, 4H, H-2); 1.95-2.2 (m, 4H, H-1); 5.08 (m, 2H, H-3).
NMR $^{31}$P (D$_2$O), δ(ppm): −21.88 (t, J$_{β-α}$=J$_{β-γ}$ 25.5 Hz, P-β); 20.91 (d, 2P, P-α and P-γ).
NMR $^{13}$C (D$_2$O), δ(ppm): 17.24 (2C, C-5); 21.98 (d, J$_{2-P}$ 4.0 Hz, 2C, C-2); 25.11 (2C, C-6); 28.1 (d, J$_{1-P}$ 131.1 Hz, 2C, C-1); 124.72 (d, J$_{3-P}$ 21.2 Hz, 2C, C-3); 133.9 (d, J$_{4-P}$ 1.2 Hz, 2C, C-4).
MS FAB>0 m/z (GT): 391 [M−3NH$_4$+4H]$^+$.

Example 84

Triammonium α,γ-[(E)-4,8-dimethylnona-3,7-dienyl]-triphosphonate (74)

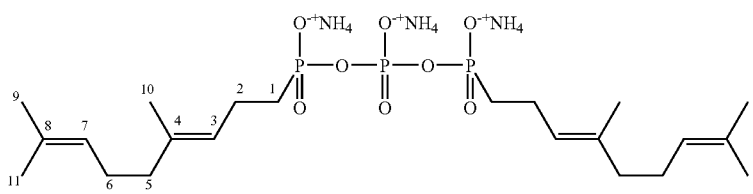

Total formula: $C_{22}H_{50}N_3O_8P_3$
Yield=5%
$R_f$=0.75 (4:6, 27% ammonia: isopropanol).
NMR $^1$H (D$_2$O), δ(ppm): 1.46 (s, 6H, H-11); 1.53 (s, 12H, H-9 and H-10); 1.69-2.0 (m, 8H, H-5 and H-6); 2.08-2.12 (m, 4H, H-1); 4.95-5.05 (m, 2H, H-7); 5.06-5.17 (m, 2H, H-3).
NMR $^{31}$P (D$_2$O), δ(ppm): −22.2 (t, J$_{β-α}$=J$_{β-γ}$ 25.6 Hz, 1P, P-β); 20.7 (d, 2P, P-α and P-γ).
NMR $^{13}$C (D$_2$O), δ(ppm): 15.53 (2C, C-10); 17.32 (2C, C-11); 21.85 (d, J$_{2-P}$ 3.8 Hz, 2C, C-2); 25.27 (2C, C-9); 26.18

(1C, C-6); 29.02 (d, $J_{1-P}$ 134.9 Hz, 2C, C-1); 40.18 (2C, C-5); 124.80 (d, $J_{3-P}$ 15.7 Hz, 2C, C-3); 124.81 (2C, C-7); 133.89 (2C, C-8); 137.10 (2C, C-4).

MS FAB>0 m/z (GT): 527 [M−3NH$_4$+4 H]$^+$.

Example 85

Triammonium
α,γ-(4-methylpent-4-enyl)triphosphonate (75)

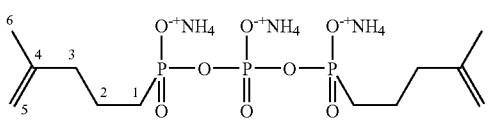

Total formula: $C_{12}H_{34}N_3O_8P_3$
Yield=12.5%
$R_f$=0.66 (4:6, 27% ammonia: isopropanol).
NMR $^1$H (D$_2$O), δ(ppm): 1.5-1.71 (m, 8H, H-2 and H-3); 1.62 (s, 6H, H-6); 2.01 (m, 4H, H-1); 4.67 (s, 2H, H-5); 4.70 (s, 2H, H-5).
NMR $^{31}$P (D$_2$O), δ(ppm): −22.1 (t, $J_{β-α}=J_{β-γ}$ 25.6 Hz, 1P, P-β); 21.7 (d, 2P, P-α and P-γ).
NMR $^{13}$C (D$_2$O), δ(ppm): 21.14 (d, $J_{2-P}$ 4.1 Hz, 2C, C-2); 21.85 (2C, C-6); 27.75 (d, $J_{1-P}$ 137.4 Hz, 2C, C-1); 38.52 (d, $J_{3-P}$ 18.7 Hz, 2C, C-3); 110.24 (2C, C-5); 147.55 (2C, C-4).
MS FAB>0 m/z (GT): 391 [M−3NH$_4$+4H]$^+$.

Example 86

General Phosphonation Conditions According to the Michaelis-Arbuzov Method

In a flask equipped with a cooler, a magnetic stirrer and in a nitrogen atmosphere, triethylphosphite (64 mmol, 1 eq) is introduced, the brominated compound (58 mmol, 1 eq) is then added and the reaction mixture is heated at 130° C. for 3 hours. The unprocessed reaction product is concentrate to eliminate the residual triethylphosphite and then undergoes silica gel chromatography (eluent=ether).

Example 87

Diethyl 3-methylbut-2-enylphosphonate (76)

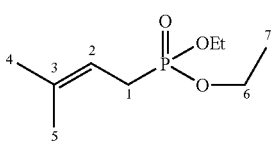

Total formula: $C_9H_{19}O_3P$
Yield=58%
$R_f$=0.45 (ethyl ether).
NMR $^1$H (CDCL$_3$), δ(ppm): 1.33 (t, $J_{7-6}$ 7.0 Hz, 6H, H-7); 1.67 (d, $J_{4-2}$ 3.9 Hz, 3H, H-4); 1.76 (d, $J_{5-2}$ 5.3 Hz, 3H, H-5); 2.57 (dd, $J_{1-P}$ 22.0 Hz, $J_{1-2}$ 7.5 Hz, 2H, H-1); 4.15 (q, 4H, H-6); 5.19 (m, 1H, H-2).
NMR $^{31}$P (CDCL$_3$), δ(ppm): 30.1.
NMR $^{13}$C (CDCL$_3$), δ(ppm): 16.55-16.61 (2C, C-7); 18.01 (d, $J_{5-P}$ 2.5 Hz, C-5); 25.85 (1C, C-4); 26.56 (d, $J_{1-P}$ 138.2 Hz, 1C, C-1); 61.78-61.85 (2C, C-6); 112.75 (d, $J_{2-P}$ 11.3 Hz, 1C, C-2); 136.62 (d, $J_{3-P}$ 14.5 Hz, 1C, C-3).
MS FAB>0 m/z (NOBA): 207 [M+H]$^+$.

Example 88

Diethyl 3-methylbut-3-enylphosphonate (77)

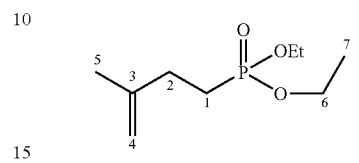

Total formula: $C_9H_{19}O_3P$
Yield=67%
$R_f$=0.43 (ethyl ether).
NMR $^1$H (CDCL$_3$), δ(ppm): 1.22-1.35 (t, $J_{7-6}$ 7.0 Hz, 6H, H-7); 1.73 (s, 3H, H-5); 1.77-1.95 (m, 2H, H-3); 2.20-2.37 (m, 2H, H-4); 4.00-4.18 (q, 4H, H-6); 4.60-4.77 (m, 2H, H-4).
NMR $^{31}$P (CDCL$_3$), δ(ppm): 20.6.
NMR $^{13}$C (CDCL$_3$), δ(ppm): 16.53-16.58 (2C, C-7); 22.29 (1C, C-5); 24.23 (d, $J_{1-P}$ 141.2 Hz, 1C, C-1); 30.28 (d, $J_{2-P}$ 4.3 Hz, 1C, C-2); 61.61 (2C, C-6); 110.34 (1C, C-4); 144.44 (d, $J_{3-P}$ 17.8 Hz, 1C, C-3).
MS FAB>0 m/z (NOBA): 207 [M+H]$^+$.

Example 89

Diethyl allylphosphonate (78)

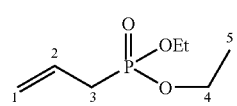

Total formula: $C_7H_{15}O_3P$
Yield=42%
$R_f$=0.39 (ethyl ether).
NMR $^1$H (CDCL$_3$), δ(ppm): 1.38 (t, $J_{5-4}$ 7.1 Hz, 6H, H-5); 2.63 (dd, $J_{3-2}$ 7.3 Hz, $J_{3-P}$ 22.0 Hz, 2H, H-3); 4.16 (qt, 4H, H-4); 5.15-5.30 (m, 2H, H-1); 5.73-5.82 (m, 1H, H-2).
NMR $^{31}$P (CDCL$_3$), δ(ppm): 28.4.
NMR $^{13}$C (CDCL$_3$), δ(ppm): 16.80-16.86 (2C, C-5); 32.19 (d, $J_{3-P}$ 139.4 Hz, 1C, C-3); 62.29-62.37 (2C, C-4); 120.31 (d, $J_{1-P}$ 14.5 Hz, 1C, C-1); 127.92 (d, $J_{2-P}$ 11.1 Hz, 1C, C-2).
MS FAB>0 m/z (NOBA): 179 [M+H]$^+$; 200 [M+Na]$^+$.

Example 90

3-Methylbut-2-enylphosphonic acid (79)

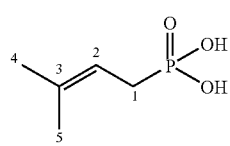

Total formula: $C_5H_{11}O_3P$
Yield=85%
$R_f$=0.33 (4:6, 27% ammonia: isopropanol).

NMR $^1$H (acetone-$d_6$), δ(ppm): 1.66-1.76 (m, 6H, H-4 and H-5); 2.55 (m, $J_{1-P}$ 20.0 Hz, 2H, H-1); 5.07-5.22 (m, 1H, H-2); 10.86 (s, 2H, POH).

NMR $^{31}$P (acetone-$d_6$), δ(ppm): 33.1.

NMR $^{13}$C (acetone-$d_6$), δ(ppm): 17.48 (1C, C-5); 25.46 (1C, C-4); 27.85 (d, $J_{1-P}$ 139.2 Hz, 1C, C-1); 114.28 (d, $J_{2-P}$ 10.9 Hz, 1C, C-2); 135.75 (d, $J_{3-P}$ 14.3 Hz, 1C, C-3).

MS FAB>0 m/z (NOBA): 151 [M+H]$^+$; 173 [M+Na]$^+$.

Example 91

3-Methylbut-3-enylphosphonic acid (80)

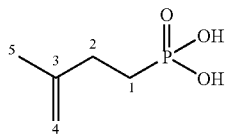

Total formula: $C_5H_{11}O_3P$
Yield=96%
$R_f$=0.32 (4:6, 27% ammonia: isopropanol).

NMR $^1$H (acetone-$d_6$), δ(ppm): 1.74 (s, 3H, H-5); 1.80-2.0 (m, 2H, H-2); 2.22-2.40 (m, 2H, H-1); 4.71-4.80 9m, 2H, H-4); 10.54 (s, 2H, POH).

NMR $^{31}$P (acetone-$d_6$), δ(ppm): 24.0.

NMR $^{13}$C (acetone-$d_6$), δ(ppm): 22.65 (1C, C-5); 26.98 (d, $J_{1-P}$ 147.3 Hz, 1C, C-1); 28.99 (d, $J_{2-P}$ 4.2 Hz, 1C, C-2); 110.68 (1C, C-4); 144.89 (d, $J_{3-P}$ 17.9 Hz, 1C, C-3).

MS FAB>0 m/z (NOBA): 151 [M+H]$^+$; 173 [M+Na]$^+$.

Example 92

Allylphosphonic Acid (81)

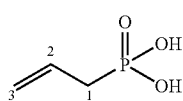

Total formula: $C_3H_7O_3P$
Yield=50%
$R_f$=0.29 (4:6, 27% ammonia: isopropanol).

NMR $^1$H (acetone-$d_6$), δ(ppm): 2.15 (dd, $J_{1-2}$ 7.53 Hz, $J_{1-P}$ 20.7 Hz, 2H, H-1); 4.84-4.95 (m, 2H, H-3); 5.45-5.70 (m, 1H, H-2); 10.53 (s, 2H, POH).

NMR $^{31}$P (acetone-$d_6$), δ(ppm): 28.3.

NMR $^{13}$C (acetone-$d_6$), δ(ppm): 27.70 (d, $J_{3-P}$ 135.2 Hz, 1C, C-3); 124.28 (d, $J_{1-P}$ 14.2 Hz, 1C, C-1); 132.11 (d, $J_{2-P}$ 10.1 Hz, 1C, C-2).

MS FAB>0 m/z (NOBA): 123 [M+H]$^+$.

Example 93

Triammonium 3-methylbut-2-enylpyrophosphonate (82)

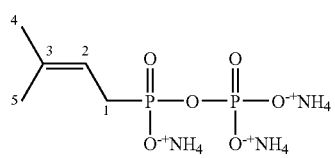

Total formula: $C_5H_{21}N_3O_6P_2$
Yield=61%
$R_f$=0.15 (5:5, 27% ammonia: isopropanol).

NMR $^1$H (D$_2$O), δ(ppm): 1.44 (d, $J_{4-2}$ 5.2 Hz, 3H, H-4); 1.55 (d, $J_{5-2}$ 3.8 Hz, 3H, H-5); 2.33 (dd, $J_{1-P}$ 21.7 Hz, $J_{1-2}$ 7.8 Hz, 2H, H-1); 5.02 (m, 1H, H-2).

NMR $^{31}$P (D$_2$O), δ(ppm): −7.0 (d, $J_{β-α}$ 26.0 Hz, P-β); 16.9 (d, P-α).

NMR $^{13}$C (D$_2$O), δ(ppm): 17.66 (1C, C-5); 25.42 (1C, C-4); 28.90 (d, $J_{1-P}$ 136.3 Hz, 1C, C-1); 114.91 (d, $J_{2-P}$ 10.8 Hz, 1C, C-2); 136.63 (d, $J_{3-P}$ 14.5 Hz, 1C, C-3).

MS FAB>0 m/z (GT): 231 [M−3NH$_4$+4]$^+$.

Example 94

Triammonium 3-methylbut-3-enylpyrophosphonate (83)

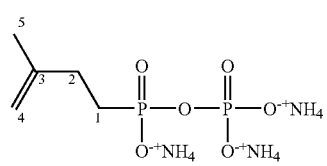

Total formula: $C_5H_{21}N_3O_6P_2$
Yield=61%
$R_f$=0.16 (4:6, 27% ammonia: isopropanol).

NMR $^1$H (D$_2$O), δ(ppm): 1.50 (s, 3H, H-5); 1.62-1.75 (m, 2H, H-2); 1.95-2.15 (m, 2H, H-1); 4.45-4.65 (m, 2H, H-5).

NMR $^{31}$P (D$_2$O), δ(ppm): −8.4 (d, $J_{β-α}$ 25.0 Hz, P-β); 21.2 (d, P-α).

NMR $^{13}$C (D$_2$O), δ(ppm): 21.78 (1C, C-5); 26.62 (d, $J_{1-P}$ 137.0 Hz, 1C, C-1); 31.15 (d, $J_{2-P}$ 3.9 Hz, 1C, C-2); 109.40 (1C, C-4); 147.75 (d, $J_{1-P}$ 18.5 Hz, 1C, C-3).

MS FAB>0 m/z (GT): 231 [M−3NH$_4$+4]$^+$.

Example 95

Triammonium allylpyro-phosphonate (84)

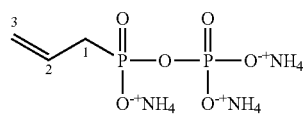

Total formula: C$_3$H$_{17}$N$_3$O$_6$P$_2$
Yield=40%
R$_f$=0.22 (5:5, 27% ammonia: isopropanol).
NMR $^1$H (D$_2$O), δ(ppm): 2.52 (dd, J$_{1-P}$ 21.7 Hz, J$_{1-2}$ 7.48 Hz, 2H, H-1); 4.92-5.12 (m, 2H, H-3); 5.62-5.90 (m, 1H, H-2).
NMR $^{31}$P (D$_2$O), δ(ppm): −6.8 (d, J$_{β-α}$ 24.3 Hz, P-β); 14.9 (d, P-α).
NMR $^{13}$C (D$_2$O), δ(ppm): 34.28 (d, J$_{1-P}$ 133.5 Hz, 1C, C-1); 118.54 (d, J$_{3-P}$ 13.9 Hz, 1C, C-3); 131.53 (d, J$_{2-P}$ 10.8 Hz, 1C, C-2).
MS FAB>0 m/z (GT): 203 [M−3NH$_4$+4H]$^+$.

Example 96

Tetraammonium 3-methylbut-3-enyltriphosphonate (85)

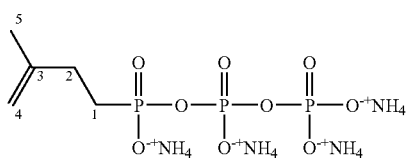

Total formula: C$_5$H$_{25}$N$_4$O$_9$P$_3$
Yield=15%
R$_f$=0.10 (5:5, 27% ammonia: isopropanol).
NMR $^1$H (D$_2$O), δ(ppm): 1.51 (s, 3H, H-5); 1.60-1.72 (m, 2H, H-2); 1.92-2.13 (m, 2H, H-1); 4.45-4.60 (2m, 2H, H-4).
NMR $^{31}$P (D$_2$O), δ(ppm): −21.2 (d, J$_{β-α}$ 24.0 Hz, Jβ-γ 21.2 Hz, P-β); −6.1 (d, P-γ); 21.3 (d, P-α).
NMR $^{13}$C (D$_2$O), δ(ppm): 21.83 (1C, C-5); 26.77 (d, J$_{1-P}$ 137.1 Hz, 1C, C-1); 31.21 (d, J$_{2-P}$ 3.9 Hz, 1C, C-2); 109.40 (1C, C-4); 147.82 (d, J$_{3-P}$ 18.5 Hz, 1C, C-3).
MS FAB>0 m/z (GT): 311 [M−4NH$_4$+51-1]$^+$.

Example 97

Tetraammonium allyltriphosphonate (86)

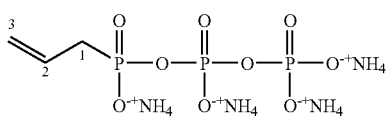

Total formula: C$_3$H$_{21}$N$_4$O$_9$P$_3$
Yield=10%
R$_f$=0.15 (5:5, 27% ammonia: isopropanol).
NMR $^1$H (D$_2$O), δ(ppm): 2.55 (dm, J$_{1-P}$ 21.9 Hz, J$_{1-2}$ 7.5 Hz, 2H, H-1); 5.00-5.17 (m, 2H, H-5); 5.60-5.90 (m, 1H, H-2).
NMR $^{31}$P (D$_2$O), δ(Ppm): −21.7 (m, P-β); −7.6 (m, P-γ); 16.6 (m, P-α).
NMR $^{13}$C (D$_2$O), δ(ppm): 34.81 (d, J$_{1-P}$ 128.9 Hz, 1C, C-1); 117.88 (d, J$_{3-P}$ 13.5 Hz, 1C, C-3); 131.96 (d, J$_{2-P}$ 10.7 Hz, 1C, C-2).
MS FAB>0 m/z (GT): 283 [M−4NH$_4$+5]$^+$.

Example 98

Triammonium α,γ-(3-methylbut-2-enyl)triphosphonate (87)

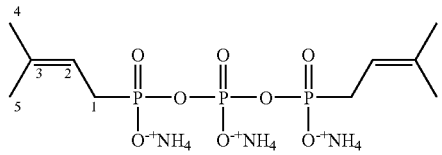

Total formula: C$_{10}$H$_{30}$N$_3$O$_8$P$_3$
Yield=17%
R$_f$=0.25 (5:5, 27% ammonia: isopropanol).
NMR $^1$H (D$_2$O), δ(ppm): 1.53 (m, 3H, H-4); 1.60 (m, 3H, H-5); 2.32-2.55 (m, J$_{1-P}$ 22.0 Hz, J$_{1-2}$ 7.7 Hz, 2H, H-1); 5.05-5.17 (m, 1H, H-2).
NMR $^{31}$P (D$_2$O), δ(ppm): −21.7 (t, J$_{β-α}$=J$_{β-γ}$ 26.0 Hz, P-β); 18.1 (d, 2P, P-α and P-γ).
NMR $^{13}$C (D$_2$O), δ(ppm): 17.45 (1C, C-5); 25.53 (1C, C-4); 28.76 (d, J$_{1-P}$ 135.7 Hz, 1C, C-1); 115.48 (d, J$_{2-P}$ 10.6 Hz, 1C, C-2); 136.04 (d, J$_{3-P}$ 14.3 Hz, 1C, C-3).
MS FAB>0 m/z (GT): 391 [M−3NH$_4$+4H]$^+$.

Example 99

Triammonium α,γ-allyltriphosphonate (88)

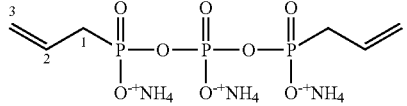

Total formula: C$_6$H$_{22}$N$_3$O$_8$P$_3$
Yield=6%
R$_f$=0.45 (5:5, 27% ammonia: isopropanol).
NMR $^1$H (D$_2$O), δ(ppm): 2.30-2.60 (m, 2H, H-1); 4.92-5.12 (m, 2H, H-2); 5.50-5.80 (2m, 1H, H-3).
NMR $^{31}$P (D$_2$O), δ(ppm): −22.5 (t, J$_{β-α}$=J$_{β-γ}$ 25.0 Hz, P-β); 16.2 (d, 2P, P-α and P-γ).
NMR $^{13}$C (D$_2$O), δ(ppm): 34.25 (d, J$_{1-P}$ 133.0 Hz, 1C, C-1); 118.24 (d, J$_{3-P}$ 13.8 Hz, 1C, C-3); 131.6 (d, J$_{2-P}$ 10.7 Hz, 1C, C-2).
MS FAB>0 m/z (GT): 307 [M−3NH$_4$+4]$^+$.

Example 100

Diammonium α,β-(3-methylbut-2-enyl)phosphonate (89)

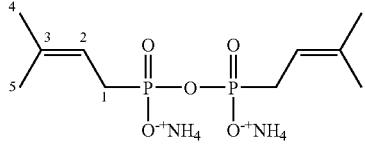

Total formula: $C_{10}H_{30}N_2O_4P_3$
Yield=13%
$R_f$=0.46 (5:5, 27% ammonia: isopropanol).
NMR $^1$H (D$_2$O), δ(ppm): 1.54 (m, 3H, H-4); 1.60 (m, 3H, H-5); 2.50 (m, $J_{1\text{-}P}$ 21.0 Hz, $J_{1\text{-}2}$ 7.8 Hz, 2H, H-1); 5.03-5.20 (m, 1H, H-2).
NMR $^{31}$P (D$_2$O), δ(ppm): 17.3.
NMR $^{13}$C (D$_2$O), δ(ppm): 17.61 (1C, C-5); 25.41 (1C, C-4); 29.43 (d, $J_{1\text{-}P}$ 144.4 Hz, 1C, C-1); 115.33 (d, $J_{5\text{-}P}$ 10.7 Hz, 1C, C-2); 136.62 (d, $J_{3\text{-}P}$ 14.5 Hz, 1C, C-3).
MS FAB>0 m/z (GT): 305 [M−2NH$_4$+Na+2H]$^+$; 283 [M−2NH$_4$+Na+3H]$^+$.

Example 101

Diammonium α,β-(3-methylbut-3-enyl)phosphonate (90)

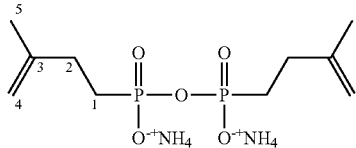

Total formula: $C_{10}H_{30}N_2O_4P_3$
Yield=10%
$R_f$=0.50 (5:5, 27% ammonia: isopropanol).
NMR $^1$H (D$_2$O), δ(ppm): 1.65 (s, 3H, H-5); 1.70-1.80 (m, 2H, H-2); 2.10-2.15 (m, 2H, H-1); 4.68 (2m, 2H, H-4).
NMR $^{31}$P (D$_2$O), δ(ppm): 20.0.
NMR $^{13}$C (D$_2$O), δ(ppm): 21.80 (2C, C-5); 26.63 (d, $J_{1\text{-}P}$ 137.0 Hz, 2C, C-1); 31.14 (d, $J_{2\text{-}P}$ 4.0 Hz, 2C, C-2); 109.32 (2C, C-4); 147.71 (d, $J_{3\text{-}P}$ 18.5 Hz, 2C, C-3).
MS FAB>0 m/z (GT): 303 [M−2NH$_4$+Na]$^+$; 281 [M−2NH$_4$+H]$^+$.

Example 102

Diammonium α,β-allylpyrophosphonate (91)

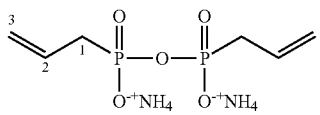

Total formula: $C_6H_{18}N_2O_5P_2$
Yield=6%
$R_f$=0.55 (5:5, 27% ammonia: isopropanol).
NMR $^1$H (D$_2$O), δ(ppm): 2.35-2.57 (m, 2H, H-1); 4.95-5.15 (m, 2H, H-3); 5.55-5.85 (2m, 1H, H-2).
NMR $^{31}$P (D$_2$O), δ(ppm): 15.6.
NMR $^{13}$C (D$_2$O), δ(ppm): 34.73 (d, $J_{1\text{-}P}$ 132.7 Hz, 1C, C-1); 117.96 (d, $J_{3\text{-}P}$ 13.5 Hz, 1C, C-3); 132.02 (d, $J_{2\text{-}P}$ 10.7 Hz, 1C, C-2).
MS FAB>0 m/z (GT): 227 [M−2NH$_4$+3H]$^+$.

Example 103

Diethyl 5-hydroxy-4-methylpentylphosphonate (92) preparation method

Diethyl 4-methylbut-4-enylphosphonate (2.2 g, 100 mmol, 1 eq) dissolved in 2 ml of THF is cooled to 0° C. A BH$_3$-Me$_2$-S (2 M) solution in THF (1.67 ml, 3.33 mmol, 0.33 eq) is then added slowly. The mixture is allowed to return to ambient temperature. The reaction continues for 2 hours. It is cooled again to 0° C. and 35% hydrogen peroxide (0.97 g, 10 mmol, 1 eq) is added slowly. After 30 minutes of reaction, 20 ml of water is added. After three extractions with ethyl ether (3×100 ml), the organic phase is washed with a saturated NaCl solution, dried on sodium sulphate and concentrated. The residual oil obtained in this way is purified by silica gel chromatography (Ethyl acetate).

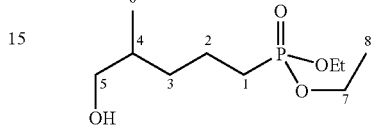

Total formula: $C_{10}H_{23}O_4P$
Yield=70%
$R_f$=0.27 (Ethyl acetate).
NMR $^1$H (CDCL$_3$), δ(ppm): 0.95 (d, $J_{6\text{-}4}$ 6.6 Hz, 3H, H-6); 1.10-1.35 (m, 3H, H-8); 1.40-1.90 (m, 6H, H-1, H-2 and H-3); 2.05-2.40 (m, 1H, H-4); 3.80 (d, $J_{5\text{-}4}$ 5.9 Hz, 2H, H-5); 4.0-4.23 (m, 4H, H-7).
NMR $^{31}$P (CDCL$_3$), δ(ppm): 33.7.
NMR $^{13}$C (CDCL$_3$), δ(ppm): 16.84 (1C, C-6); 16.86-16.92 (2C, C-7); 20.29 (d, $J_{2\text{-}P}$ 4.9 Hz, 1C, C-2); 26.23 (d, $J_{1\text{-}P}$ 139.1 Hz, 1C, C-1); 34.38 (d, $J_{3\text{-}P}$ 16.0 Hz, 1C, C-3); 35.78 (1C, C-4); 61.85-61.91 (2C, C-7); 68.19 (1C, C-5).
MS FAB>0 m/z (NOBA): 239 [M+H]$^+$; 261 [M+Na]$^+$.

Example 104

Diethyl 4-formylpentylphosphonate (93)

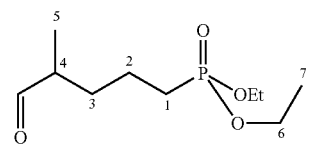

Total formula: $C_{10}H_{21}O_4P$
Yield=100%
$R_f$=0.40 (Ethyl acetate).
NMR $^1$H (CDCL$_3$), δ(ppm): 1.10 (d, $J_{5\text{-}4}$ 7.1 Hz, 3H, H-5); 1.26-1.70 (m, 6H, H-7); 1.40-1.90 (m, 6H, H-1, H-2 and H-3); 2.25-2.50 (m, 1H, H-4); 4.0-4.30 (m, 4H, H-6); 9.62 (d, $J_{formyl\text{-}4}$ 1.8 Hz, 1H, H-formyl).
NMR $^{31}$P (CDCL$_3$), δ(ppm): 32.8.
NMR $^{13}$C (CDCL$_3$), δ(ppm): 14.62 (1C, C-5); 16.89-16.92 (2C, C-7); 20.59 (d, $J_{2\text{-}P}$ 5.1 Hz, 1C, C-2); 25.85 (d, $J_{1\text{-}P}$ 141.0 Hz, 1C, C-1); 31.58 (d, $J_{3\text{-}P}$ 16.8 Hz, 1C, C-3); 46.39 (1C, C-4); 62.80 (2C, C-6); 204.96 (1C, C-formyl).
MS FAB>0 m/z (NOBA): 237 [M+H]$^+$; 259 [M+Na]$^+$.

Example 105

4-Formylpentylphosphonic acid (94)

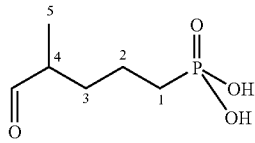

Total formula: $C_6H_{13}O_4P$
Yield=60%
$R_f$=0.49 (8:2, 27% ammonia: isopropanol).
NMR $^1$H (acetone-d$_6$), δ(ppm): 0.90 (d, $J_{5-4}$ 6.5 Hz, 3H, H-5); 1.40-1.91 (m, 6H, H-1, H-2 and H-3); 2.32-2.60 (m, 1H, H-4); 9.66 (d, $J_{formyl-4}$ 1.4 Hz, 1H, H-formyl).
NMR $^{31}$P (acetone-d$_6$), δ(ppm): 32.9.
NMR $^{13}$C (acetone-d$_6$), δ(ppm): 13.54 (1C, C-5); 20.57 (1C, C-2); 27.51 (d, $J_{1-P}$ 137.6 Hz, 1C, C-1); 32.92 (d, $J_{3-P}$ 12.3 Hz, 1C, C-3); 36.93 (1C, C-4); 204.46 (1C, C-formyl).
MS FAB>0 m/z (NOBA): 181 [M+H]$^+$; 203 [M+Na]$^+$.

Example 106

Triammonium 4-formylpentylphosphonate (95)

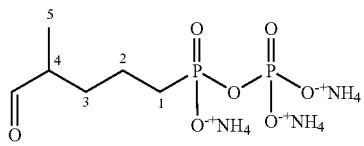

Total formula: $C_6H_{23}O_7P_2$
Yield=50%
$R_f$=0.39 (8:2, 27% ammonia: isopropanol).
NMR $^1$H (D$_2$O), δ(ppm): 0.77 (d, $J_{5-4}$ 5.5 Hz, 3H, H-5); 1.38-1.82 (m, 6H, H-1, H-2 and H-3); 2.27-2.58 (m, 1H, H-4); 9.40 (d, $J_{formyl-4}$ 1.8 Hz, 1H, H-formyl).
NMR $^{31}$P (D$_2$O), δ(ppm): −5.9 (d, $J_{β-α}$ 25.2 Hz, P-β); 19.3 (d, P-α).
NMR $^{13}$C (D$_2$O), δ(ppm): 13.64 (1C, C-5); 20.90 (1C, C-2); 29.56 (d, $J_{1-P}$ 137.1 Hz, 1C, C-1); 33.97 (d, $J_{3-P}$ 12.2 Hz, 1C, C-3); 35.84 (1C, C-4); 204.21 (1C, C-formyl).
MS FAB>0 m/z (NOBA): 261 [M−3NH$_4$+4H]$^+$.

Example 107

Diethyl 4-methyl-2oxa-pent-4-enylphosphonate (96)

Diethyl hydroxymethylphosphonate (3 g, 17.8 mmol, 1 eq) is dissolved in 50 ml of THF to which sodium hydride (0.43 g, 17.8 mmol, 1 eq) is added. 1-chloro-2-methylpropene (1.62 g, 17.8 mmol, 1 eq) is then added. After one hour under magnetic stirring, at ambient temperature and in a nitrogen atmosphere, hydrolysis is performed with 100 ml of water. Extraction is performed with ether (3×50 ml). The organic phases are collected, washed with 100 ml of a saturated sodium chloride solution and dried on sodium sulphate. After evaporation of the solvent, the residual oil obtained is purified by silica gel chromatography (Eluent=ethyl acetate).

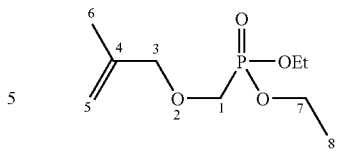

Total formula: $C_9H_{19}O_4P$
Yield=95%
$R_f$=0.40 (ethyl acetate).
NMR $^1$H (CDCl$_3$), δ(ppm): 1.22-1.35 (t, $J_{8-7}$ 7.7 Hz, 6H, H-8); 1.88 (s, 3H, H-6); 3.67-3.77 (d, $J_{1-P}$ 9.0 Hz, 2H, H-1); 4.0-4.10 (m, 2H, H-3); 4.10-4.18 (d, 4H, H-7); 4.90-5.02 (m, 2H, H-5).
NMR $^{31}$P (CDCl$_3$), δ(ppm): 20.6.
NMR $^{13}$C (2 (CDCl$_3$), δ(ppm): 16.82-16.88 (2C, C-8); 19.63 (1C, C-6); 62.73-62.80 (2C, C-7); 63.71 (d, $J_{1-P}$ 167.3 Hz, 1C, C-1); 77.34 (d, $J_{3-P}$ 13.1 Hz, 1C, C-3); 114.10 (1C, C-5); 141.35 (1C, C-4).
MS FAB>0 m/z (NOBA): 223 [M+H]$^+$.

Example 108

4-Methyl-2oxa-pent-4-enylphosphonic acid (97)

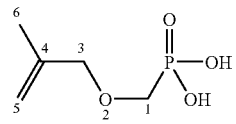

Total formula: $C_5H_{11}O_4P$
Yield=99%
$R_f$=0.29 (4:6, 27% ammonia: isopropanol).
NMR $^1$H (acetone-d$_6$), δ(ppm): 1.88 (s, 3H, H-6); 3.67-3.77 (m, 2H, H-1); 4.0-4.10 (m, 2H, H-3); 4.90-5.02 (m, 2H, H-5); 10.69 (s, 2H, POH).
NMR $^{31}$P (acetone-d$_6$), δ(ppm): 23.6.
NMR $^{13}$C (2 (acetone-d$_6$), δ(ppm): 19.00 (1C, C-6); 64.78 (d, $J_{1-P}$ 165.1 Hz, 1C, C-1); 76.56 (d, $J_{3-P}$ 11.7 Hz, 1C, C-3); 112.64 (1C, C-5); 142.21 (1C, C-4).
MS FAB>0 m/z (NOBA): 167 [M+H]$^+$.

Example 109

Triammonium 4-methyl-2oxapent-4-enylpyrophosphonate (98)

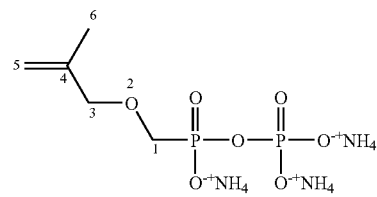

Total formula: $C_5H_{21}N_3O_7P_2$
Yield=41%
$R_f$=0.25 (5:5, 27% ammonia: isopropanol).
NMR $^1$H (D$_2$O), δ(ppm): 1.60 (s, 3H, H-6); 3.59 (d, $J_{1-P}$ 8.8 Hz, 2H, H-1); 3.92 (s, 2H, H-3); 4.83-4.92 (m, 2H, H-5).

NMR $^{31}$P (D$_2$O), δ(ppm): −6.3 (d, J$_{β-α}$ 25.0 Hz, P-β); 8.7 (d, P-α).

NMR $^{13}$C (D$_2$O), δ(ppm): 20.52 (1C, C-6); 67.71 (d, J$_{1-P}$ 162.9 Hz, 1C, C-1); 78.18 (d, J$_{3-P}$ 11.3 Hz, 1C, C-3); 114.85 (1C, C-5); 143.99 (1C, C-4).

MS FAB>0 m/z (GT): 247 [M−3NH$_4$+4H]$^+$.

Example 110

Tetraammonium
4-methyl-2oxa-pent-4-enyltriphosphonate (99)

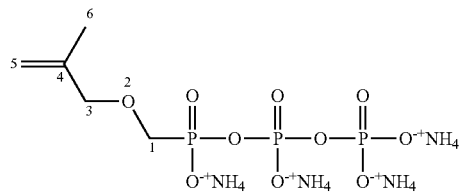

Total formula: C$_5$H$_{25}$N$_4$O$_{10}$P$_3$
Yield=15%
R$_f$=0.14 (5:5, 27% ammonia: isopropanol).
NMR $^1$H (D$_2$O), δ(ppm): 1.62 (s, 3H, H-6); 3.67-3.77 (d, J$_{1-P}$ 10.1 Hz, 2H, H-1); 3.94 (s, 2H, H-3); 4.86-4.92 (m, 2H, H-5).
NMR $^{31}$P (D$_2$O), δ(ppm): −21.2 (dd, J$_{β-α}$ 26.0 Hz, J$_{β-γ}$ 19.5 Hz, P-β); −6.60 (d, P-γ); 10.2 (d, P-α).
NMR $^{13}$C (D$_2$O), δ(ppm): 19.01 (1C, C-6); 65.83 (d, 163.6 Hz, 1C, C-1); 76.75 (d, J$_{3-P}$ 11.3 Hz, 1C, C-3); 113.61 (1C, C-5); 142.33 (1C, C-4).
MS FAB>0 m/z (GT): 327 [M−4NH$_4$+5H]$^+$.

Example 111

Triammonium α,γ-(4-methyl-2oxa-pent-4-enyl)-triphosphonate (100)

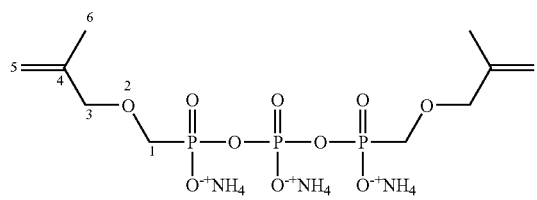

Total formula: C$_{10}$H$_{30}$N$_3$O$_{10}$P$_3$
Yield=9%
R$_f$=0.41 (5:5, 27% ammonia: isopropanol).
NMR $^1$H (D$_2$O), δ(ppm): 1.63 (s, 6H, H-6); 3.39 (d, J$_{1-P}$ 8.6 Hz, 2H, H-1); 3.95 (s, 2H, H-3); 4.85-4.95 (m, 2H, H-5).
NMR $^{31}$P (D$_2$O), δ(ppm): −21.9 (t, J$_{β-α}$=J$_{β-γ}$ 25.0 Hz, P-β); 10.1 (d, 2P, P-α and P-γ).
NMR $^{13}$C (D$_2$O), δ(ppm): 18.95 (2C, C-6); 65.85 (d, J$_{1-P}$ 163.7 Hz, 2C, C-1); 76.77 (d, J$_{3-P}$ 11.3 Hz, 2C, C-3); 113.67 (2C, C-5); 142.45 (2C, C-4).
MS FAB>0 m/z (GT): 395 [M−3NH$_4$+4H]$^+$.

Example 112

Diammonium α,β-(4-methyl-2oxa-pent-4-enyl)-pyrophosphonate (101)

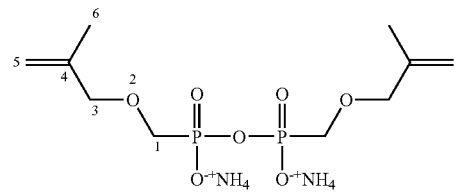

Total formula: C$_{10}$H$_{26}$N$_2$O$_6$P$_2$
Yield=18%
R$_f$=0.60 (5:5, 27% ammonia: isopropanol).
NMR $^1$H (D$_2$O), δ(ppm): 1.62 (s, 6H, H-6); 3.55-3.61 (d, J$_{1-P}$ 8.3 Hz, 2H, H-1); 3.93 (s, 4H, H-3); 4.85-4.93 (m, 4H, H-5).
NMR $^{31}$P (D$_2$O), δ(ppm): 9.9.
NMR $^{13}$C (D$_2$O), δ(ppm): 19.10 (2C, C-6); 65.98 (d, J$_{1-P}$ 164.0 Hz, 2C, C-1); 76.81 (d, J$_{3-P}$ 11.3 Hz, 2C, C-3); 113.62 (2C, C-5); 142.45 (2C, C-4).
MS FAB>0 m/z (GT): 315 [M−2NH$_4$+3H]$^+$.

Example 113

Human Peripheral Blood T Lymphocyte Proliferation Activation

Human peripheral blood lymphocytes (PBMC) are isolated from donors' by centrifugation on Ficoll-Hypaque. They are then placed in culture in 96-well plates at a rate of 2.10$^6$ cells/ml in 200 μl of RPMI 1640 medium (Gibco) containing 10% foetal calf serum or human AB serum, 20 mM of Glutamine, 10 mM Hepes, 1 mM of sodium pyruvate, 10 μg/ml of penicillin-streptomycin. The molecules under test are then added at final concentrations ranging from 0.001 μM to 500 μM. Each condition is produced in triplicate. The molecules are diluted in isotonic phosphate buffer (PBS). The cells are then incubated at 37° C.-5% CO2 for 4 days. Cell proliferation is then determined by measuring the incorporation of thymidine $^3$H ($^3$H-TdR). For this, 0.5 μCi of $^3$H-TdR is added per culture. After 24 hours, the cells are retrieved on Cell Harvester (Packard Instruments) and the radioactivity incorporated in high molecular weight material is counted using a Rack-Beta counter (Packard).

The stimulation indices are evaluated as follows:

$$\text{Index } (cpm) = \frac{(cpm/\text{culture in presence of molecule}) - (cpm/\text{molecule} - \text{free culture} \times 100)}{(CPM/\text{molecule} - \text{free culture})}$$

In all the experiments, isoprenyl pyrophosphonate (IPP) is selected as the reference. The results are shown in FIG. 1, which represents the proliferation index as a function of each molecule for the various concentrations tested. In this figure, it is observed that the molecules M$_1$: (E) 1-pyrophosphono-4-methylpenta-1,3-diene, M$_2$: (E) 1-pyrophosphono-penta-1,3-diene, M$_3$: (E) 1-pyrophosphono-buta-1,3-diene, M$_4$: 5-pyrophosphono-2-methylpent-2-ene, M$_5$: α,γ-di-[4-methylpent-4-enyl]-triphosphonate, $M_6$: 5-pyrophosphono-2-methylpentene, $M_7$: 5-triphosphono-2-methylpentene are more effective than IPP in inducing T lymphocyte proliferation.

Example 114

Vγ9/Vδ2 Lymphocyte Expansion

In order to verify selectivity with respect to Vγ9/Vδ2 lymphocytes of the molecule activating potential, PBMCs, cultured under the conditions described above were analysed after 5 days of culture in the presence of various molecules by flow cytometry immunofluorescence. For this, the cells are retrieved, washed in PBS and then incubated in the presence of human anti-CD3 monoclonal antibodies conjugated with fluoroscein (FITC, FL1) and human anti-Vγ9 coupled with biotin and then detected with Streptavidine-phycoerythrin conjugate (ST-PE, FL2). The markings are produced by incubating for 30 minutes with 0.5 µg of each antibody per million cells. The analysis is performed after washing on a FACScalibur-SORT cell analyser-sorter cytofluorimeter (Becton Dickinson, Mountain View, Calif.). The results are processed using Cellquest software.

The results are shown in FIG. 2 (A to L).

FIG. 2A gives the profile (size FSC and granularity SSC) of the cells studied. FIG. 2B shows a fresh PBMC before culture. FIG. 2C shows a fresh PBMC after 5 days in culture. FIGS. 2D to 2L show a PBMC after 5 days in culture in the presence of the molecule tested.

FIG. 2D: 1 µg/ml phytohaemagglutinin A (PHA)

FIG. 2E: 100 µM isoprenylpyrophosphate (IPP)

Figures 2F, 2G, 2H, 2I:
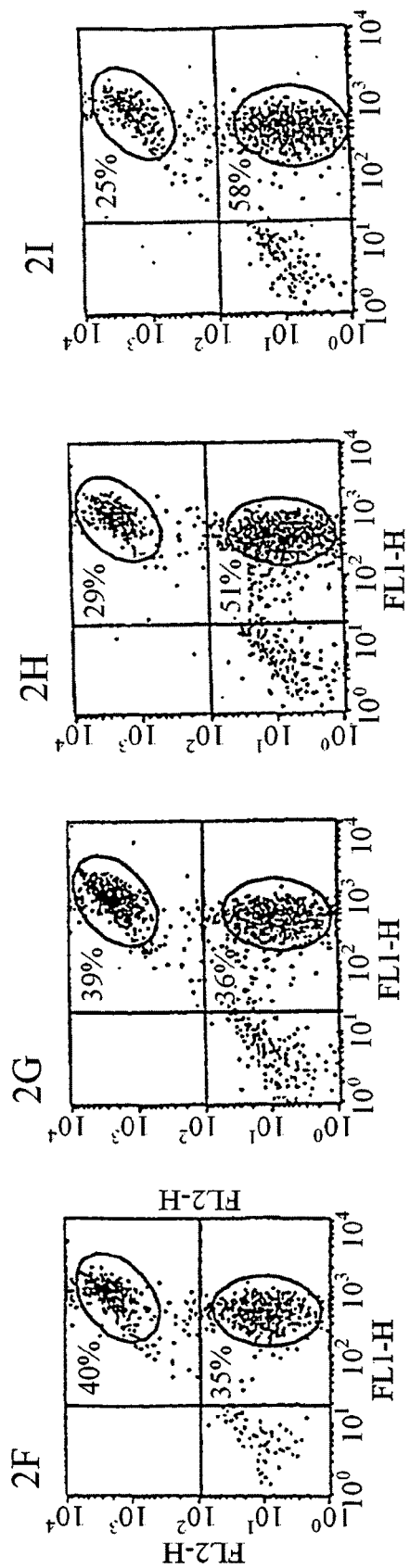

FIG. 2F: 100 µM 1-pyrophosphono-4-methylpenta-1,3-diene

FIG. 2G: 100 µM (E) 1-pyrophosphono-penta-1,3-diene

FIG. 2H: 100 µM (E) 1-pyrophosphono-buta-1,3-diene

FIG. 2I: 100 µM 5-pyrophosphono-2-methylpent-2-ene

Figures 2J, 2K, 2L:
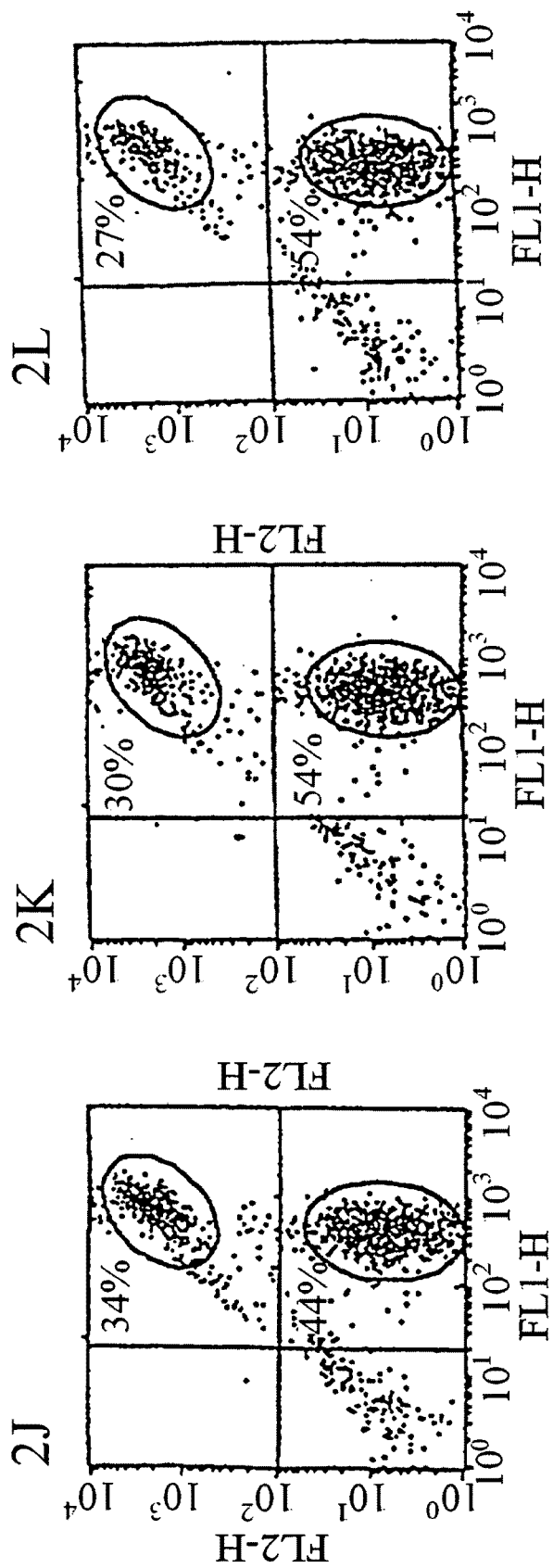

FIG. 2J: 100 µM α,γ-di-[4-methylpent-4-enyl]-triphosphonate

FIG. 2K: 100 µM 5-pyrophosphono-2-methylpentene

FIG. 2L: 100 µM 5-triphosphono-2-methylpentene

In FIG. 2B, the percentage of Vγ9/Vδ2 T cells in the peripheral blood of healthy donors is of the order of 2% before culture (1-5% depending on the subjects) from the total lymphocytes defined in the analysis window R1 (FIG. 2A).

FIGS. 2C and 2D show that there is no Vγ9/Vδ2 T cell enrichment in non-stimulated control cultures or in cultures stimulated with a non-selective polyclonal activator, phytohaemagglutinin A (PHA) (FIG. 2D). On the other hand, a high increase in the Vγ9/Vδ2 T cell population is observed in cultures stimulated with IPP or with the molecules according to the invention: (E) 1-pyrophosphono-4-methylpenta-1,3-diene, (E) 1-pyrophosphono-penta-1,3-diene, (E) 1-pyrophosphono-buta-1,3-diene, 5-pyrophosphono-2-methylopent-2-ene, α,γ-di-[4-methylpent-4-enyl]-triphosphonate, 5-pyrophosphono-2-methylpentene, 5-triphosphono-2-methylpentene. These observations demonstrate that these molecules selectively induce Vγ9/Vδ2 T cell proliferation.

This conclusion is confirmed in that in some experiments, the cells were cultured for 3 weeks in the presence of one of the various molecules and 20 U/ml of interleukin 2 (IL2). Under these conditions, all the cells retrieved after cultures corresponds to CD3+Vγ9/Vδ2 T cells.

Example 115

In Vivo Stability of the Compounds According to the Invention

Figure 3:
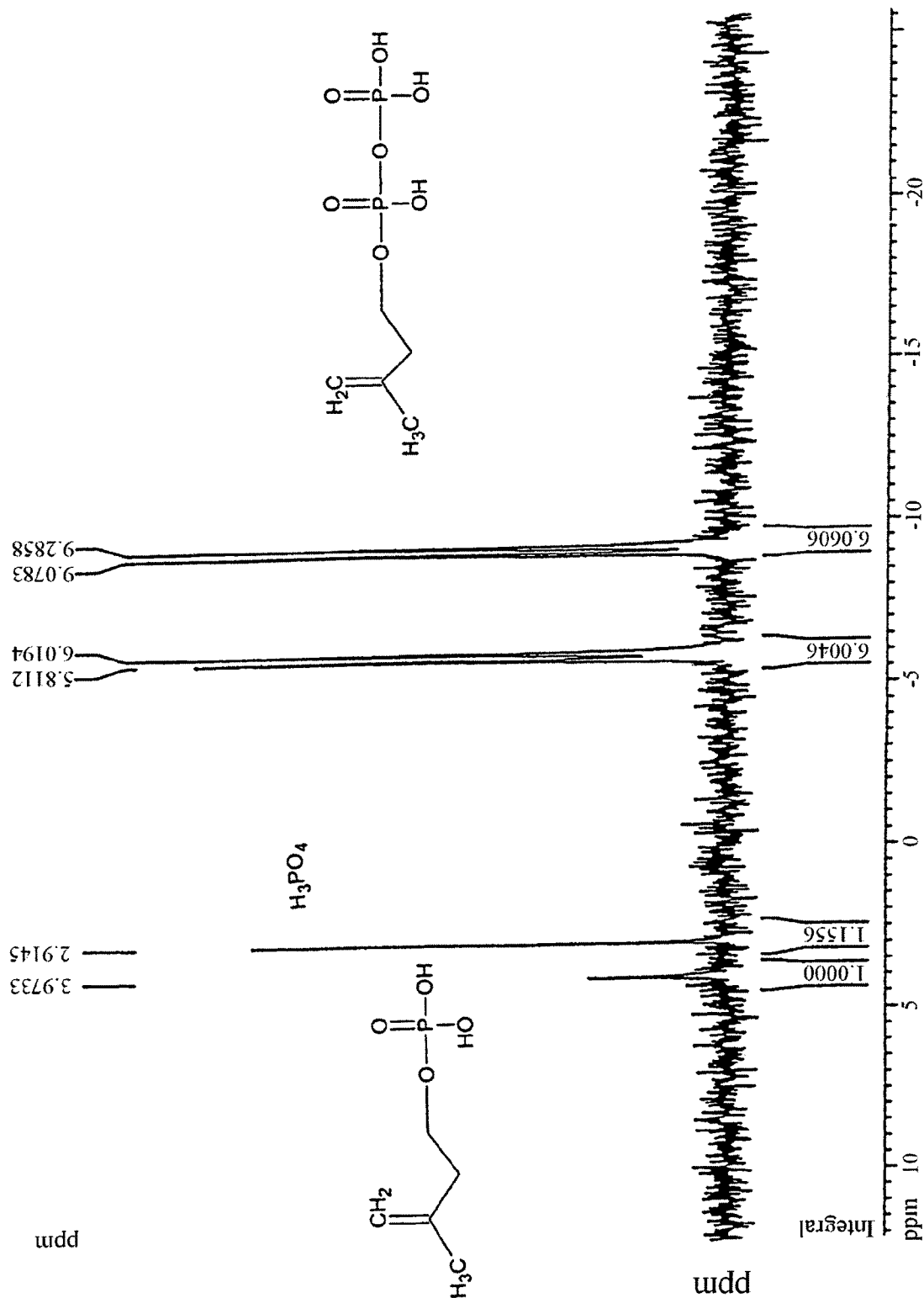
FIG. 3. NMR spectra for an isopentenyl pyrophosphate solution in $D_2O$.
Figure 4:
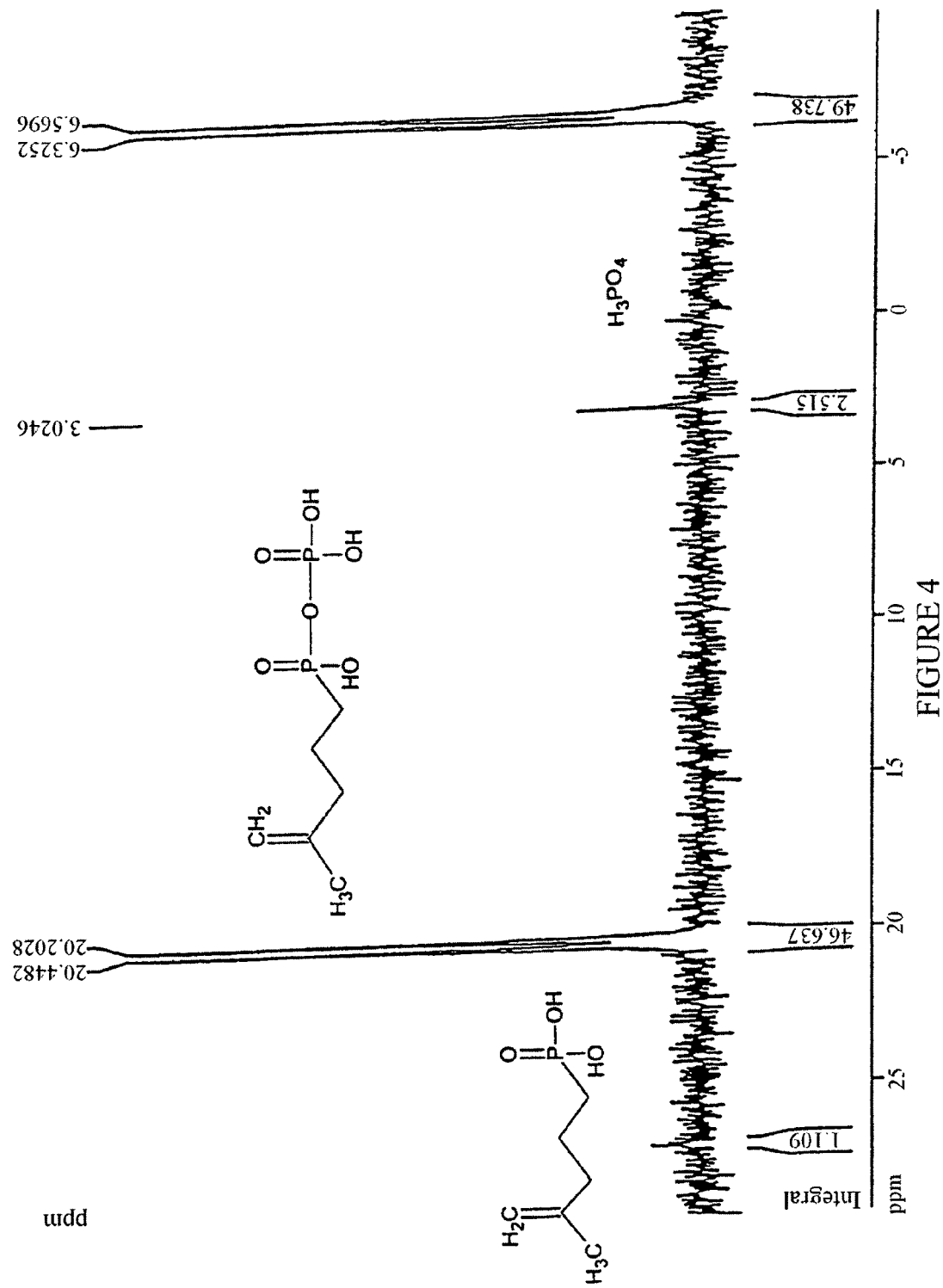
FIG. 4. NMR spectra for an isopentenyl pyrophosphonate (IPPN) solution in $D_2O$.

In order to demonstrate the improved in vivo stability of the compounds according to the invention compared to isopentenyl pyrophosphate (IPP), the following tests were carried out: an isopentenyl pyrophosphate solution in $D_2O$ and an isopentenyl pyrophosphonate (IPPN) solution in $D_2O$ were prepared, both solutions being at a concentration of 0.1 mole/liter. To 0.5 ml of each solution, 500 µl of human AB serum was added and the mixture were left to incubate. After three days of incubation, the degradation of the molecule is measured by phosphorus 31 NMR. The results are given in FIGS. 3 and 4 where the NMR spectra of the sample comprising IPP and that comprising IPPN are shown respectively: it is thus observed that, after three days of incubation, IPP has undergone significant degradation, the integral of the peak corresponding to isoprenyl phosphate (δ=3.97) being evaluated at 1, while that of the peak corresponding to IPP is evaluated at 1.2. Meanwhile, IPPN has changed negligibly, isoprenyl phosphonate giving a peak (δ~27) wherein the integral is evaluated at 1.1, as opposed to 96 for IPPN. These results demonstrate that, under physiological conditions, IPPN remains stable while IPP is degraded rapidly.

The invention claimed is:

1. A method for modulating γ9δ2 T lymphocyte proliferation comprising contacting a γ9δ2 T lymphocyte with, or administering to a subject in need thereof, an effective amount of a compound of formula (I):

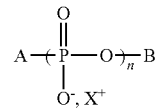

wherein A is $C_5$-$C_{50}$ alkyl, alkenyl, or alkynyl, which may be linear, branched, or cyclic, and may optionally be substituted by:
one or more substituents selected from the group consisting of a carboxylic acid, an ester, an amide, a nitrile, a hydroxyl, an aldehyde, a ketone, a halogen, an amine, a thiol, a thio-ketone, an episulfide, a selenol, a selenoketone, a sulfide, a sulfone, and a sulfoxide;
n is an integer from 1 to 4,
X is hydrogen, $H^+$, $Na^+$, $NH_4^+$, $K^+$, $Li^+$, $(CH_3CH_2)_3NH^+$ or an enzyme labile ester,
B is X or is a group:

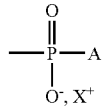

wherein X and A are as defined above.

2. The method of claim 1, comprising contacting said compound with a γ9δ2 T lymphocyte in vitro and determining whether said compound stimulates γ9δ2 T lymphocyte proliferation.

3. The method of claim 1, comprising contacting said compound with a γ9δ2 T lymphocyte in vitro and determining whether said compound inhibits γ9δ2 T lymphocyte proliferation.

4. The method of claim 1, comprising administering said compound to a subject having a condition that induces activation of γ9δ2 T lymphocytes.

5. The method of claim 1, comprising administering said compound to a subject having an infectious disease.

6. The method of claim 1, comprising administering said compound to a subject having a chronic inflammatory disease.

7. The method of claim 1, wherein A is alkenyl and has at least one double bond

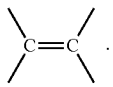

8. The method of claim 1, wherein A has 5 to 25 carbon atoms.

9. The method of claim 1, wherein A has at least one α-halohydrine group according to formula (II) below, wherein Y represents an atom selected from the group consisting of fluorine, iodine and bromine:

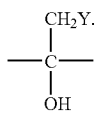
(II)

10. The method of claim 1, wherein A has at least one epoxide group.

11. The method of claim 1, wherein A has at least one tertiary alcohol group.

12. The method of claim 1, wherein A has at least one α-diol group.

13. The method of claim 1, wherein A has at least one aldehyde group or α-hydroxyaldehyde group.

14. The method of claim 1, wherein $X^+$ is selected from the group consisting of $H^+$, $Na^+$, $NH_4^+$, $K^+$, $Li^+$, and $(CH_3CH_2)_3NH^+$.

15. The method of claim 1, wherein A has between 5 to 10 carbon atoms.

16. The method of claim 1, wherein A is alkyl.

17. The method of claim 1, comprising administering said compound in combination with a pharmaceutically acceptable excipient.

18. The method of claim 1, comprising administering said compound to a subject having a disease caused by a pathogen selected from the group consisting of human immunodeficiency virus, simian immunodeficiency virus, herpes simplex virus, human herpes virus 6, and vaccinia virus; or to a subject having tuberculosis, salmonellosis, brucellosis, tularaemia, malaria or listeriosis.

19. The method of claim 1, comprising administering said compound to a subject having a disease selected from the group consisting of systemic lupus erythematosus, multiple sclerosis, rheumatoid arthritis, Behcet's disease, allogenic transplant rejection, chronic autoimmune hepatitis, polymyositosis, and inflammatory colon disease.

20. The method of claim 1, comprising administering said compound to a primate.

* * * * *

UNITED STATES PATENT AND TRADEMARK OFFICE
CERTIFICATE OF CORRECTION

| | |
|---|---|
| PATENT NO. | : 8,017,596 B2 |
| APPLICATION NO. | : 12/656049 |
| DATED | : September 13, 2011 |
| INVENTOR(S) | : Jean-Louis Montero et al. |

It is certified that error appears in the above-identified patent and that said Letters Patent is hereby corrected as shown below:

Column 5,
Line 51, "unsaturation at a of the" should read --unsaturation at α of the--.

Column 7,
Line 13, "in a of" should read --in α of--.

Column 8,
Line 50, "in a of phosphorus" should read --in α of phosphorus--.

Column 13,
Line 3, "chemicals", 3$^{rd}$ Edition" should read --chemicals", Pergamon Press, 3$^{rd}$ Edition--.

Column 14,
Line 46, "NMR $^{13}$C( CDCL$_2$)" should read --NMR $^{13}$C(CDCL$_3$)--.

Column 16,
Line 24, "5.5-578" should read --5.5-5.78--.

Column 18,
Line 33, "(dd, J$_{4b-3}$ 6.4 Hz, 1H, H-4-b)" should read --(dd, J$_{4b-3}$ 6.4 Hz, 1H, H-4b)--.
Line 65, "10, C-2')" should read --(1C, C-2')--.

Column 24,
Line 20, "(10, C-4);" should read --(1C, C-4);--.

Column 25,
Line 43, "(10, C-9');" should read --(1C, C-9');--.
Line 44, "(d, J$_{9'-P}$ 190 Hz, 1C, C-9)" should read --(d, J$_{9'-P}$ 190 Hz, 1C, C-9')--.

Signed and Sealed this
Sixth Day of March, 2012

David J. Kappos
*Director of the United States Patent and Trademark Office*

Column 26,
Line 37, "δ(Ppm)" should read --δ(ppm)--.

Column 27,
Lines 8-9, "(m, 4H, Har)" should read --(m, 4H, H-ar)--.

Column 28,
Line 36, "7.30-751" should read --7.30-7.51--.

Column 32,
Line 33, "J3-4 10.0 Hz" should read --$J_{3-4}$ 10.0 Hz--.
Line 59, "J1-2 16.9 Hz" should read --$J_{1-2}$ 16.9 Hz--.

Column 33,
Line 19, "δ(Ppm)" should read --δ(ppm)--.

Column 34,
Line 24, "δ(Ppm)" should read --δ(ppm)--.

Column 35,
Line 27, "δ(Ppm)" should read --δ(ppm)--.

Column 36,
Line 23, "δ(Ppm)" should read --δ(ppm)--.
Lines 64-65, "(d, 185.1 Hz, 1C, C-1)" should read --(d, $J_{1\text{-}P}$ 185.1 Hz, 1C, C-1)--.

Column 37,
Line 21, "$J_{\beta\text{-}\alpha}$=J β-γ=22.2 Hz" should read --$J_{\beta\text{-}\alpha}$=$J_{\beta\text{-}\gamma}$=22.2 Hz--.
Line 48, "$J_{\beta\text{-}\alpha}$=$J_{\beta\text{-}\alpha}$22.4 Hz" should read --$J_{\beta\text{-}\alpha}$=$J_{\beta\text{-}\gamma}$ 22.4 Hz--.

Column 50,
Line 67, "[M-4NH$_4$+5]$^+$" should read --[M-4NH$_4$+5H]$^+$--.

Column 53,
Line 4, "[M-3NH$_4$+4 H]$^+$" should read --[M-3NH$_4$+4H]$^+$--.
Line 41, "is concentrate to" should read --is concentrated to--.

Column 53,
Line 5, "$C_9H_{19}D_3P$" should read --$C_9H_{19}O_3P$--.

Column 55,
Lines 32-33, "9m, 2H, H-4)" should read --(m, 2H, H-4)--.

CERTIFICATE OF CORRECTION (continued)
U.S. Pat. No. 8,017,596 B2

Column 56,
Line 26, "[M-3NH$_4$+4]$^{+}$" should read --[M-3NH$_4$+4H]$^{+}$--.

Column 57,
Line 40, "[M-4NH$_4$+51-1]$^{+}$" should read --[M-4NH$_4$+5H]$^{+}$--.
Line 62, "δ(Pppm)" should read --δ(ppm)--.
Line 67, "[M-4NH$_4$+5]$^{+}$" should read --[M-4NH$_4$+5H]$^{+}$--.

Column 58,
Line 51, "[M-3NH$_4$+4]$^{+}$" should read --[M-3NH$_4$+4H]$^{+}$--.

Column 59,
Lines 8-9, "J$_{5-P}$ 10.7 Hz" should read --J$_{2-P}$ 10.7 Hz--.

Column 62,
Line 13, "H-8):" should read --H-8);--.
Line 17, "NMR $^{13}$C (2 (CDCl$_3$)" should read --NMR $^{13}$C (CDCl$_3$)--.
Line 42, "NMR $^{13}$C (2 (acetone-d$_6$)" should read --NMR $^{13}$C (acetonc-d$_6$)--.

Column 63,
Line 34, "(d, 163.6" should read --(d, J$_{1-P}$ 163.6--.

Column 66,
Line 13, "mixture were left" should read --mixture was left--.

UNITED STATES PATENT AND TRADEMARK OFFICE
CERTIFICATE OF CORRECTION

PATENT NO. : 8,017,596 B2
APPLICATION NO. : 12/656049
DATED : September 13, 2011
INVENTOR(S) : Jean-Louis Montero et al.

Page 1 of 3

It is certified that error appears in the above-identified patent and that said Letters Patent is hereby corrected as shown below:

Column 5,
Line 51, "unsaturation at a of the" should read --unsaturation at α of the--.

Column 7,
Line 13, "in a of" should read --in α of--.

Column 8,
Line 50, "in a of phosphorus" should read --in α of phosphorus--.

Column 13,
Line 3, "chemicals", 3$^{rd}$ Edition" should read --chemicals", Pergamon Press, 3$^{rd}$ Edition--.

Column 14,
Line 46, "NMR $^{13}$C( CDCL$_2$)" should read --NMR $^{13}$C(CDCL$_3$)--.

Column 16,
Line 24, "5.5-578" should read --5.5-5.78--.

Column 18,
Line 33, "(dd, J$_{4b-3}$ 6.4 Hz, 1H, H-4-b)" should read --(dd, J$_{4b-3}$ 6.4 Hz, 1H, H-4b)--.
Line 65, "10, C-2')" should read --(1C, C-2')--.

Column 24,
Line 20, "(10, C-4);" should read --(1C, C-4);--.

This certificate supersedes the Certificate of Correction issued March 6, 2012.

Signed and Sealed this
Eighth Day of May, 2012

David J. Kappos
*Director of the United States Patent and Trademark Office*

Column 25,
Line 43, "(10, C-9');" should read --(1C, C-9');--.
Line 44, "(d, $J_{9'-P}$ 190 Hz, 1C, C-9)" should read --(d, $J_{9'-P}$ 190 Hz, 1C, C-9')--.

Column 26,
Line 37, "δ(Ppm)" should read --δ(ppm)--.

Column 27,
Lines 8-9, "(m, 4H, Har)" should read --(m, 4H, H-ar)--.

Column 28,
Line 36, "7.30-751" should read --7.30-7.51--.

Column 32,
Line 33, "J3-4 10.0 Hz" should read --$J_{3-4}$ 10.0 Hz--.
Line 59, "J1-2 16.9 Hz" should read --$J_{1-2}$ 16.9 Hz--.

Column 33,
Line 19, "δ(Ppm)" should read --δ(ppm)--.

Column 34,
Line 24, "δ(Ppm)" should read --δ(ppm)--.

Column 35,
Line 27, "δ(Ppm)" should read --δ(ppm)--.

Column 36,
Line 23, "δ(Ppm)" should read --δ(ppm)--.
Lines 64-65, "(d, 185.1 Hz, 1C, C-1)" should read --(d, $J_{1-P}$ 185.1 Hz, 1C, C-1)--.

Column 37,
Line 21, "$J_{\beta-\alpha}$=J β-γ=22.2 Hz" should read --$J_{\beta-\alpha}$=$J_{\beta-\gamma}$=22.2 Hz--.
Line 48, "$J_{\beta-\alpha}$=$J_{\beta-\alpha}$22.4 Hz" should read --$J_{\beta-\alpha}$=$J_{\beta-\gamma}$ 22.4 Hz--.

Column 50,
Line 67, "[M-4NH$_4$+5]$^+$" should read --[M-4NH$_4$+5H]$^+$--.

Column 53,
Line 4, "[M-3NH$_4$+4 H]$^+$" should read --[M-3NH$_4$+4H]$^+$--.
Line 41, "is concentrate to" should read --is concentrated to--.
Line 58, "$C_9H_{19}D_3P$" should read --$C_9H_{19}O_3P$--.

Column 55,
Lines 32-33, "9m, 2H, H-4)" should read --(m, 2H, H-4)--.

Column 56,
Line 26, "[M-3NH$_4$+4]$^{+}$" should read --[M-3NH$_4$+4H]$^{+}$--.

Column 57,
Line 40, "[M-4NH$_4$+51-1]$^{+}$" should read --[M-4NH$_4$+5H]$^{+}$--.
Line 62, "δ(Ppm)" should read --δ(ppm)--.
Line 67, "[M-4NH$_4$+5]$^{+}$" should read --[M-4NH$_4$+5H]$^{+}$--.

Column 58,
Line 51, "[M-3NH$_4$+4]$^{+}$" should read --[M-3NH$_4$+4H]$^{+}$--.

Column 59,
Lines 8-9, "J$_{5-P}$ 10.7 Hz" should read --J$_{2-P}$ 10.7 Hz--.

Column 62,
Line 13, "H-8):" should read --H-8);--.
Line 17, "NMR $^{13}$C (2 (CDCl$_3$)" should read --NMR $^{13}$C (CDCl$_3$)--.
Line 42, "NMR $^{13}$C (2 (acetone-d$_6$)" should read --NMR $^{13}$C (acetone-d$_6$)--.

Column 63,
Line 34, "(d, 163.6" should read --(d, J$_{1-P}$ 163.6--.

Column 66,
Line 13, "mixture were left" should read --mixture was left--.